(12) United States Patent
Ainley et al.

(10) Patent No.: US 6,384,207 B1
(45) Date of Patent: May 7, 2002

(54) REGULATORY SEQUENCES FOR TRANSGENIC PLANTS

(75) Inventors: Michael Ainley, Carmel; Katherine Armstrong, Zionsville; Scott Belmar, Indianapolis, all of IN (US); Otto Folkerts, Guilford, CT (US); Nicole Hopkins; Michael A. Menke, both of Indianapolis, IN (US); Dayakar Pareddy, Carmel, IN (US); Joseph F. Petolino, Zionsville, IN (US); Kelley Smith, Lebanon, IN (US); Aaron Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/097,319

(22) Filed: Jun. 12, 1998

Related U.S. Application Data

(60) Provisional application No. 60/049,752, filed on Jun. 12, 1997.

(51) Int. Cl.$^7$ .......................... C12N 5/04; C12N 15/29; A01H 5/00; A01H 5/10; C07H 21/04
(52) U.S. Cl. ...................... 536/24.1; 800/298; 435/410; 435/419; 435/320.1; 536/23.1
(58) Field of Search ..................... 435/6, 69.1, 468, 435/470, 410, 419, 320.1; 536/23.1, 23.2, 23.4, 23.6, 24.1; 800/278, 287, 290, 292, 293, 295, 298, 320, 320.1

(56) References Cited

U.S. PATENT DOCUMENTS 5,633,363 A   5/1997   Colbert et al. .............. 536/24.1
5,635,618 A   6/1997   Capellades et al. .......... 800/288

FOREIGN PATENT DOCUMENTS

EP   0 452 269 A2   10/1991
EP   0 559 603 A2   9/1993
WO   WO 95/06128    3/1995
WO   WO 97/04114    2/1997

OTHER PUBLICATIONS

Cornejo et al. Plant Molecular Biology. 1993. vol. 23:567–581.*
Christensen et al. Plant Molecular Biology. 1992. vol. 18:675–689.*
Kim et al. Plant Molecular Biology. 1994. vol. 24:105–117.*
EMBL Sequence Accession No. D48704, Sasaki et al. Rice cDNA, partial sequence (S15089 1A) Mar. 9, 1995.
EMBL Sequence Accession No. X88779, Tacke et al., "Z. mays glossy2 locus DNA" Aug. 16, 1995.
EMBL Sequence Accession No. X98774, Welinder et al., "A. thaliana mRNA for peroxidase ATP6a, EST clone 157A5T7", Jul. 10, 1996.
EMBL Sequence Accession No. X98320,10, "A. thalian mRNA for peroxidase, prxr8", Jun. 10, 1996.
Derwent Abstract 92–189675 (1992) abstracitng JP4126088A (Toyobo KK).
Derwent Abstract 96–378129 (1996) abstracting JP8182495A (Sumitomo Chem. Co. Ltd.).
Derwent Abstract 95–211625 (1995) abstracting JP7123982A (Nippon Seishi KK).
Biological Abstracts, vol. 80, abstract 27633 (1985) abstracting Brewbaker et al., "Genetic polymorphisms of 13 maize [Zea mays] peroxidases," J. Hered. 76(3): 159–167, 1985.
M. Baga et al., "Molecular cloning and expression analysis of peroxidase genes from wheat," Plant Molecular Biology 29: 647–662, 1995.
J. Kyozuka et al., "Anaerobic induction and tissue–specific expression of maize Adh1 promoter in transgenic rice plants and their progeny," Mol Gen Genet (1991) 228:40–48.
D. McElroy et al., "Foreign gene expression in transgenic cereals," Trends in Biotechnology, vol. 12, 1994, 62–68.

* cited by examiner

*Primary Examiner*—Amy J. Nelson
*Assistant Examiner*—O. M. F. Zaghmout
(74) *Attorney, Agent, or Firm*—Donald R. Stuart

(57) ABSTRACT

Regulatory sequences derived from a maize root preferential cationic peroxidase gene (Per5), including the promoter, introns, and the 3′ untranslated region, are useful to control expression of recombinant genes in plants.

4 Claims, No Drawings

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 6550 base pairs
      (B) TYPE: nucleic acid
      (C) STRANDEDNESS: double
      (D) TOPOLOGY: linear (ii) MOLECULE TYPE: DNA (ix) FEATURE:
      (A) NAME/KEY: exon
      (B) LOCATION: 4201..4425
      (D) OTHER INFORMATION: /product= "Peroxidase"

(ix) FEATURE:
      (A) NAME/KEY: intron
      (B) LOCATION: 4426..5058

(ix) FEATURE:
      (A) NAME/KEY: exon
      (B) LOCATION: 5059..5250

(ix) FEATURE:
      (A) NAME/KEY: intron
      (B) LOCATION: 5251..5382

(ix) FEATURE:
      (A) NAME/KEY: exon
      (B) LOCATION: 5383..5548

(ix) FEATURE:
      (A) NAME/KEY: intron
      (B) LOCATION: 5549..5649

(ix) FEATURE:
      (A) NAME/KEY: exon
      (B) LOCATION: 5650..6065

(ix) FEATURE:
      (A) NAME/KEY: CDS
      (B) LOCATION: join(4201.. 4425, 5059..5250, 5383..5547, 5649 ..6068)

(xi) SEQUENCE DESCRIPTION: SEQ ID NO:1:

```
CCATGGCCAG TTGCCGGTGG AGCAGGTAAA AACACCGTAG CGTAGCAGCC A GGCGGAAGC      60

AGACGCACAG CACAGGTTGG TTATGATAGT CAGCCGGGCC ACATGTGTGT A GTTGGTACA     120

CTGATACGCT TACACTGTCT CTCCTTTCTT TTTTATTTGT CACCTTTGGT C GAGCTTACA     180
```

-continued

```
TAATTGTGTG ACTAAAAAAA GGTCACTTCA TTCAGAAATT TAGGGTTGTG G GAATTTTGG      240

ATTTTATTGT GTCTGTATAG AGTAGCTATA GCTAGCTAGC TAGATGTGAT G TTAATAATT      300

ATGACGATGA GATTGGCCCG CTTGGCCGCT TGCATTGTCT CCCTAGCTCA A TAATGTTTT      360

GAGTTTGTCT TGCCTTTCTT TCAGCTCTAA CAAATTGGAG TAGGGATGAC T GAGATACAT      420

ATATAAAAGC GAAAACCGCT GCTCTCTGTT AATTATTGCA CATCACACAT A GGCCAAGCC      480

TTAAGGACAA TCAACTAAGG ATGGTAATAA CTAAGGCTAG TGAGGTCGAA C TAGGGATGT      540

TAATATACTC TAGATTTTAG ACTATAAAAT TTAAGGATCG AATCAGATTA G TATCGAACT      600

ATATTTATAT TCATTTCTAA ACTAAATTAA TTAAGCACCC TAAATTATTG T GATGAAGAG      660

ACATTTCGAT CGTGATCCAT TATTACTCCT TGGTCAAACT AATCTCGTTT T ATGTCACTA      720

TTTCATCATC TTTTTTGCGA ACGGGTTTAT AGCCCGTGTT CCATTATGAG G ACATGAACG      780

GTTTAAACAA AGTTACATAT CATCCCAGCT AGCTACCTAG ATTGGAAGCA T GGGTTCGGT      840

ATATATATAT AGTTTATATA TTTGGTATAT ATATATATAT ATATATATAT A TATATATAT      900

CACACGTCAG CTTATATTAC GTAAAGTGGG GTTAGTTTTC AAGAAGCGTG G GACCAGTCA      960

CCTCTGCAGT CTGACCTTGG CTTCAGCTTC GACAGCAAAC AGTCATCTCT T GGAAGCTAA     1020

GGACAGTCTC CAACAGTCAA CAAAGCAGCG GTCTGCTTGT AGTTCTCCCT T GCACGACCA     1080

GCTATATCTA GCATCATAAC AACGGTAAGA TCATCTCTAG CACGACAAAC T TAGTTTAAT     1140

TAATTATGTC TAATCCGTTG TTGTTAGCTT AAACTTTCTA GCCTCCTATG C TAAGAGAGT     1200

TCTCTAGTTC TACTCAGGTG GATTGATATA TAAATTGGGA ATCTTCTAGG C GTCACAAGG     1260

TATGGTACAC ATCAATCAAT GAACGGACAA AGCAACGGTA AGATCCGACC C AGTAAAAGT     1320

AATAGCGTTA GGGCATGTAC AACCTAGACA CTGATGCACA GTACTCCAAG T ATAAGACAC     1380

AACTAAAACA CAACATAATA ATACAGTGGT TATATCTAAA ACATGTGTCT T ACCATATTC     1440

ATTGTACCAA TTAGAACATT TAATAAATTA AAGTGACCAA TCAGCTAGCC T CCTGTCTCG     1500

AACATAGAGC TAAGACATTG TGTCTTCGTC AAGATACATG TCTTAAGTTT T TTTATATTC     1560

ACTCCCAAAG ACACACTCTA AGACACAACG TAACACACCC ATTGTACATG C TCTTAACCT     1620

AAGTTATCAT GGATGACCAC GCGTGGCAAT TAAAAAAATA ATTTTTGCCT C CTAAAACCT     1680

CTTTCTTAAT TGGTTCTTGC TTGCAAATCA CCAGCGAACC CATATGAAAG G ATGCTCAAA     1740

ATCTGGCCAC CGCATCAGGG TTGGTGAATG CAACGTAAAA AATAATGCAT A AATCAGCTC     1800

TCTGATCAGT TATATAATCG TGCCTTTTAA TTATTCATGC CAGCTTTATC T GACTCACGA     1860

AATCATTGAT AAATTATTCC TCAGCTGTAT TAGAAAGAGC AGTGTTGTTT A ACTTGGAAA     1920

GTGATGTGGA AGCGTGTGAT TGCGGTTGAG CTTGTATAGG AGTAAAATGA G GAACAGTAG     1980

GAAAATAATT TTTTCGGATT AAAACCGGTT GTTTGGACTG CGGCAGATAC A ATTCATAGA     2040

GATAAAAACA CCGTAGAAGT ATTAGAAGCC GATAAAGATT AAACCCAAAT G AACGAACAG     2100

GCTAAACAAA TCCGGCGCCT CAAAAGTCAA GAGCAGGTAC TGGGCTGTCT T GCACACGTC     2160

GCTTTTTGTC TCCCCCTGGC CCCTGGGTGA GAGTAGTAGG GATGCTAAAG T TTGCTTTCT     2220

CTTTTTGAGG CATGTGATAG GCTCTTGTTA GTTGCTAGGG CTATGTTTAT A ATATTTGCG     2280

CTTTTACCTA TGTACGTAAG AACCGGATGG AATAATGCTA TGCAGGAACC A ATTATGTTT     2340

GGTCGAAATA TATAGTGACC TATCATAATG TTATCCCTGT TCATGTACCT A GGTGGCTAA     2400

TGATATACGG CATATGAATA CAGTAATCAT CCAAGCACGT AAAAACTCGC T AGACGTTTA     2460

TGCCTGCTAG CCTGCTGGGT GTGTAGACTG GAGTACTGGA CAAACATCGC A ATACAGAGG     2520
```

```
TACAGTATTT GTCTAGACAA TGATATACAT AGATAAAAAC CACTGTTGTA A CTTGTAAGC      2580

CACTAGCTCA CGTTCTCCAT GAGCTCTTCT CTCTGCTGTT TCTTCCTCTG C TAACTGCGT      2640

TATGATATGA CGTCGTATAA ATAATCTCAC AATACTTCCT TATTTTCAGC A TGGCCTCTT      2700

TTATGTTTAT TTAACAGTAG CAACCAACGC CGCTCGATGT TTCCTTCAAG A AACGGCCAC      2760

TCACTATGTG GTGTGCAGAA GAACAAATGT AAGCAGCTCC TACAGGTACC A GTAGTCATG      2820

TCAGTGTGGA AGCTTTCCAA CCAACGCCTC CTTCGAGGAA CCTGGTCGTG C TGACATGAA      2880

TGTAGGCCAT GCAAGCACAA GCACCTAACG CGAATCATCA CGACGCGCCG T GTACTGGGC      2940

GTTGGTACAT CACACCCCGC GTTTGACCTG ATCGGAAGCA TGCGTGTGTG T TGGCTGCAG      3000

GACCGGCTAT AGGTTTCCTG CATTGGACAG CAGAAGCCAG TCATGTTAGG C ACTCACGCG      3060

CTCCTGCCGT TTGATGAATC ATCCGGTCTT TCGTATTGAT CACTAGTTCA C TACGCTGAT      3120

ATAGCAAATT TTAAGATGTG AAACCACGAG ACGAGCGATA AATCTTAGAC G TTACCTATC      3180

CATATGAAGC TTGTGCGAAA AAAAGGCGTG CCGCTGTAGC ATCATTCGTA T ACACTTTTG      3240

TCCCCAAAGA CAGGGATACG AATCCATGCT CGACAGAACC CTCCCTTCCC T GCAGATAAC      3300

GACACTTAAG TATAACAAAA GTAGTTGGAT TATTTCAGAA GCAAAATCTC A CTTTTCGCT      3360

GGCCTTTTTG TACTTTGGTT ACTTGAGTTC AGACAGTGTA TGCTATATTG T CATGTGCTG      3420

CGTAAGGTTT AAATATGGTT CGACAAATAT ATCAGTATAT CACTACTTTG T TATGGGTGG      3480

GGCCTAGCAC AAACTTGATA CAGCTAGGAT AAAGTTAGAA CGATGACTGA T CTACTGTAA      3540

AGCGACACCT GTCCTGTTAT GGTAGTTTAA GTCCATTCCT GGACGACTCC A GATCCAGGA      3600

TATGATGCTG TTACATAATG CGATTGTTCA CAATAAAATT GCATGATGTT C TTCTACTCT      3660

TTAGGCAGTT TTGTTCAACA GGCAAGTTGC ATAATGCATG TGCATATATG A GCAGCATAA      3720

TCATCAATTA ATCATAGGTT CGTCATTTTA GTTTCACTCC TTCACATTAT T CCAGCCCTT      3780

GAAGAAAAAT GTAGCAGTGC TTGCTGTTTA ATAAGTGGCA GAGCTGTTTT C ACTCCACCT      3840

ACGCTTGTCT AGGACCAAAA TTTTAATCTG TCACTTTGAG CTAAAACTGA A GCACCAAAC      3900

CGCTACAAAA GAACGTAGGA GCTGAATTGT AACTTGATGG GATTACTATA G CAGTTGCTA      3960

CAGTTCTAGC TAGCTACCTT ATTCTATACG CATCACCCTA ACAACCCGGC T GACTGCTGC      4020

ATCTGACCCC ACCGTCCCCT GCTCCAAACC AACTCTCCTT TCCTTGCATG C ACTACACCC      4080

ACTTCCTGCA GCTATATATA CCACCATATG CCCATCTTAT GAAACCATCC A CAAGAGGAG      4140

AAGAAACAAT CAACCAGCAA CACTCTTCTC TTATAACATA GTACAGCGAA G GTAACTCAC      4200

ATG GCA ACT TCC ATG GGT TGT CTC GTC TTG C TC TGC CTT GTT TCT TCT        4248
Met Ala Thr Ser Met Gly Cys Leu Val Leu L eu Cys Leu Val Ser Ser
 1               5                   10                  15

CTC CTT CCC AGT GCC GTC CTT GGC CAC CCA T GG GGT GGC TTG TTC CCA        4296
Leu Leu Pro Ser Ala Val Leu Gly His Pro T rp Gly Gly Leu Phe Pro
            20                  25                      30

CAG TTC TAT GAC CAT TCG TGC CCC AAG GCG A AG GAG ATT GTG CAG TCC        4344
Gln Phe Tyr Asp His Ser Cys Pro Lys Ala L ys Glu Ile Val Gln Ser
         35                   40                    45

ATT GTG GCA CAG GCT GTG GCC AAG GAG ACC A GG ATG GCG GCA TCT TTA        4392
Ile Val Ala Gln Ala Val Ala Lys Glu Thr A rg Met Ala Ala Ser Leu
  50                  55                    60

GTC AGA CTG CAT TTC CAT GAC TGC TTT GTC A AG GTTCAATTCT GCTTCCTCTG      4445
Val Arg Leu His Phe His Asp Cys Phe Val L ys
 65                  70                  75

TTATGTTCTT TATATTACAT GCTCTGACAA AGCTATAAAG CTTGATACTG C AGTATAATA    4505

TAACAAGTTA GCTACACAAG TTTTGTACTT CAAGTCTTTT AACTATATGT T GGTGCAATA    4565
```

```
                                                   -continued

AGATTATGAG TAATCCATAT GAAGGTGTTG CAAGAGAACA TGAAAGGCAA A GATAAACGG        4625

ATGAACCCAT TACTAGCTTT GGCTGTATCA GACCAATAAC TTGAAATGCA C TTGTGCTAG        4685

CATGCCTAAG TATTAGAAAA GGTAGCATGG GAGAATCTAT ATTATTTTGG C TAACTTCTT        4745

TAGTTACTAT TGATTGATGA GAAAGCCTAC CATTGCCCAT GCCAGCCCTA A TGTCCCGGT        4805

GACATGATTG AGCCAGTACT ATGATTAATT TACTCTATTG TTCTCCTTTT T TGAGTGCTG        4865

TATAAGATGT CCTTTTTTTG AGCCACTCGA AAGATGTTT ACTTAACTCT A GTGCGCAAT         4925

GATTGGAGCT CTCAGTGCAA CGCATGTGCT CTGTAATCTA CTGTCACCAC T ACTCTGTAG        4985

TGTGTGCTTA AACTCTAAAC TATTCCACGT GGCTAGTAAT TACCAATCAT T TACAACACT        5045

GTTACATGTG TAG GGC TGC GAT GCT TCG GTG CTG T TG GAC AAC AGC AGC         5094
            Gly Cys Asp Ala Ser Val Leu Leu Asp Asn Ser Ser
                        80                  85

AGC ATA GTT AGT GAG AAA GGG TCC AAC CCG A AC AGG AAC TCC CTC AGG        5142
Ser Ile Val Ser Glu Lys Gly Ser Asn Pro A sn Arg Asn Ser Leu Arg
         90                  95                  100

GGG TTT GAG GTG ATC GAC CAG ATT AAG GCT G CT CTT GAG GCT GCC TGC       5190
Gly Phe Glu Val Ile Asp Gln Ile Lys Ala A la Leu Glu Ala Ala Cys
         105                 110                 115

CCA GGC ACA GTC TCC TGT GCC GAC ATT GTT G CC CTT GCG GCT CGT GAT       5238
Pro Gly Thr Val Ser Cys Ala Asp Ile Val A la Leu Ala Ala Arg Asp
120                 125                 130                 135

TCC ACC GCC CTG GTATGTTCCA CTATCGACAA TCCTTTCCAA C CTCAAGGAA             5290
Ser Thr Ala Leu

CAGACATGAT ATTTGTGTGT GTGTGTGTGT GTATATATAT ATATAGTGAT A GCTTTGGCA       5350

AACTTAGATA TTTTCTGAGC TCTAAACCGT AG GTT GGT GGA CC A TAC TGG GAC       5403
                                    Val Gly Gly Pro Tyr Trp Asp
                                                 140            145

GTG CCA CTT GGC CGG AGA GAC TCG CTC GGT G CA AGC ATC CAG GGC TCC       5451
Val Pro Leu Gly Arg Arg Asp Ser Leu Gly A la Ser Ile Gln Gly Ser
         150                 155                 160

AAC AAT GAC ATC CCA GCC CCC AAC AAC ACA C TC CCC ACT ATC ATC ACC       5499
Asn Asn Asp Ile Pro Ala Pro Asn Asn Thr L eu Pro Thr Ile Ile Thr
         165                 170                 175

AAG TTC AAG CGC CAG GGC CTC AAT GTT GTT G AT GTT GTC GCC CTC TCA       5547
Lys Phe Lys Arg Gln Gly Leu Asn Val Val A sp Val Val Ala Leu Ser
         180                 185                 190

GGTGATTTTT CTTGTATTTA TTAGTAACAT CTGTCCTTCG TTATTCACCA A CTTAGCGCA       5607

CACTCATATT ACGCATGGAT ACAATATCAT GTGTGAATAC A GGT GGT  CAC ACC          5660
                                              Gly Gly His Thr
                                                       195

ATT GGT ATG TCT CGG TGC ACT AGT TTC CGG C AG AGG CTA TAC AAC CAG       5708
Ile Gly Met Ser Arg Cys Thr Ser Phe Arg G ln Arg Leu Tyr Asn Gln
         200                 205                 210

ACA GGC AAT GGC ATG GCT GAC AGC ACA CTG G AT GTA TCC TAC GCC GCA       5756
Thr Gly Asn Gly Met Ala Asp Ser Thr Leu A sp Val Ser Tyr Ala Ala
215                 220                 225                 230

AAG CTG AGG CAG GGA TGC CCC CGC TCT GGT G GT GAC AAC AAC CTC TTC       5804
Lys Leu Arg Gln Gly Cys Pro Arg Ser Gly G ly Asp Asn Asn Leu Phe
             235                 240                 245

CCC TTG GAC TTC ATC ACC CCT GCC AAG TTT G AC AAT TTT TAC TAC AAG       5852
Pro Leu Asp Phe Ile Thr Pro Ala Lys Phe A sp Asn Phe Tyr Tyr Lys
         250                 255                 260

AAC CTC CTG GCC GGC AAG GGC CTT CTA AGC T CT GAT GAG ATT CTG TTA       5900
Asn Leu Leu Ala Gly Lys Gly Leu Leu Ser S er Asp Glu Ile Leu Leu
         265                 270                 275
```

```
ACC AAG AGC GCT GAG ACA GCG GCC CTC GTG A AG GCA TAT GCT GCT GAT    5948
Thr Lys Ser Ala Glu Thr Ala Ala Leu Val L ys Ala Tyr Ala Ala Asp
        280                 285                 290

GTC AAT CTC TTC TTC CAG CAC TTT GCA CAG T CT ATG GTG AAT ATG GGA    5996
Val Asn Leu Phe Phe Gln His Phe Ala Gln S er Met Val Asn Met Gly
295             300                 305                 310

AAC ATC TCG CCA CTG ACA GGG TCA CAA GGT G AG ATC AGG AAG AAC TGC    6044
Asn Ile Ser Pro Leu Thr Gly Ser Gln Gly G lu Ile Arg Lys Asn Cys
                315                 320                 325

AGG AGG CTC AAC AAT GAC CAC TGA GGGCACTGAA G TCGCTTGAT GTGCTGAATT    6098
Arg Arg Leu Asn Asn Asp His *
                330

GTTCGTGATG TTGGTGGCGT ATTTTGTTTA AATAAGTAAG CATGGCTGTG A TTTTATCAT    6158

ATGATCGATC TTTGGGGTTT TATTTAACAC ATTGTAAAAT GTGTATCTAT T AATAACTCA    6218

ATGTATAAGA TGTGTTCATT CTTCGGTTGC CATAGATCTG CTTATTTGAC C TGTGATGTT    6278

TTGACTCCAA AAACCAAAAT CACAACTCAA TAAACTCATG GAATATGTCC A CCTGTTTCT    6338

TGAAGAGTTC ATCTACCATT CCAGTTGGCA TTTATCAGTG TTGCAGCGGC G CTGTGCTTT    6398

GTAACATAAC AATTGTTCAC GGCATATATC CAAATCTAGA GGCCTACCAA A ATGAGATAA    6458

CAAGCCAACT AATCTGCTGG GAAATAGGTA ACAAGTCTCT AACAAGATCC G TTGACCTGC    6518

AGGTCGACCT CGAGGGGGGG CCCGGTACCC AA                                  6550

(2) INFORMATION FOR SEQ ID NO:2:

(i) SEQUENCE CHARACTERISTICS:
        (A) LENGTH: 333 am ino acids
        (B) TYPE: amino acid
        (D) TOPOLOGY: linear (ii) MOLECULE TYPE: protein (xi) SEQUENCE DESCRIPTION: SEQ ID NO:2:

Met Ala Thr Ser Met Gly Cys Leu Val Leu L eu Cys Leu Val Ser Ser
 1               5                  10                  15

Leu Leu Pro Ser Ala Val Leu Gly His Pro T rp Gly Gly Leu Phe Pro
                20                  25                  30

Gln Phe Tyr Asp His Ser Cys Pro Lys Ala L ys Glu Ile Val Gln Ser
            35                  40                  45

Ile Val Ala Gln Ala Val Ala Lys Glu Thr A rg Met Ala Ala Ser Leu
        50                  55                  60

Val Arg Leu His Phe His Asp Cys Phe Val L ys Gly Cys Asp Ala Ser
65                  70                  75                  80

Val Leu Leu Asp Asn Ser Ser Ile Val S er Glu Lys Gly Ser Asn
                85                  90                  95

Pro Asn Arg Asn Ser Leu Arg Gly Phe Glu V al Ile Asp Gln Ile Lys
                100                 105                 110

Ala Ala Leu Glu Ala Ala Cys Pro Gly Thr V al Ser Cys Ala Asp Ile
            115                 120                 125

Val Ala Leu Ala Ala Arg Asp Ser Thr Ala L eu Val Gly Gly Pro Tyr
        130                 135                 140

Trp Asp Val Pro Leu Gly Arg Arg Asp Ser L eu Gly Ala Ser Ile Gln
145                 150                 155                 160

Gly Ser Asn Asn Asp Ile Pro Ala Pro Asn A sn Thr Leu Pro Thr Ile
                165                 170                 175

Ile Thr Lys Phe Lys Arg Gln Gly Leu Asn V al Val Asp Val Val Ala
```

-continued

```
               180                 185                 190
Leu Ser Gly Gly His Thr Ile Gly Met Ser Arg Cys Thr Ser Phe Arg
            195                 200                 205
Gln Arg Leu Tyr Asn Gln Thr Gly Asn Gly Met Ala Asp Ser Thr Leu
        210                 215                 220
Asp Val Ser Tyr Ala Ala Lys Leu Arg Gln Gly Cys Pro Arg Ser Gly
225                 230                 235                 240
Gly Asp Asn Asn Leu Phe Pro Leu Asp Phe Ile Thr Pro Ala Lys Phe
                245                 250                 255
Asp Asn Phe Tyr Tyr Lys Asn Leu Leu Ala Gly Lys Gly Leu Leu Ser
            260                 265                 270
Ser Asp Glu Ile Leu Leu Thr Lys Ser Ala Glu Thr Ala Ala Leu Val
        275                 280                 285
Lys Ala Tyr Ala Ala Asp Val Asn Leu Phe Phe Gln His Phe Ala Gln
    290                 295                 300
Ser Met Val Asn Met Gly Asn Ile Ser Pro Leu Thr Gly Ser Gln Gly
305                 310                 315                 320
Glu Ile Arg Lys Asn Cys Arg Arg Leu Asn Asn Asp His
                325                 330
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:3:

TTYCAYGAYT GYTTYGTYAA YGGBTG                              26

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:4:

SGTRTGSGCS CCGSWSAGVG CSAC                                24

(2) INFORMATION FOR SEQ ID NO:5:

(i) SEQUENCE CHARACTERISTICS:
        (A) LENGTH: 1354 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATCAACCAGC AACACTCTTC TCTTATAACA TAGTACAGCG AAGGTAACTC ACATGGCAAC    60

TTCCATGGGT TGTCTCGTCT TGCTCTGCCT TGTTTCTTCT CTCCTTCCCA GTGCCGTCCT   120

TGGCCACCCA TGGGGTGGCT TGTTCCCACA GTTCTATGAC CATTCGTGCC CCAAGGCGAA   180

GGAGATTGTG CAGTCCATTG TGGCACAGGC TGTGGCCAAG GAGACCAGGA TGGCGGCATC   240

```
TTTAGTCAGA CTGCATTTCC ATGACTGCTT TGTCAAGGGC TGCGATGCTT C GGTGCTGTT       300

GGACAACAGC AGCAGCATAG TTAGTGAGAA AGGGTCCAAC CCGAACAGGA A CTCCCTCAG       360

GGGGTTTGAG GTGATCGACC AGATTAAGGC TGCTCTTGAG GCTGCCTGCC C AGGCACAGT       420

CTCCTGTGCC GACATTGTTG CCCTTGCGGC TCGTGATTCC ACCGCCCTGG T TGGTGGACC       480

ATACTGGGAC GTGCCACTTG GCCGGAGAGA CTCGCTCGGT GCAAGCATCC A GGGCTCCAA       540

CAATGACATC CCAGCCCCCA ACAACACACT CCCCACTATC ATCACCAAGT T CAAGCGCCA       600

GGGCCTCAAT GTTGTTGATG TTGTCGCCCT CTCAGGTGGT CACACCATTG G TATGTCTCG       660

GTGCACTAGT TTCCGGCAGA GGCTATACAA CCAGACAGGC AATGGCATGG C TGACAGCAC       720

ACTGGATGTA TCCTACGCCG CAAAGCTGAG GCAGGGATGC CCCCGCTCTG G TGGTGACAA       780

CAACCTCTTC CCCTTGGACT TCATCACCCC TGCCAAGTTT GACAATTTTT A CTACAAGAA       840

CCTCCTGGCC GGCAAGGGCC TTCTAAGCTC TGATGAGATT CTGTTAACCA A GAGCGCTGA       900

GACAGCGGCC CTCGTGAAGG CATATGCTGC TGATGTCAAT CTCTTCTTCC A GCACTTTGC       960

ACAGTCTATG GTGAATATGG GAAACATCTC GCCACTGACA GGGTCACAAG G TGAGATCAG      1020

GAAGAACTGC AGGAGGCTCA ACAATGACCA CTGAGGGCAC TGAAGTCGCT T GATGTGCTG      1080

AATTGTTCGT GATGTTGGTG GCGTATTTTG TTTAAATAAG TAAGCATGGC T GTGATTTTA      1140

TCATATGATC GATCTTTGGG GTTTTATTTA ACACATTGTA AAATGTGTAT C TATTAATAA      1200

CTCAATGTAT AAGATGTGTT CATTCTTCGG TTGCCATAGA TCTGCTTATT T GACCTGTGA      1260

TGTTTTGACT CCAAAAACCA AAATCACAAC TCAATAAACT CATGGAATAT G TCCACCTGT      1320

TTCTTGAAAA AAAAAAAAAA AAAAAAAAAA AAAA                                   1354

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GTCATAGAAC TGTGGG                                                         16

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATAACATAGT ACAGCG                                                         16

(2) INFORMATION FOR SEQ ID NO:8:

(i) SEQUENCE CHARACTERISTICS:
        (A) LENGTH: 10160 base pairs
        (B) TYPE: nucleic acid
        (C) STRANDEDNESS: double
        (D) TOPOLOGY: circular (ii) MOLECULE TYPE: DNA
```

(xi) SEQUENCE DESCRIPTION: SEQ ID NO:8:

```
GGGCCCGCTA GCGGTACCCC CGGGGTCGAC CATGGTCCGT CCTGTAGAAA C CCCAACCCG      60
TGAAATCAAA AAACTCGACG GCCTGTGGGC ATTCAGTCTG GATCGCGAAA A CTGTGGAAT     120
TGATCAGCGT TGGTGGGAAA GCGCGTTACA AGAAAGCCGG GCAATTGCTG T GCCAGGCAG     180
TTTTAACGAT CAGTTCGCCG ATGCAGATAT TCGTAATTAT GCGGGCAACG T CTGGTATCA     240
GCGCGAAGTC TTTATACCGA AAGGTTGGGC AGGCCAGCGT ATCGTGCTGC G TTTCGATGC     300
GGTCACTCAT TACGGCAAAG TGTGGGTCAA TAATCAGGAA GTGATGGAGC A TCAGGGCGG     360
CTATACGCCA TTTGAAGCCG ATGTCACGCC GTATGTTATT GCCGGGAAAA G TGTACGTAT     420
CACCGTTTGT GTGAACAACG AACTGAACTG GCAGACTATC CCGCCGGGAA T GGTGATTAC     480
CGACGAAAAC GGCAAGAAAA AGCAGTCTTA CTTCCATGAT TTCTTTAACT A TGCCGGAAT     540
CCATCGCAGC GTAATGCTCT ACACCACGCC GAACACCTGG GTGGACGATA T CACCGTGGT     600
GACGCATGTC GCGCAAGACT GTAACCACGC GTCTGTTGAC TGGCAGGTGG T GGCCAATGG     660
TGATGTCAGC GTTGAACTGC GTGATGCGGA TCAACAGGTG GTTGCAACTG G ACAAGGCAC     720
TAGCGGGACT TTGCAAGTGG TGAATCCGCA CCTCTGGCAA CCGGGTGAAG G TTATCTCTA     780
TGAACTGTGC GTCACAGCCA AAAGCCAGAC AGAGTGTGAT ATCTACCCGC T TCGCGTCGG     840
CATCCGGTCA GTGGCAGTGA AGGGCGAACA GTTCCTGATT AACCACAAAC C GTTCTACTT     900
TACTGGCTTT GGTCGTCATG AAGATGCGGA CTTACGTGGC AAAGGATTCG A TAACGTGCT     960
GATGGTGCAC GACCACGCAT TAATGGACTG GATTGGGGCC AACTCCTACC G TACCTCGCA    1020
TTACCCTTAC GCTGAAGAGA TGCTCGACTG GGCAGATGAA CATGGCATCG T GGTGATTGA    1080
TGAAACTGCT GCTGTCGGCT TTAACCTCTC TTTAGGCATT GGTTTCGAAG C GGGCAACAA    1140
GCCGAAAGAA CTGTACAGCG AAGAGGCAGT CAACGGGGAA ACTCAGCAAG C GCACTTACA    1200
GGCGATTAAA GAGCTGATAG CGCGTGACAA AAACCACCCA AGCGTGGTGA T GTGGAGTAT    1260
TGCCAACGAA CCGGATACCC GTCCGCAAGT GCACGGGAAT ATTTCGCCAC T GGCGGAAGC    1320
AACGCGTAAA CTCGACCCGA CGCGTCCGAT CACCTGCGTC AATGTAATGT T CTGCGACGC    1380
TCACACCGAT ACCATCAGCG ATCTCTTTGA TGTGCTGTGC CTGAACCGTT A TTACGGATG    1440
GTATGTCCAA AGCGGCGATT TGGAAACGGC AGAGAAGGTA CTGGAAAAAG A ACTTCTGGC    1500
CTGGCAGGAG AAACTGCATC AGCCGATTAT CATCACCGAA TACGGCGTGG A TACGTTAGC    1560
CGGGCTGCAC TCAATGTACA CCGACATGTG GAGTGAAGAG TATCAGTGTG C ATGGCTGGA    1620
TATGTATCAC CGCGTCTTTG ATCGCGTCAG CGCCGTCGTC GGTGAACAGG T ATGGAATTT    1680
CGCCGATTTT GCGACCTCGC AAGGCATATT GCGCGTTGGC GGTAACAAGA A AGGGATCTT    1740
CACTCGCGAC CGCAAACCGA AGTCGGCGGC TTTTCTGCTG CAAAAACGCT G GACTGGCAT    1800
GAACTTCGGT GAAAAACCGC AGCAGGGAGG CAAACAATGA ATCAACAACT C TCCTGGCGC    1860
ACCATCGTCG GCTACAGCCT CGGTGGGGAA TTGGAGCTCG AATTTCCCCG A TCGTTCAAA    1920
CATTTGGCAA TAAAGTTTCT TAAGATTGAA TCCTGTTGCC GGTCTTGCGA T GATTATCAT    1980
ATAATTTCTG TTGAATTACG TTAAGCATGT AATAATTAAC ATGTAATGCA T GACGTTATT    2040
TATGAGATGG GTTTTTATGA TTAGAGTCCC GCAATTATAC ATTTAATACG C GATAGAAAA    2100
CAAAATATAG CGCGCAAACT AGGATAAATT ATCGCGCGCG GTGTCATCTA T GTTACTAGA    2160
TCGATCGGGA ATTAAGCTTA GATCTGCATG GGTGGAGACT TTTCAACAAA G GGTAATATC    2220
CGGAAACCTC CTCGGATTCC ATTGCCCAGC TATCTGTCAC TTTATTGTGA A GATAGTGGA    2280
```

```
AAAGGAAGGT GGCTCCTACA AATGCCATCA TTGCGATAAA GGAAAGGCCA T CGTTGAAGA   2340

TGCCTCTGCC GACAGTGGTC CCAAAGATGG ACCCCCACCC ACGAGGAGCA T CGTGGAAAA   2400

AGAAGACGTT CCAACCACGT CTTCAAAGCA AGTGGATTGA TGTGATCATC G ATGGAGACT   2460

TTTCAACAAA GGGTAATATC CGGAAACCTC CTCGGATTCC ATTGCCCAGC T ATCTGTCAC   2520

TTTATTGTGA AGATAGTGGA AAAGGAAGGT GGCTCCTACA AATGCCATCA T TGCGATAAA   2580

GGAAAGGCCA TCGTTGAAGA TGCCTCTGCC GACAGTGGTC CCAAAGATGG A CCCCCACCC   2640

ACGAGGAGCA TCGTGGAAAA AGAAGACGTT CCAACCACGT CTTCAAAGCA A GTGGATTGA   2700

TGTGATATCT CCACTGACGT AAGGGATGAC GCACAATCCC ACTATCCTTC G CAAGACCCT   2760

TCCTCTATAT AAGGAAGTTC ATTTCATTTG GAGAGAACAC GGGGGACTCT A GAGGATCCA   2820

GCTGAAGGCT CGACAAGGCA GTCCACGGAG GAGCTGATAT TTGGTGGACA A GCTGTGGAT   2880

AGGAGCAACC CTATCCCTAA TATACCAGCA CCACCAAGTC AGGGCAATCC C CAGATCAAG   2940

TGCAAAGGTC CGCCTTGTTT CTCCTCTGTC TCTTGATCTG ACTAATCTTG G TTTATGATT   3000

CGTTGAGTAA TTTTGGGGAA AGCTCCTTTG CTGCTCCACA CATGTCCATT C GAATTTTAC   3060

CGTGTTTAGC AAGGGCGAAA AGTTTGCATC TTGATGATTT AGCTTGACTA T GCGATTGCT   3120

TTCCTGGACC CGTGCAGCTG CGCTCGGATC TGGGGCCATT TGTTCCAGGC A CGGGATAAG   3180

CATTCAGCCA TGGCAGACGC CAAAAACATA AGAAAGGCC CGGCGCCATT C TATCCTCTA   3240

GAGGATGGAA CCGCTGGAGA GCAACTGCAT AAGGCTATGA AGAGATACGC C CTGGTTCCT   3300

GGAACAATTG CTTTTACAGA TGCACATATC GAGGTGAACA TCACGTACGC G GAATACTTC   3360

GAAATGTCCG TTCGGTTGGC AGAAGCTATG AAACGATATG GGCTGAATAC A AATCACAGA   3420

ATCGTCGTAT GCAGTGAAAA CTCTCTTCAA TTCTTTATGC CGGTGTTGGG C GCGTTATTT   3480

ATCGGAGTTG CAGTTGCGCC CGCGAACGAC ATTTATAATG AACGTGAATT G CTCAACAGT   3540

ATGAACATTT CGCAGCCTAC CGTAGTGTTT GTTTCCAAAA AGGGGTTGCA A AAAATTTTG   3600

AACGTGCAAA AAAAATTACC AATAATCCAG AAAATTATTA TCATGGATTC T AAAACGGAT   3660

TACCAGGGAT TTCAGTCGAT GTACACGTTC GTCACATCTC ATCTACCTCC C GGTTTTAAT   3720

GAATACGATT TTGTACCAGA GTCCTTTGAT CGTGACAAAA CAATTGCACT G ATAATGAAT   3780

TCCTCTGGAT CTACTGGGTT ACCTAAGGGT GTGGCCCTTC CGCATAGAAC T GCCTGCGTC   3840

AGATTCTCGC ATGCCAGAGA TCCTATTTTT GGCAATCAAA TCATTCCGGA T ACTGCGATT   3900

TTAAGTGTTG TTCCATTCCA TCACGGTTTT GGAATGTTTA CTACACTCGG A TATTTGATA   3960

TGTGGATTTC GAGTCGTCTT AATGTATAGA TTTGAAGAAG AGCTGTTTTT A CGATCCCTT   4020

CAGGATTACA AAATTCAAAG TGCGTTGCTA GTACCAACCC TATTTTCATT C TTCGCCAAA   4080

AGCACTCTGA TTGACAAATA CGATTTATCT AATTTACACG AAATTGCTTC T GGGGGCGCA   4140

CCTCTTTCGA AAGAAGTCGG GGAAGCGGTT GCAAACGCT TCCATCTTCC A GGGATACGA   4200

CAAGGATATG GGCTCACTGA GACTACATCA GCTATTCTGA TTACACCCGA G GGGATGAT   4260

AAACCGGGCG CGGTCGGTAA AGTTGTTCCA TTTTTTGAAG CGAAGGTTGT G GATCTGGAT   4320

ACCGGGAAAA CGCTGGGCGT TAATCAGAGA GGCGAATTAT GTGTCAGAGG A CCTATGATT   4380

ATGTCCGGTT ATGTAAACAA TCCGGAAGCG ACCAACGCCT TGATTGACAA G GATGGATGG   4440

CTACATTCTG GAGACATAGC TTACTGGGAC GAAGACGAAC ACTTCTTCAT A GTTGACCGC   4500

TTGAAGTCTT TAATTAAATA CAAAGGATAT CAGGTGGCCC CCGCTGAATT G AATCGATA   4560

TTGTTACAAC ACCCCAACAT CTTCGACGCG GGCGTGGCAG GTCTTCCCGA C GATGACGCC   4620

GGTGAACTTC CCGCCGCCGT TGTTGTTTTG GAGCACGGAA AGACGATGAC G GAAAAAGAG   4680
```

-continued

```
ATCGTGGATT ACGTCGCCAG TCAAGTAACA ACCGCGAAAA AGTTGCGCGG A GGAGTTGTG    4740

TTTGTGGACG AAGTACCGAA AGGTCTTACC GGAAAACTCG ACGCAAGAAA A ATCAGAGAG    4800

ATCCTCATAA AGGCCAAGAA GGGCGGAAAG TCCAAATTGT AAAATGTAAC T GTATTCAGC    4860

GATGACGAAA TTCTTAGCTA TTGTAATCAG ATCCGCGAAT TCCCCGATC G TTCAAACAT    4920

TTGGCAATAA AGTTTCTTAA GATTGAATCC TGTTGCCGGT CTTGCGATGA T TATCATATA    4980

ATTTCTGTTG AATTACGTTA AGCATGTAAT AATTAACATG TAATGCATGA C GTTATTTAT    5040

GAGATGGGTT TTTATGATTA GAGTCCCGCA ATTATACATT TAATACGCGA T AGAAAACAA    5100

AATATAGCGC GCAAACTAGG ATAAATTATC GCGCGCGGTG TCATCTATGT T ACTAGATCG    5160

ATCGGGAATT GAGATCTCAT ATGTCGAGCT CGGGGATCTC CTTTGCCCCA G AGATCACAA    5220

TGGACGACTT CCTCTATCTC TACGATCTAG TCAGGAAGTT CGACGGAGAA G GTGACGATA    5280

CCATGTTCAC CACTGATAAT GAGAAGATTA GCCTTTTCAA TTTCAGAAAG A ATGCTAACC    5340

CACAGATGGT TAGAGAGGCT TACGCAGCAG GTCTCATCAA GACGATCTAC C CGAGCAATA    5400

ATCTCCAGGA GATCAAATAC CTTCCCAAGA AGGTTAAAGA TGCAGTCAAA A GATTCAGGA    5460

CTAACTGCAT CAAGAACACA GAGAAAGATA TATTTCTCAA GATCAGAAGT A CTATTCCAG    5520

TATGGACGAT TCAAGGCTTG CTTCACAAAC CAAGGCAAGT AATAGAGATT G GAGTCTCTA    5580

AAAAGGTAGT TCCCACTGAA TCAAAGGCCA TGGAGTCAAA GATTCAAATA G AGGACCTAA    5640

CAGAACTCGC CGTAAAGACT GGCGAACAGT TCCATCGATG ATTGAGACTT T TCAACAAAG    5700

GGTAATATCC GGAAACCTCC TCGGATTCCA TTGCCCAGCT ATCTGTCACT T TATTGTGAA    5760

GATAGTGGAA AAGGAAGGTG GCTCCTACAA ATGCCATCAT TGCGATAAAG G AAAGGCCAT    5820

CGTTGAAGAT GCCTCTGCCG ACAGTGGTCC CAAAGATGGA CCCCCACCCA C GAGGAGCAT    5880

CGTGGAAAAA GAAGACGTTC CAACCACGTC TTCAAAGCAA GTGGATTGAT G TGATATCTC    5940

CACTGACGTA AGGGATGACG CACAATCCCA CTATCCTTCG CAAGACCCTT C CTCTATATA    6000

AGGAAGTTCA TTTCATTTGG AGAGGACACG CTGACAAGCT CGGATCCTTT A GCATGATTG    6060

AACAAGATGG ATTGCACGCA GGTTCTCCGG CCGCTTGGGT GGAGAGGCTA T TCGGCTATG    6120

ACTGGGCACA ACAGACAATC GGCTGCTCTG ATGCCGCCGT GTTCCGGCTG T CAGCGCAGG    6180

GGCGCCCGGT TCTTTTTGTC AAGACCGACC TGTCCGGTGC CCTGAATGAA C TGCAGGACG    6240

AGGCAGCGCG GCTATCGTGG CTGGCCACGA CGGGCGTTCC TTGCGCAGCT G TGCTCGACG    6300

TTGTCACTGA AGCGGGAAGG GACTGGCTGC TATTGGGCGA AGTGCCGGGG C AGGATCTCC    6360

TGTCATCTCA CCTTGCTCCT GCCGAGAAAG TATCCATCAT GGCTGATGCA A TGCGGCGGC    6420

TGCATACGCT TGATCCGGCT ACCTGCCCAT TCGACCACCA AGCGAAACAT C GCATCGAGC    6480

GAGCACGTAC TCGGATGGAA GCCGGTCTTG TCGATCAGGA TGATCTGGAC G AAGAGCATC    6540

AGGGGCTCGC GCCAGCCGAA CTGTTCGCCA GGCTCAAGGC GCGCATGCCC G ACGGCGAGG    6600

ATCTCGTCGT GACCCATGGC GATGCCTGCT TGCCGAATAT CATGGTGGAA A ATGGCCGCT    6660

TTTCTGGATT CATCGACTGT GGCCGGCTGG GTGTGGCGGA CCGCTATCAG G ACATAGCGT    6720

TGGCTACCCG TGATATTGCT GAAGAGCTTG GCGGCGAATG GGCTGACCGC T TCCTCGTGC    6780

TTTACGGTAT CGCCGCTCCC GATTCGCAGC GCATCGCCTT CTATCGCCTT C TTGACGAGT    6840

TCTTCTGAGC GGGACTCTGG GGTTCGAAAT GACCGACCAA GCGACGCCCA A CCTGCCATC    6900

ACGAGATTTC GATTCCACCG CCGCCTTCTA TGAAAGGTTG GCTTCGGAA T CGTTTTCCG    6960

GGACGCCGGC TGGATGATCC TCCAGCGCGG GGATCTCATG CTGGAGTTCT T CGCCCACCC    7020
```

-continued

| | | | | |
|---|---|---|---|---|
| CAACAGAGGT | GGATGGACAG | ACCCGTTCTT | ACACCGGACT | GGGCGCGGGA T AGGATATTC | 7080 |
| AGATTGGGAT | GGGATTGAGC | TTAAAGCCGG | CGCTGAGACC | ATGCTCAAGG T AGGCAATGT | 7140 |
| CCTCAGCGTC | GAGCCCGGCA | TCTATGTCGA | GGGCATTGGT | GGAGCGCGCT T CGGGGATAC | 7200 |
| CGTGCTTGTA | ACTGAGACCG | GATATGAGGC | CCTCACTCCG | CTTGATCTTG G CAAAGATAT | 7260 |
| TTGACGCATT | TATTAGTATG | TGTTAATTTT | CATTTGCAGT | GCAGTATTTT C TATTCGATC | 7320 |
| TTTATGTAAT | TCGTTACAAT | TAATAAATAT | TCAAATCAGA | TTATTGACTG T CATTTGTAT | 7380 |
| CAAATCGTGT | TTAATGGATA | TTTTTATTAT | AATATTGATG | ATATCTCAAT C AAAACGTAG | 7440 |
| ATAATAATAA | TATTTATTTA | ATATTTTTGC | GTCGCACAGT | GAAAATCTAT A TGAGATTAC | 7500 |
| AAAATACCGA | CAACATTATT | TAAGATACAT | AGACATTAAC | CCTGAGACTG T TGGACATCA | 7560 |
| ACGGGTAGAT | TCCTTCATGC | ATAGCACCTC | ATTCTTGGGG | ACAAAAGCAC G GTTTGGCCG | 7620 |
| TTCCATTGCT | GCACGAACGA | GCTTTGCTAT | ATCCTCGGGT | TGGATCATCT C ATCAGGTCC | 7680 |
| AATCAAATTT | GTCCAAGAAC | TCATGTTAGT | CGCAACGAAA | CCGGGCATA T GGTGCACTC | 7740 |
| TCAGTACAAT | CTGCTCTGAT | GCCGCATAGT | TAAGCCAGCC | CCGACACCCG C CAACACCCG | 7800 |
| CTGACGCGCC | CTGACGGGCT | TGTCTGCTCC | CGGCATCCGC | TTACAGACAA G CTGTGACCG | 7860 |
| TCTCCGGGAG | CTGCATGTGT | CAGAGGTTTT | CACCGTCATC | ACCGAAACGC G CGAGACGAA | 7920 |
| AGGGCCTCGT | GATACGCCTA | TTTTTATAGG | TTAATGTCAT | GATAATAATG G TTTCTTAGA | 7980 |
| CGTCAGGTGG | CACTTTTCGG | GGAAATGTGC | GCGGAACCCC | TATTTGTTTA T TTTTCTAAA | 8040 |
| TACATTCAAA | TATGTATCCG | CTCATGAGAC | AATAACCCTG | ATAAATGCTT C AATAATATT | 8100 |
| GAAAAAGGAA | GAGTATGAGT | ATTCAACATT | TCCGTGTCGC | CCTTATTCCC T TTTTTGCGG | 8160 |
| CATTTTGCCT | TCCTGTTTTT | GCTCACCCAG | AAACGCTGGT | GAAAGTAAAA G ATGCTGAAG | 8220 |
| ATCAGTTGGG | TGCACGAGTG | GGTTACATCG | AACTGGATCT | CAACAGCGGT A AGATCCTTG | 8280 |
| AGAGTTTTCG | CCCCGAAGAA | CGTTTTCCAA | TGATGAGCAC | TTTTAAAGTT C TGCTATGTG | 8340 |
| GCGCGGTATT | ATCCCGTATT | GACGCCGGGC | AAGAGCAACT | CGGTCGCCGC A TACACTATT | 8400 |
| CTCAGAATGA | CTTGGTTGAG | TACTCACCAG | TCACAGAAAA | GCATCTTACG G ATGGCATGA | 8460 |
| CAGTAAGAGA | ATTATGCAGT | GCTGCCATAA | CCATGAGTGA | TAACACTGCG G CCAACTTAC | 8520 |
| TTCTGACAAC | GATCGGAGGA | CCGAAGGAGC | TAACCGCTTT | TTTGCACAAC A TGGGGATC | 8580 |
| ATGTAACTCG | CCTTGATCGT | TGGGAACCGG | AGCTGAATGA | AGCCATACCA A ACGACGAGC | 8640 |
| GTGACACCAC | GATGCCTGTA | GCAATGGCAA | CAACGTTGCG | CAAACTATTA A CTGGCGAAC | 8700 |
| TACTTACTCT | AGCTTCCCGG | CAACAATTAA | TAGACTGGAT | GGAGGCGGAT A AAGTTGCAG | 8760 |
| GACCACTTCT | GCGCTCGGCC | CTTCCGGCTG | GCTGGTTTAT | TGCTGATAAA T CTGGAGCCG | 8820 |
| GTGAGCGTGG | GTCTCGCGGT | ATCATTGCAG | CACTGGGGCC | AGATGGTAAG C CCTCCCGTA | 8880 |
| TCGTAGTTAT | CTACACGACG | GGGAGTCAGG | CAACTATGGA | TGAACGAAAT A GACAGATCG | 8940 |
| CTGAGATAGG | TGCCTCACTG | ATTAAGCATT | GGTAACTGTC | AGACCAAGTT T ACTCATATA | 9000 |
| TACTTTAGAT | TGATTAAAA | CTTCATTTTT | AATTTAAAAG | GATCTAGGTG A AGATCCTTT | 9060 |
| TTGATAATCT | CATGACCAAA | ATCCCTTAAC | GTGAGTTTTC | GTTCCACTGA G CGTCAGACC | 9120 |
| CCGTAGAAAA | GATCAAAGGA | TCTTCTTGAG | ATCCTTTTTT | TCTGCGCGTA A TCTGCTGCT | 9180 |
| TGCAAACAAA | AAAACCACCG | CTACCAGCGG | TGGTTTGTTT | GCCGGATCAA G AGCTACCAA | 9240 |
| CTCTTTTTCC | GAAGGTAACT | GGCTTCAGCA | GAGCGCAGAT | ACCAAATACT G TCCTTCTAG | 9300 |
| TGTAGCCGTA | GTTAGGCCAC | CACTTCAAGA | ACTCTGTAGC | ACCGCCTACA T ACCTCGCTC | 9360 |
| TGCTAATCCT | GTTACCAGTG | GCTGCTGCCA | GTGGCGATAA | GTCGTGTCTT A CCGGGTTGG | 9420 |

```
ACTCAAGACG ATAGTTACCG GATAAGGCGC AGCGGTCGGG CTGAACGGGG G GTTCGTGCA      9480

CACAGCCCAG CTTGGAGCGA ACGACCTACA CCGAACTGAG ATACCTACAG C GTGAGCATT      9540

GAGAAAGCGC CACGCTTCCC GAAGGGAGAA AGGCGGACAG GTATCCGGTA A GCGGCAGGG      9600

TCGGAACAGG AGAGCGCACG AGGGAGCTTC CAGGGGAAA CGCCTGGTAT C TTTATAGTC       9660

CTGTCGGGTT TCGCCACCTC TGACTTGAGC GTCGATTTTT GTGATGCTCG T CAGGGGGGC      9720

GGAGCCTATG GAAAAACGCC AGCAACGCGG CCTTTTTACG GTTCCTGGCC T TTTGCTGGC      9780

CTTTTGCTCA CATGTTCTTT CCTGCGTTAT CCCCTGATTC TGTGGATAAC C GTATTACCG      9840

CCTTTGAGTG AGCTGATACC GCTCGCCGCA GCCGAACGAC CGAGCGCAGC G AGTCAGTGA      9900

GCGAGGAAGC GGAAGAGCGC CCAATACGCA AACCGCCTCT CCCCGCGCGT T GGCCGATTC      9960

ATTAATGCAG CTGGCACGAC AGGTTTCCCG ACTGGAAAGC GGGCAGTGAG C GCAACGCAA      10020

TTAATGTGAG TTAGCTCACT CATTAGGCAC CCCAGGCTTT ACACTTTATG C TTCCGGCTC      10080

GTATGTTGTG TGGAATTGTG AGCGGATAAC AATTTCACAC AGGAAACAGC T ATGACCATG      10140

ATTACGCCAA GCTTCCGCGG                                                  10160

(2) INFORMATION FOR SEQ ID NO:9:

(i) SEQUENCE CHARACTERISTICS:
        (A) LENGTH: 11784 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:9:

GGGCCCACCA CTGTTGTAAC TTGTAAGCCA CTAGCTCACG TTCTCCATGA G CTCTTCTCT       60

CTGCTGTTTC TTCCTCTGCT AACTGCGTTA TGATATGACG TCGTATAAAT A ATCTCACAA      120

TACTTCCTTA TTTTCAGCAT GGCCTCTTTT ATGTTTATTT AACAGTAGCA A CCAACGCCG      180

CTCGATGTTT CCTTCAAGAA ACGGCCACTC ACTATGTGGG GTGCAGAAGA A CAAATGTAA      240

GCAGCTCCTA CAGGTACCAG TAGTCATGTC AGTGTGGAAG CTTTCCAACC A ACGCCTCCT      300

TCGAGGAACC TGGTCGTGCT GACATGAATG TAGGCCATGC AAGCACAAGC A CCTAACGCG      360

AATCATCACG ACGCGCCGTG TACTGGGCGT TGGTACATCA CACCCCGCGT T TGACCTGAT      420

CGGAAGCATG CGTGTGTGTT GGCTGCAGGA CCGGCTATAG GTTTCCTGCA T TGGACAGCA      480

GAAGCCAGTC ATGTTAGGCA CTCACGCGCT CCTGCCGTTT GATGAATCAT C CGGTCTTTC      540

GTATTGATCA CTAGTTCACT ACGCTGATAT AGCAAATTTT AAGATGTGAA A CCACGAGAC      600

GAGCGATAAA TCTTAGACGT TACCTATCCA TATGAAGCTT GTGCGAAAAA A AGGCGTGCC      660

GCTGTAGCAT CATTCGTATA CACTTTTGTC CCCAAAGACA GGGATACGAA T CCATGCTCG      720

ACAGAACCCT CCCTTCCCTG CAGATAACGA CACTTAAGTA TAACAAAAGT A GTTGGATTA      780

TTTCAGAAGC AAAATCTCAC TTTTCGCTGG CCTTTTTGTA CTTTGGTTAC T TGAGTTCAG      840

ACAGTGTATG CTATATTGTC ATGTGCTGCG TAAGGTTTAA ATATGGTTCG A CAAATATAT      900

CAGTATATCA CTACTTTGTT ATGGGTGGGG CCTAGCACAA ACTTGATACA G CTAGGATAA      960

AGTTAGAACG ATGACTGATC TACTGTAAAG CGACACCTGT CCTGTTATGG T AGTTAAGT     1020

CCATTCCTGG ACGACTCCAG ATCCAGGATA TGATGCTGTT ACATAATGCG A TTGTTCACA     1080

ATAAAATTGC ATGATGTTCT TCTACTCTTT AGGCAGTTTT GTTCAACAGG C AAGTTGCAT     1140

AATGCATGTG CATATATGAG CAGCATAATC ATCAATTAAT CATAGGTTCG T CATTTTAGT     1200
```

-continued

```
TTCACTCCTT CACATTATTC CAGCCCTTGA AGAAAAATGT AGCAGTGCTT G CTGTTTAAT    1260

AAGTGGCAGA GCTGTTTTCA CTCCACCTAC GCTTGTCTAG GACCAAAATT T TAATCTGTC    1320

ACTTTGAGCT AAAACTGAAG CACCAAACCG CTACAAAAGA ACGTAGGAGC T GAATTGTAA    1380

CTTGATGGGA TTACTATAGC AGTTGCTACA GTTCTAGCTA GCTACCTTAT T CTATACGCA    1440

TCACCCTAAC AACCCGGCTG ACTGCTGCAT CTGACCCCAC CGTCCCTGC T CCAAACCAA     1500

CTCTCCTTTC CTTGCATGCA CTACACCCAC TTCCTGCAGC TATATATACC A CCATATGCC    1560

CATCTTATGA AACCATCCAC AAGAGGAGAA GAAACAATCA ACCAGCAACA C TCTTCTCTT    1620

ATAACATAGT ACAGCGAAGG TAACTCACGT CGACCATGGT CCGTCCTGTA G AAACCCCAA    1680

CCCGTGAAAT CAAAAAACTC GACGGCCTGT GGGCATTCAG TCTGGATCGC G AAAACTGTG    1740

GAATTGATCA GCGTTGGTGG GAAAGCGCGT TACAAGAAAG CCGGGCAATT G CTGTGCCAG    1800

GCAGTTTTAA CGATCAGTTC GCCGATGCAG ATATTCGTAA TTATGCGGGC A ACGTCTGGT    1860

ATCAGCGCGA AGTCTTTATA CCGAAAGGTT GGGCAGGCCA GCGTATCGTG C TGCGTTTCG    1920

ATGCGGTCAC TCATTACGGC AAAGTGTGGG TCAATAATCA GGAAGTGATG G AGCATCAGG    1980

GCGGCTATAC GCCATTTGAA GCCGATGTCA CGCCGTATGT TATTGCCGGG A AAAGTGTAC    2040

GTATCACCGT TTGTGTGAAC AACGAACTGA ACTGGCAGAC TATCCCGCCG G GAATGGTGA    2100

TTACCGACGA AAACGGCAAG AAAAAGCAGT CTTACTTCCA TGATTTCTTT A ACTATGCCG    2160

GAATCCATCG CAGCGTAATG CTCTACACCA CGCCGAACAC CTGGGTGGAC G ATATCACCG    2220

TGGTGACGCA TGTCGCGCAA GACTGTAACC ACGCGTCTGT TGACTGGCAG G TGGTGGCCA    2280

ATGGTGATGT CAGCGTTGAA CTGCGTGATG CGGATCAACA GGTGGTTGCA A CTGGACAAG    2340

GCACTAGCGG GACTTTGCAA GTGGTGAATC CGCACCTCTG GCAACCGGGT G AAGGTTATC    2400

TCTATGAACT GTGCGTCACA GCCAAAAGCC AGACAGAGTG TGATATCTAC C CGCTTCGCG    2460

TCGGCATCCG GTCAGTGGCA GTGAAGGGCG AACAGTTCCT GATTAACCAC A AACCGTTCT    2520

ACTTTACTGG CTTTGGTCGT CATGAAGATG CGGACTTACG TGGCAAAGGA T TCGATAACG    2580

TGCTGATGGT GCACGACCAC GCATTAATGG ACTGGATTGG GGCCAACTCC T ACCGTACCT    2640

CGCATTACCC TTACGCTGAA GAGATGCTCG ACTGGGCAGA TGAACATGGC A TCGTGGTGA    2700

TTGATGAAAC TGCTGCTGTC GGCTTTAACC TCTCTTTAGG CATTGGTTTC G AAGCGGGCA    2760

ACAAGCCGAA AGAACTGTAC AGCGAAGAGG CAGTCAACGG GGAAACTCAG C AAGCGCACT    2820

TACAGGCGAT TAAAGAGCTG ATAGCGCGTG ACAAAAACCA CCCAAGCGTG G TGATGTGGA    2880

GTATTGCCAA CGAACCGGAT ACCCGTCCGC AAGTGCACGG GAATATTTCG C CACTGGCGG    2940

AAGCAACGCG TAAACTCGAC CCGACGCGTC CGATCACCTG CGTCAATGTA A TGTTCTGCG    3000

ACGCTCACAC CGATACCATC AGCGATCTCT TTGATGTGCT GTGCCTGAAC C GTTATTACG    3060

GATGGTATGT CCAAAGCGGC GATTTGGAAA CGGCAGAGAA GGTACTGGAA A AAGAACTTC    3120

TGGCCTGGCA GGAGAAACTG CATCAGCCGA TTATCATCAC CGAATACGGC G TGGATACGT    3180

TAGCCGGGCT GCACTCAATG TACACCGACA TGTGGAGTGA AGAGTATCAG T GTGCATGGC    3240

TGGATATGTA TCACCGCGTC TTTGATCGCG TCAGCGCCGT CGTCGGTGAA C AGGTATGGA    3300

ATTTCGCCGA TTTTGCGACC TCGCAAGGCA TATTGCGCGT TGGCGGTAAC A AGAAAGGGA    3360

TCTTCACTCG CGACCGCAAA CCGAAGTCGG CGGCTTTTCT GCTGCAAAAA C GCTGGACTG    3420

GCATGAACTT CGGTGAAAAA CCGCAGCAGG GAGGCAAACA ATGAATCAAC A ACTCTCCTG    3480

GCGCACCATC GTCGGCTACA GCCTCGGTGG GGAATTGGAG CTCGAATTTC C CCGATCGTT    3540
```

-continued

```
CAAACATTTG GCAATAAAGT TTCTTAAGAT TGAATCCTGT TGCCGGTCTT G CGATGATTA    3600

TCATATAATT TCTGTTGAAT TACGTTAAGC ATGTAATAAT TAACATGTAA T GCATGACGT    3660

TATTTATGAG ATGGGTTTTT ATGATTAGAG TCCCGCAATT ATACATTTAA T ACGCGATAG    3720

AAAACAAAAT ATAGCGCGCA AACTAGGATA AATTATCGCG CGCGGTGTCA T CTATGTTAC    3780

TAGATCGATC GGGAATTAAG CTTAGATCTG CATGGGTGGA GACTTTTCAA C AAAGGGTAA    3840

TATCCGGAAA CCTCCTCGGA TTCCATTGCC CAGCTATCTG TCACTTTATT G TGAAGATAG    3900

TGGAAAAGGA AGGTGGCTCC TACAAATGCC ATCATTGCGA TAAAGGAAAG G CCATCGTTG    3960

AAGATGCCTC TGCCGACAGT GGTCCCAAAG ATGGACCCCC ACCCACGAGG A GCATCGTGG    4020

AAAAAGAAGA CGTTCCAACC ACGTCTTCAA AGCAAGTGGA TTGATGTGAT C ATCGATGGA    4080

GACTTTTCAA CAAAGGGTAA TATCCGAAAA CCTCCTCGGA TTCCATTGCC C AGCTATCTG    4140

TCACTTTATT GTGAAGATAG TGGAAAAGGA AGGTGGCTCC TACAAATGCC A TCATTGCGA    4200

TAAAGGAAAG GCCATCGTTG AAGATGCCTC TGCCGACAGT GGTCCCAAAG A TGGACCCCC    4260

ACCCACGAGG AGCATCGTGG AAAAAGAAGA CGTTCCAACC ACGTCTTCAA A GCAAGTGGA    4320

TTGATGTGAT ATCTCCACTG ACGTAAGGGA TGACGCACAA TCCCACTATC C TTCGCAAGA    4380

CCCTTCCTCT ATATAAGGAA GTTCATTTCA TTTGGAGAGA ACACGGGGGA C TCTAGAGGA    4440

TCCAGCTGAA GGCTCGACAA GGCAGTCCAC GGAGGAGCTG ATATTTGGTG G ACAAGCTGT    4500

GGATAGGAGC AACCCTATCC CTAATATACC AGCACCACCA AGTCAGGGCA A TCCCCAGAT    4560

CAAGTGCAAA GGTCCGCCTT GTTTCTCCTC TGTCTCTTGA TCTGACTAAT C TTGGTTTAT    4620

GATTCGTTGA GTAATTTTGG GGAAAGCTCC TTTGCTGCTC CACACATGTC C ATTCGAATT    4680

TTACCGTGTT TAGCAAGGGC GAAAAGTTTG CATCTTGATG ATTTAGCTTG A CTATGCGAT    4740

TGCTTTCCTG GACCCGTGCA GCTGCGCTCG GATCTGGGGC CATTTGTTCC A GGCACGGGA    4800

TAAGCATTCA GCCATGGCAG ACGCCAAAAA CATAAAGAAA GGCCCGGCGC C ATTCTATCC    4860

TCTAGAGGAT GGAACCGCTG GAGAGCAACT GCATAAGGCT ATGAAGAGAT A CGCCCTGGT    4920

TCCTGGAACA ATTGCTTTTA CAGATGCACA TATCGAGGTG AACATCACGT A CGCGGAATA    4980

CTTCGAAATG TCCGTTCGGT TGGCAGAAGC TATGAAACGA TATGGGCTGA A TACAAATCA    5040

CAGAATCGTC GTATGCAGTG AAAACTCTCT TCAATTCTTT ATGCCGGTGT T GGGCGCGTT    5100

ATTTATCGGA GTTGCAGTTG CGCCCGCGAA CGACATTTAT AATGAACGTG A ATTGCTCAA    5160

CAGTATGAAC ATTTCGCAGC CTACCGTAGT GTTTGTTTCC AAAAAGGGGT T GCAAAAAAT    5220

TTTGAACGTG CAAAAAAAAT TACCAATAAT CCAGAAAATT ATTATCATGG A TTCTAAAAC    5280

GGATTACCAG GGATTTCAGT CGATGTACAC GTTCGTCACA TCTCATCTAC C TCCCGGTTT    5340

TAATGAATAC GATTTTGTAC CAGAGTCCTT TGATCGTGAC AAAACAATTG C ACTGATAAT    5400

GAATTCCTCT GGATCTACTG GGTTACCTAA GGGTGTGGCC CTTCCGCATA G AACTGCCTG    5460

CGTCAGATTC TCGCATGCCA GAGATCCTAT TTTTGGCAAT CAAATCATTC C GGATACTGC    5520

GATTTTAAGT GTTGTTCCAT TCCATCACGG TTTTGGAATG TTTACTACAC T CGGATATTT    5580

GATATGTGGA TTTCGAGTCG TCTTAATGTA TAGATTTGAA GAAGAGCTGT T TTTACGATC    5640

CCTTCAGGAT TACAAAATTC AAAGTGCGTT GCTAGTACCA ACCCTATTTT C ATTCTTCGC    5700

CAAAAGCACT CTGATTGACA AATACGATTT ATCTAATTTA CACGAAATTG C TTCTGGGGG    5760

CGCACCTCTT TCGAAAGAAG TCGGGGAAGC GGTTGCAAAA CGCTTCCATC T TCCAGGGAT    5820

ACGACAAGGA TATGGGCTCA CTGAGACTAC ATCAGCTATT CTGATTACAC C CGAGGGGGA    5880

TGATAAACCG GGCGCGGTCG GTAAAGTTGT TCCATTTTTT GAAGCGAAGG T TGTGGATCT    5940
```

-continued

```
GGATACCGGG AAAACGCTGG GCGTTAATCA GAGAGGCGAA TTATGTGTCA G AGGACCTAT    6000
GATTATGTCC GGTTATGTAA ACAATCCGGA AGCGACCAAC GCCTTGATTG A CAAGGATGG    6060
ATGGCTACAT TCTGGAGACA TAGCTTACTG GGACGAAGAC GAACACTTCT T CATAGTTGA    6120
CCGCTTGAAG TCTTTAATTA AATACAAAGG ATATCAGGTG GCCCCCGCTG A ATTGGAATC    6180
GATATTGTTA CAACACCCCA ACATCTTCGA CGCGGGCGTG GCAGGTCTTC C CGACGATGA    6240
CGCCGGTGAA CTTCCCGCCG CCGTTGTTGT TTTGGAGCAC GGAAAGACGA T GACGGAAAA    6300
AGAGATCGTG GATTACGTCG CCAGTCAAGT AACAACCGCG AAAAAGTTGC G CGGAGGAGT    6360
TGTGTTTGTG GACGAAGTAC CGAAAGGTCT TACCGGAAAA CTCGACGCAA G AAAAATCAG    6420
AGAGATCCTC ATAAAGGCCA AGAAGGGCGG AAAGTCCAAA TTGTAAAATG T AACTGTATT    6480
CAGCGATGAC GAAATTCTTA GCTATTGTAA TCAGATCCGC GAATTTCCCC G ATCGTTCAA    6540
ACATTTGGCA ATAAAGTTTC TTAAGATTGA ATCCTGTTGC CGGTCTTGCG A TGATTATCA    6600
TATAATTTCT GTTGAATTAC GTTAAGCATG TAATAATTAA CATGTAATGC A TGACGTTAT    6660
TTATGAGATG GGTTTTTATG ATTAGAGTCC CGCAATTATA CATTTAATAC G CGATAGAAA    6720
ACAAAATATA GCGCGCAAAC TAGGATAAAT TATCGCGCGC GGTGTCATCT A TGTTACTAG    6780
ATCGATCGGG AATTGAGATC TCATATGTCG AGCTCGGGGA TCTCCTTTGC C CCAGAGATC    6840
ACAATGGACG ACTTCCTCTA TCTCTACGAT CTAGTCAGGA AGTTCGACGG A GAAGGTGAC    6900
GATACCATGT TCACCACTGA TAATGAGAAG ATTAGCCTTT TCAATTTCAG A AAGAATGCT    6960
AACCCACAGA TGGTTAGAGA GGCTTACGCA GCAGGTCTCA TCAAGACGAT C TACCCGAGC    7020
AATAATCTCC AGGAGATCAA ATACCTTCCC AAGAAGGTTA AAGATGCAGT C AAAAGATTC    7080
AGGACTAACT GCATCAAGAA CACAGAGAAA GATATATTTC TCAAGATCAG A AGTACTATT    7140
CCAGTATGGA CGATTCAAGG CTTGCTTCAC AAACCAAGGC AAGTAATAGA G ATTGGAGTC    7200
TCTAAAAAGG TAGTTCCCAC TGAATCAAAG GCCATGGAGT CAAAGATTCA A ATAGAGGAC    7260
CTAACAGAAC TCGCCGTAAA GACTGGCGAA CAGTTCCATC GATGATTGAG A CTTTTCAAC    7320
AAAGGGTAAT ATCCGGAAAC CTCCTCGGAT TCCATTGCCC AGCTATCTGT C ACTTTATTG    7380
TGAAGATAGT GGAAAAGGAA GGTGGCTCCT ACAAATGCCA TCATTGCGAT A AAGGAAAGG    7440
CCATCGTTGA AGATGCCTCT GCCGACAGTG GTCCCAAAGA TGGACCCCCA C CCACGAGGA    7500
GCATCGTGGA AAAAGAAGAC GTTCCAACCA CGTCTTCAAA GCAAGTGGAT T GATGTGATA    7560
TCTCCACTGA CGTAAGGGAT GACGCACAAT CCCACTATCC TTCGCAAGAC C CTTCCTCTA    7620
TATAAGGAAG TTCATTTCAT TTGGAGAGGA CACGCTGACA AGCTCGGATC C TTTAGCATG    7680
ATTGAACAAG ATGGATTGCA CGCAGGTTCT CCGGCCGCTT GGGTGGAGAG G CTATTCGGC    7740
TATGACTGGG CACAACAGAC AATCGGCTGC TCTGATGCCG CCGTGTTCCG G CTGTCAGCG    7800
CAGGGGCGCC CGGTTCTTTT TGTCAAGACC GACCTGTCCG GTGCCCTGAA T GAACTGCAG    7860
GACGAGGCAG CGCGGCTATC GTGGCTGGCC ACGACGGGCG TTCCTTGCGC A GCTGTGCTC    7920
GACGTTGTCA CTGAAGCGGG AAGGGACTGG CTGCTATTGG GCGAAGTGCC G GGCAGGAT    7980
CTCCTGTCAT CTCACCTTGC TCCTGCCGAG AAAGTATCCA TCATGGCTGA T GCAATGCGG    8040
CGGCTGCATA CGCTTGATCC GGCTACCTGC CCATTCGACC ACCAAGCGAA A CATCGCATC    8100
GAGCGAGCAC GTACTCGGAT GGAAGCCGGT CTTGTCGATC AGGATGATCT G GACGAAGAG    8160
CATCAGGGGC TCGCGCCAGC CGAACTGTTC GCCAGGCTCA AGGCGCGCAT G CCCGACGGC    8220
GAGGATCTCG TCGTGACCCA TGGCGATGCC TGCTTGCCGA ATATCATGGT G GAAAATGGC    8280
```

```
CGCTTTTCTG GATTCATCGA CTGTGGCCGG CTGGGTGTGG CGGACCGCTA T CAGGACATA    8340
GCGTTGGCTA CCCGTGATAT TGCTGAAGAG CTTGGCGGCG AATGGGCTGA C CGCTTCCTC    8400
GTGCTTTACG GTATCGCCGC TCCCGATTCG CAGCGCATCG CCTTCTATCG C CTTCTTGAC    8460
GAGTTCTTCT GAGCGGGACT CTGGGGTTCG AAATGACCGA CCAAGCGACG C CCAACCTGC    8520
CATCACGAGA TTTCGATTCC ACCGCCGCCT TCTATGAAAG GTTGGGCTTC G GAATCGTTT    8580
TCCGGGACGC CGGCTGGATG ATCCTCCAGC GCGGGGATCT CATGCTGGAG T TCTTCGCCC    8640
ACCCCAACAG AGGTGGATGG ACAGACCCGT TCTTACACCG GACTGGGCGC G GGATAGGAT    8700
ATTCAGATTG GGATGGGATT GAGCTTAAAG CCGGCGCTGA GACCATGCTC A AGGTAGGCA    8760
ATGTCCTCAG CGTCGAGCCC GGCATCTATG TCGAGGGCAT TGGTGGAGCG C GCTTCGGGG    8820
ATACCGTGCT TGTAACTGAG ACCGGATATG AGGCCCTCAC TCCGCTTGAT C TTGGCAAAG    8880
ATATTTGACG CATTTATTAG TATGTGTTAA TTTTCATTTG CAGTGCAGTA T TTTCTATTC    8940
GATCTTTATG TAATTCGTTA CAATTAATAA ATATTCAAAT CAGATTATTG A CTGTCATTT    9000
GTATCAAATC GTGTTTAATG GATATTTTTA TTATAATATT GATGATATCT C AATCAAAAC    9060
GTAGATAATA ATAATATTTA TTTAATATTT TTGCGTCGCA CAGTGAAAAT C TATATGAGA    9120
TTACAAAATA CCGACAACAT TATTTAAGAT ACATAGACAT TAACCCTGAG A CTGTTGGAC    9180
ATCAACGGGT AGATTCCTTC ATGCATAGCA CCTCATTCTT GGGGACAAAA G CACGGTTTG    9240
GCCGTTCCAT TGCTGCACGA ACGAGCTTTG CTATATCCTC GGGTTGGATC A TCTCATCAG    9300
GTCCAATCAA ATTTGTCCAA GAACTCATGT TAGTCGCAAC GAAACCGGGG C ATATGGTGC    9360
ACTCTCAGTA CAATCTGCTC TGATGCCGCA TAGTTAAGCC AGCCCCGACA C CCGCCAACA    9420
CCCGCTGACG CGCCCTGACG GGCTTGTCTG CTCCCGGCAT CCGCTTACAG A CAAGCTGTG    9480
ACCGTCTCCG GGAGCTGCAT GTGTCAGAGG TTTTCACCGT CATCACCGAA A CGCGCGAGA    9540
CGAAAGGGCC TCGTGATACG CCTATTTTTA TAGGTTAATG TCATGATAAT A ATGGTTTCT    9600
TAGACGTCAG GTGGCACTTT TCGGGGAAAT GTGCGCGGAA CCCCTATTTG T TTATTTTTC    9660
TAAATACATT CAAATATGTA TCCGCTCATG AGACAATAAC CCTGATAAAT G CTTCAATAA    9720
TATTGAAAAA GGAAGAGTAT GAGTATTCAA CATTTCCGTG TCGCCCTTAT T CCCTTTTTT    9780
GCGGCATTTT GCCTTCCTGT TTTTGCTCAC CCAGAAACGC TGGTGAAAGT A AAAGATGCT    9840
GAAGATCAGT TGGGTGCACG AGTGGGTTAC ATCGAACTGG ATCTCAACAG C GGTAAGATC    9900
CTTGAGAGTT TTCGCCCCGA AGAACGTTTT CCAATGATGA GCACTTTTAA A GTTCTGCTA    9960
TGTGGCGCGG TATTATCCCG TATTGACGCC GGGCAAGAGC AACTCGGTCG C CGCATACAC   10020
TATTCTCAGA ATGACTTGGT TGAGTACTCA CCAGTCACAG AAAAGCATCT T ACGGATGGC   10080
ATGACAGTAA GAGAATTATG CAGTGCTGCC ATAACCATGA GTGATAACAC T GCGGCCAAC   10140
TTACTTCTGA CAACGATCGG AGGACCGAAG GAGCTAACCG CTTTTTTGCA C AACATGGGG   10200
GATCATGTAA CTCGCCTTGA TCGTTGGGAA CCGGAGCTGA ATGAAGCCAT A CCAAACGAC   10260
GAGCGTGACA CCACGATGCC TGTAGCAATG GCAACAACGT TGCGCAAACT A TTAACTGGC   10320
GAACTACTTA CTCTAGCTTC CCGGCAACAA TTAATAGACT GGATGGAGGC G GATAAAGTT   10380
GCAGGACCAC TTCTGCGCTC GGCCCTTCCG GCTGGCTGGT TTATTGCTGA T AAATCTGGA   10440
GCCGGTGAGC GTGGGTCTCG CGGTATCATT GCAGCACTGG GGCCAGATGG T AAGCCCTCC   10500
CGTATCGTAG TTATCTACAC GACGGGGAGT CAGGCAACTA TGGATGAACG A AATAGACAG   10560
ATCGCTGAGA TAGGTGCCTC ACTGATTAAG CATTGGTAAC TGTCAGACCA A GTTTACTCA   10620
TATATACTTT AGATTGATTT AAAACTTCAT TTTTAATTTA AAAGGATCTA G GTGAAGATC   10680
```

```
CTTTTTGATA ATCTCATGAC CAAAATCCCT TAACGTGAGT TTTCGTTCCA C TGAGCGTCA    10740

GACCCCGTAG AAAAGATCAA AGGATCTTCT TGAGATCCTT TTTTTCTGCG C GTAATCTGC    10800

TGCTTGCAAA CAAAAAAACC ACCGCTACCA GCGGTGGTTT GTTTGCCGGA T CAAGAGCTA    10860

CCAACTCTTT TTCCGAAGGT AACTGGCTTC AGCAGAGCGC AGATACCAAA T ACTGTCCTT    10920

CTAGTGTAGC CGTAGTTAGG CCACCACTTC AAGAACTCTG TAGCACCGCC T ACATACCTC    10980

GCTCTGCTAA TCCTGTTACC AGTGGCTGCT GCCAGTGGCG ATAAGTCGTG T CTTACCGGG    11040

TTGGACTCAA GACGATAGTT ACCGGATAAG GCGCAGCGGT CGGGCTGAAC G GGGGGTTCG    11100

TGCACACAGC CCAGCTTGGA GCGAACGACC TACACCGAAC TGAGATACCT A CAGCGTGAG    11160

CATTGAGAAA GCGCCACGCT TCCCGAAGGG AGAAAGGCGG ACAGGTATCC G GTAAGCGGC    11220

AGGGTCGGAA CAGGAGAGCG CACGAGGGAG CTTCCAGGGG GAAACGCCTG G TATCTTTAT    11280

AGTCCTGTCG GGTTTCGCCA CCTCTGACTT GAGCGTCGAT TTTTGTGATG C TCGTCAGGG    11340

GGGCGGAGCC TATGGAAAAA CGCCAGCAAC GCGGCCTTTT TACGGTTCCT G GCCTTTTGC    11400

TGGCCTTTTG CTCACATGTT CTTTCCTGCG TTATCCCCTG ATTCTGTGGA T AACCGTATT    11460

ACCGCCTTTG AGTGAGCTGA TACCGCTCGC CGCAGCCGAA CGACCGAGCG C AGCGAGTCA    11520

GTGAGCGAGG AAGCGGAAGA GCGCCCAATA CGCAAACCGC CTCTCCCCGC G CGTTGGCCG    11580

ATTCATTAAT GCAGCTGGCA CGACAGGTTT CCCGACTGGA AAGCGGGCAG T GAGCGCAAC    11640

GCAATTAATG TGAGTTAGCT CACTCATTAG GCACCCCAGG CTTTACACTT T ATGCTTCCG    11700

GCTCGTATGT TGTGTGGAAT TGTGAGCGGA TAACAATTTC ACACAGGAAA C AGCTATGAC    11760

CATGATTACG CCAAGCTTCC GCGG                                            11784

(2) INFORMATION FOR SEQ ID NO:10:

(i) SEQUENCE CHARACTERISTICS:
        (A) LENGTH: 11991 base  pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:10:

GGGCCCACCA CTGTTGTAAC TTGTAAGCCA CTAGCTCACG TTCTCCATGA G CTCTTCTCT      60

CTGCTGTTTC TTCCTCTGCT AACTGCGTTA TGATATGACG TCGTATAAAT A ATCTCACAA     120

TACTTCCTTA TTTTCAGCAT GGCCTCTTTT ATGTTTATTT AACAGTAGCA A CCAACGCCG     180

CTCGATGTTT CCTTCAAGAA ACGGCCACTC ACTATGTGGT GTGCAGAAGA A CAAATGTAA     240

GCAGCTCCTA CAGGTACCAG TAGTCATGTC AGTGTGGAAG CTTTCCAACC A ACGCCTCCT     300

TCGAGGAACC TGGTCGTGCT GACATGAATG TAGGCCATGC AAGCACAAGC A CCTAACGCG     360

AATCATCACG ACGCGCCGTG TACTGGGCGT TGGTACATCA CACCCCGCGT T TGACCTGAT     420

CGGAAGCATG CGTGTGTGTT GGCTGCAGGA CCGGCTATAG GTTTCCTGCA T TGGACAGCA     480

GAAGCCAGTC ATGTTAGGCA CTCACGCGCT CCTGCCGTTT GATGAATCAT C CGGTCTTTC     540

GTATTGATCA CTAGTTCACT ACGCTGATAT AGCAAATTTT AAGATGTGAA A CCACGAGAC     600

GAGCGATAAA TCTTAGACGT TACCTATCCA TATGAAGCTT GTGCGAAAAA A AGGCGTGCC     660

GCTGTAGCAT CATTCGTATA CACTTTTGTC CCCAAAGACA GGGATACGAA T CCATGCTCG     720

ACAGAACCCT CCCTTCCCTG CAGATAACGA CACTTAAGTA TAACAAAGT A GTTGGATTA     780

TTTCAGAAGC AAAATCTCAC TTTTCGCTGG CCTTTTTGTA CTTTGGTTAC T TGAGTTCAG     840
```

-continued

| | |
|---|---|
| ACAGTGTATG CTATATTGTC ATGTGCTGCG TAAGGTTTAA ATATGGTTCG A CAAATATAT | 900 |
| CAGTATATCA CTACTTTGTT ATGGGTGGGG CCTAGCACAA ACTTGATACA G CTAGGATAA | 960 |
| AGTTAGAACG ATGACTGATC TACTGTAAAG CGACACCTGT CCTGTTATGG T AGTTTAAGT | 1020 |
| CCATTCCTGG ACGACTCCAG ATCCAGGATA TGATGCTGTT ACATAATGCG A TTGTTCACA | 1080 |
| ATAAAATTGC ATGATGTTCT TCTACTCTTT AGGCAGTTTT GTTCAACAGG C AAGTTGCAT | 1140 |
| AATGCATGTG CATATATGAG CAGCATAATC ATCAATTAAT CATAGGTTCG T CATTTTAGT | 1200 |
| TTCACTCCTT CACATTATTC CAGCCCTTGA AGAAAAATGT AGCAGTGCTT G CTGTTTAAT | 1260 |
| AAGTGGCAGA GCTGTTTTCA CTCCACCTAC GCTTGTCTAG GACCAAAATT T TAATCTGTC | 1320 |
| ACTTTGAGCT AAAACTGAAG CACCAAACCG CTACAAAAGA ACGTAGGAGC T GAATTGTAA | 1380 |
| CTTGATGGGA TTACTATAGC AGTTGCTACA GTTCTAGCTA GCTACCTTAT T CTATACGCA | 1440 |
| TCACCCTAAC AACCCGGCTG ACTGCTGCAT CTGACCCCAC CGTCCCCTGC T CCAAACCAA | 1500 |
| CTCTCCTTTC CTTGCATGCA CTACACCCAC TTCCTGCAGC TATATATACC A CCATATGCC | 1560 |
| CATCTTATGA AACCATCCAC AAGAGGAGAA GAAACAATCA ACCAGCAACA C TCTTCTCTT | 1620 |
| ATAACATAGT ACAGCGAAGG TAACTCACAG TGCAAAGGTC CGCCTTGTTT C TCCTCTGTC | 1680 |
| TCTTGATCTG ACTAATCTTG GTTTATGATT CGTTGAGTAA TTTTGGGGAA A GCTCCTTTG | 1740 |
| CTGCTCCACA CATGTCCATT CGAATTTTAC CGTGTTTAGC AAGGGCGAAA A GTTTGCATC | 1800 |
| TTGATGATTT AGCTTGACTA TGCGATTGCT TTCCTGGACC CGTGCAGCTG C GCTCGTCGA | 1860 |
| CCATGGTCCG TCCTGTAGAA ACCCCAACCC GTGAAATCAA AAAACTCGAC G GCCTGTGGG | 1920 |
| CATTCAGTCT GGATCGCGAA AACTGTGGAA TTGATCAGCG TTGGTGGGAA A GCGCGTTAC | 1980 |
| AAGAAAGCCG GGCAATTGCT GTGCCAGGCA GTTTTAACGA TCAGTTCGCC G ATGCAGATA | 2040 |
| TTCGTAATTA TGCGGGCAAC GTCTGGTATC AGCGCGAAGT CTTTATACCG A AAGGTTGGG | 2100 |
| CAGGCCAGCG TATCGTGCTG CGTTTCGATG CGGTCACTCA TTACGGCAAA G TGTGGGTCA | 2160 |
| ATAATCAGGA AGTGATGGAG CATCAGGGCG GCTATACGCC ATTTGAAGCC G ATGTCACGC | 2220 |
| CGTATGTTAT TGCCGGGAAA AGTGTACGTA TCACCGTTTG TGTGAACAAC G AACTGAACT | 2280 |
| GGCAGACTAT CCCGCCGGGA ATGGTGATTA CCGACGAAAA CGGCAAGAAA A AGCAGTCTT | 2340 |
| ACTTCCATGA TTTCTTTAAC TATGCCGGAA TCCATCGCAG CGTAATGCTC T ACACCACGC | 2400 |
| CGAACACCTG GGTGGACGAT ATCACCGTGG TGACGCATGT CGCGCAAGAC T GTAACCACG | 2460 |
| CGTCTGTTGA CTGGCAGGTG GTGGCCAATG GTGATGTCAG CGTTGAACTG C GTGATGCGG | 2520 |
| ATCAACAGGT GGTTGCAACT GGACAAGGCA CTAGCGGGAC TTTGCAAGTG G TGAATCCGC | 2580 |
| ACCTCTGGCA ACCGGGTGAA GGTTATCTCT ATGAACTGTG CGTCACAGCC A AAAGCCAGA | 2640 |
| CAGAGTGTGA TATCTACCCG CTTCGCGTCG GCATCCGGTC AGTGGCAGTG A AGGGCGAAC | 2700 |
| AGTTCCTGAT TAACCACAAA CCGTTCTACT TTACTGGCTT TGGTCGTCAT G AAGATGCGG | 2760 |
| ACTTACGTGG CAAAGGATTC GATAACGTGC TGATGGTGCA CGACCACGCA T TAATGGACT | 2820 |
| GGATTGGGGC CAACTCCTAC CGTACCTCGC ATTACCCTTA CGCTGAAGAG A TGCTCGACT | 2880 |
| GGGCAGATGA ACATGGCATC GTGGTGATTG ATGAAACTGC TGCTGTCGGC T TTAACCTCT | 2940 |
| CTTTAGGCAT TGGTTTCGAA GCGGGCAACA AGCCGAAAGA ACTGTACAGC G AAGAGGCAG | 3000 |
| TCAACGGGGA AACTCAGCAA GCGCACTTAC AGGCGATTAA AGAGCTGATA G CGCGTGACA | 3060 |
| AAAACCACCC AAGCGTGGTG ATGTGGAGTA TTGCCAACGA ACCGGATACC C GTCCGCAAG | 3120 |
| TGCACGGGAA TATTTCGCCA CTGGCGGAAG CAACGCGTAA ACTCGACCCG A CGCGTCCGA | 3180 |

```
TCACCTGCGT CAATGTAATG TTCTGCGACG CTCACACCGA TACCATCAGC G ATCTCTTTG    3240

ATGTGCTGTG CCTGAACCGT TATTACGGAT GGTATGTCCA AAGCGGCGAT T TGGAAACGG    3300

CAGAGAAGGT ACTGGAAAAA GAACTTCTGG CCTGGCAGGA GAAACTGCAT C AGCCGATTA    3360

TCATCACCGA ATACGGCGTG GATACGTTAG CCGGGCTGCA CTCAATGTAC A CCGACATGT    3420

GGAGTGAAGA GTATCAGTGT GCATGGCTGG ATATGTATCA CCGCGTCTTT G ATCGCGTCA    3480

GCGCCGTCGT CGGTGAACAG GTATGGAATT CGCCGATTT TGCGACCTCG C AAGGCATAT    3540

TGCGCGTTGG CGGTAACAAG AAAGGGATCT TCACTCGCGA CCGCAAACCG A AGTCGGCGG    3600

CTTTTCTGCT GCAAAAACGC TGGACTGGCA TGAACTTCGG TGAAAAACCG C AGCAGGGAG    3660

GCAAACAATG AATCAACAAC TCTCCTGGCG CACCATCGTC GGCTACAGCC T CGGTGGGGA    3720

ATTGGAGCTC GAATTCCCC GATCGTTCAA ACATTTGGCA ATAAAGTTTC T TAAGATTGA    3780

ATCCTGTTGC CGGTCTTGCG ATGATTATCA TATAATTTCT GTTGAATTAC G TTAAGCATG    3840

TAATAATTAA CATGTAATGC ATGACGTTAT TTATGAGATG GGTTTTTATG A TTAGAGTCC    3900

CGCAATTATA CATTTAATAC GCGATAGAAA ACAAAATATA GCGCGCAAAC T AGGATAAAT    3960

TATCGCGCGC GGTGTCATCT ATGTTACTAG ATCGATCGGG AATTAAGCTT A GATCTGCAT    4020

GGGTGGAGAC TTTTCAACAA AGGGTAATAT CCGGAAACCT CCTCGGATTC C ATTGCCCAG    4080

CTATCTGTCA CTTTATTGTG AAGATAGTGG AAAAGGAAGG TGGCTCCTAC A AATGCCATC    4140

ATTGCGATAA AGGAAAGGCC ATCGTTGAAG ATGCCTCTGC CGACAGTGGT C CCAAAGATG    4200

GACCCCCACC CACGAGGAGC ATCGTGGAAA AGAAGACGT TCCAACCACG T CTTCAAAGC    4260

AAGTGGATTG ATGTGATCAT CGATGGAGAC TTTTCAACAA AGGGTAATAT C CGGAAACCT    4320

CCTCGGATTC CATTGCCCAG CTATCTGTCA CTTTATTGTG AAGATAGTGG A AAAGGAAGG    4380

TGGCTCCTAC AAATGCCATC ATTGCGATAA AGGAAAGGCC ATCGTTGAAG A TGCCTCTGC    4440

CGACAGTGGT CCCAAAGATG GACCCCCACC CACGAGGAGC ATCGTGGAAA A AGAAGACGT    4500

TCCAACCACG TCTTCAAAGC AAGTGGATTG ATGTGATATC TCCACTGACG T AAGGGATGA    4560

CGCACAATCC CACTATCCTT CGCAAGACCC TTCCTCTATA TAAGGAAGTT C ATTTCATTT    4620

GGAGAGAACA CGGGGGACTC TAGAGGATCC AGCTGAAGGC TCGACAAGGC A GTCCACGGA    4680

GGAGCTGATA TTTGGTGGAC AAGCTGTGGA TAGGAGCAAC CCTATCCCTA A TATACCAGC    4740

ACCACCAAGT CAGGGCAATC CCCAGATCAA GTGCAAAGGT CCGCCTTGTT T CTCCTCTGT    4800

CTCTTGATCT GACTAATCTT GGTTTATGAT TCGTTGAGTA ATTTTGGGGA A AGCTCCTTT    4860

GCTGCTCCAC ACATGTCCAT TCGAATTTTA CCGTGTTTAG CAAGGGCGAA A AGTTTGCAT    4920

CTTGATGATT TAGCTTGACT ATGCGATTGC TTTCCTGGAC CCGTGCAGCT G CGCTCGGAT    4980

CTGGGGCCAT TTGTTCCAGG CACGGGATAA GCATTCAGCC ATGGCAGACG C CAAAAACAT    5040

AAAGAAAGGC CCGGCGCCAT TCTATCCTCT AGAGGATGGA ACCGCTGGAG A GCAACTGCA    5100

TAAGGCTATG AAGAGATACG CCCTGGTTCC TGGAACAATT GCTTTTACAG A TGCACATAT    5160

CGAGGTGAAC ATCACGTACG CGGAATACTT CGAAATGTCC GTTCGGTTGG C AGAAGCTAT    5220

GAAACGATAT GGGCTGAATA CAAATCACAG AATCGTCGTA TGCAGTGAAA A CTCTCTTCA    5280

ATTCTTTATG CCGGTGTTGG GCGCGTTATT TATCGGAGTT GCAGTTGCGC C CGCGAACGA    5340

CATTTATAAT GAACGTGAAT TGCTCAACAG TATGAACATT TCGCAGCCTA C CGTAGTGTT    5400

TGTTTCCAAA AAGGGGTTGC AAAAAATTTT GAACGTGCAA AAAAAATTAC C AATAATCCA    5460

GAAAATTATT ATCATGGATT CTAAAACGGA TTACCAGGGA TTTCAGTCGA T GTACACGTT    5520

CGTCACATCT CATCTACCTC CCGGTTTTAA TGAATACGAT TTTGTACCAG A GTCCTTTGA    5580
```

```
TCGTGACAAA ACAATTGCAC TGATAATGAA TTCCTCTGGA TCTACTGGGT T ACCTAAGGG    5640

TGTGGCCCTT CCGCATAGAA CTGCCTGCGT CAGATTCTCG CATGCCAGAG A TCCTATTTT    5700

TGGCAATCAA ATCATTCCGG ATACTGCGAT TTTAAGTGTT GTTCCATTCC A TCACGGTTT    5760

TGGAATGTTT ACTACACTCG GATATTTGAT ATGTGGATTT CGAGTCGTCT T AATGTATAG    5820

ATTTGAAGAA GAGCTGTTTT TACGATCCCT TCAGGATTAC AAAATTCAAA G TGCGTTGCT    5880

AGTACCAACC CTATTTTCAT TCTTCGCCAA AAGCACTCTG ATTGACAAAT A CGATTTATC    5940

TAATTTACAC GAAATTGCTT CTGGGGGCGC ACCTCTTTCG AAAGAAGTCG G GGAAGCGGT    6000

TGCAAAACGC TTCCATCTTC CAGGGATACG ACAAGGATAT GGGCTCACTG A GACTACATC    6060

AGCTATTCTG ATTACACCCG AGGGGGATGA TAAACCGGGC GCGGTCGGTA A AGTTGTTCC    6120

ATTTTTTGAA GCGAAGGTTG TGGATCTGGA TACCGGGAAA ACGCTGGGCG T TAATCAGAG    6180

AGGCGAATTA TGTGTCAGAG GACCTATGAT TATGTCCGGT TATGTAAACA A TCCGGAAGC    6240

GACCAACGCC TTGATTGACA AGGATGGATG GCTACATTCT GGAGACATAG C TTACTGGGA    6300

CGAAGACGAA CACTTCTTCA TAGTTGACCG CTTGAAGTCT TTAATTAAAT A CAAGGATA    6360

TCAGGTGGCC CCCGCTGAAT TGGAATCGAT ATTGTTACAA CACCCCAACA T CTTCGACGC    6420

GGGCGTGGCA GGTCTTCCCG ACGATGACGC CGGTGAACTT CCCGCCGCCG T TGTTGTTTT    6480

GGAGCACGGA AAGACGATGA CGGAAAAAGA GATCGTGGAT TACGTCGCCA G TCAAGTAAC    6540

AACCGCGAAA AAGTTGCGCG GAGGAGTTGT GTTTGTGGAC GAAGTACCGA A AGGTCTTAC    6600

CGGAAAACTC GACGCAAGAA AAATCAGAGA GATCCTCATA AAGGCCAAGA A GGGCGGAAA    6660

GTCCAAATTG TAAAATGTAA CTGTATTCAG CGATGACGAA ATTCTTAGCT A TTGTAATCA    6720

GATCCGCGAA TTTCCCCGAT CGTTCAAACA TTTGGCAATA AAGTTTCTTA A GATTGAATC    6780

CTGTTGCCGG TCTTGCGATG ATTATCATAT AATTTCTGTT GAATTACGTT A AGCATGTAA    6840

TAATTAACAT GTAATGCATG ACGTTATTTA TGAGATGGGT TTTTATGATT A GAGTCCCGC    6900

AATTATACAT TTAATACGCG ATAGAAAACA AAATATAGCG CGCAAACTAG G ATAAATTAT    6960

CGCGCGCGGT GTCATCTATG TTACTAGATC GATCGGGAAT TGAGATCTCA T ATGTCGAGC    7020

TCGGGGATCT CCTTTGCCCC AGAGATCACA ATGGACGACT TCCTCTATCT C TACGATCTA    7080

GTCAGGAAGT TCGACGGAGA AGGTGACGAT ACCATGTTCA CCACTGATAA T GAGAAGATT    7140

AGCCTTTTCA ATTTCAGAAA GAATGCTAAC CCACAGATGG TTAGAGAGGC T TACGCAGCA    7200

GGTCTCATCA AGACGATCTA CCCGAGCAAT AATCTCCAGG AGATCAAATA C CTTCCCAAG    7260

AAGGTTAAAG ATGCAGTCAA AGATTCAGG ACTAACTGCA TCAAGAACAC A GAGAAAGAT    7320

ATATTTCTCA AGATCAGAAG TACTATTCCA GTATGGACGA TTCAAGGCTT G CTTCACAAA    7380

CCAAGGCAAG TAATAGAGAT TGGAGTCTCT AAAAAGGTAG TTCCCACTGA A TCAAAGGCC    7440

ATGGAGTCAA AGATTCAAAT AGAGGACCTA ACAGAACTCG CCGTAAAGAC T GGCGAACAG    7500

TTCCATCGAT GATTGAGACT TTTCAACAAA GGGTAATATC CGGAAACCTC C TCGGATTCC    7560

ATTGCCCAGC TATCTGTCAC TTTATTGTGA AGATAGTGGA AAAGGAAGGT G GCTCCTACA    7620

AATGCCATCA TTGCGATAAA GGAAAGGCCA TCGTTGAAGA TGCCTCTGCC G ACAGTGGTC    7680

CCAAAGATGG ACCCCCACCC ACGAGGAGCA TCGTGGAAAA AGAAGACGTT C CAACCACGT    7740

CTTCAAAGCA AGTGGATTGA TGTGATATCT CCACTGACGT AAGGGATGAC G CACAATCCC    7800

ACTATCCTTC GCAAGACCCT TCCTCTATAT AAGGAAGTTC ATTTCATTTG G AGAGGACAC    7860

GCTGACAAGC TCGGATCCTT TAGCATGATT GAACAAGATG GATTGCACGC A GGTTCTCCG    7920
```

```
GCCGCTTGGG TGGAGAGGCT ATTCGGCTAT GACTGGGCAC AACAGACAAT C GGCTGCTCT    7980

GATGCCGCCG TGTTCCGGCT GTCAGCGCAG GGGCGCCCGG TTCTTTTTGT C AAGACCGAC    8040

CTGTCCGGTG CCCTGAATGA ACTGCAGGAC GAGGCAGCGC GGCTATCGTG G CTGGCCACG    8100

ACGGGCGTTC CTTGCGCAGC TGTGCTCGAC GTTGTCACTG AAGCGGGAAG G GACTGGCTG    8160

CTATTGGGCG AAGTGCCGGG GCAGGATCTC CTGTCATCTC ACCTTGCTCC T GCCGAGAAA    8220

GTATCCATCA TGGCTGATGC AATGCGGCGG CTGCATACGC TTGATCCGGC T ACCTGCCCA    8280

TTCGACCACC AAGCGAAACA TCGCATCGAG CGAGCACGTA CTCGGATGGA A GCCGGTCTT    8340

GTCGATCAGG ATGATCTGGA CGAAGAGCAT CAGGGGCTCG CGCCAGCCGA A CTGTTCGCC    8400

AGGCTCAAGG CGCGCATGCC CGACGGCGAG GATCTCGTCG TGACCCATGG C GATGCCTGC    8460

TTGCCGAATA TCATGGTGGA AAATGGCCGC TTTTCTGGAT TCATCGACTG T GGCCGGCTG    8520

GGTGTGGCGG ACCGCTATCA GGACATAGCG TTGGCTACCC GTGATATTGC T GAAGAGCTT    8580

GGCGGCGAAT GGGCTGACCG CTTCCTCGTG CTTTACGGTA TCGCCGCTCC C GATTCGCAG    8640

CGCATCGCCT TCTATCGCCT TCTTGACGAG TTCTTCTGAG CGGGACTCTG G GGTTCGAAA    8700

TGACCGACCA AGCGACGCCC AACCTGCCAT CACGAGATTT CGATTCCACC G CCGCCTTCT    8760

ATGAAAGGTT GGGCTTCGGA ATCGTTTTCC GGGACGCCGG CTGGATGATC C TCCAGCGCG    8820

GGGATCTCAT GCTGGAGTTC TTCGCCCACC CCAACAGAGG TGGATGGACA G ACCCGTTCT    8880

TACACCGGAC TGGGCGCGGG ATAGGATATT CAGATTGGGA TGGGATTGAG C TTAAAGCCG    8940

GCGCTGAGAC CATGCTCAAG GTAGGCAATG TCCTCAGCGT CGAGCCCGGC A TCTATGTCG    9000

AGGGCATTGG TGGAGCGCGC TTCGGGGATA CCGTGCTTGT AACTGAGACC G GATATGAGG    9060

CCCTCACTCC GCTTGATCTT GGCAAAGATA TTTGACGCAT TTATTAGTAT G TGTTAATTT    9120

TCATTTGCAG TGCAGTATTT TCTATTCGAT CTTTATGTAA TTCGTTACAA T TAATAAATA    9180

TTCAAATCAG ATTATTGACT GTCATTTGTA TCAAATCGTG TTTAATGGAT A TTTTTATTA    9240

TAATATTGAT GATATCTCAA TCAAAACGTA GATAATAATA ATATTTATTT A ATATTTTTG    9300

CGTCGCACAG TGAAAATCTA TATGAGATTA CAAAATACCG ACAACATTAT T TAAGATACA    9360

TAGACATTAA CCCTGAGACT GTTGGACATC AACGGGTAGA TTCCTTCATG C ATAGCACCT    9420

CATTCTTGGG GACAAAAGCA CGGTTTGGCC GTTCCATTGC TGCACGAACG A GCTTTGCTA    9480

TATCCTCGGG TTGGATCATC TCATCAGGTC CAATCAAATT TGTCCAAGAA C TCATGTTAG    9540

TCGCAACGAA ACCGGGGCAT ATGGTGCACT CTCAGTACAA TCTGCTCTGA T GCCGCATAG    9600

TTAAGCCAGC CCCGACACCC GCCAACACCC GCTGACGCGC CCTGACGGGC T TGTCTGCTC    9660

CCGGCATCCG CTTACAGACA AGCTGTGACC GTCTCCGGGA GCTGCATGTG T CAGAGGTTT    9720

TCACCGTCAT CACCGAAACG CGCGAGACGA AAGGGCCTCG TGATACGCCT A TTTTTATAG    9780

GTTAATGTCA TGATAATAAT GGTTTCTTAG ACGTCAGGTG GCACTTTTCG G GGAAATGTG    9840

CGCGGAACCC CTATTTGTTT ATTTTTCTAA ATACATTCAA ATATGTATCC G CTCATGAGA    9900

CAATAACCCT GATAAATGCT TCAATAATAT TGAAAAAGGA AGAGTATGAG T ATTCAACAT    9960

TTCCGTGTCG CCCTTATTCC CTTTTTTGCG GCATTTTGCC TTCCTGTTTT T GCTCACCCA    10020

GAAACGCTGG TGAAAGTAAA AGATGCTGAA GATCAGTTGG GTGCACGAGT G GGTTACATC    10080

GAACTGGATC TCAACAGCGG TAAGATCCTT GAGAGTTTTC GCCCCGAAGA A CGTTTTCCA    10140

ATGATGAGCA CTTTTAAAGT TCTGCTATGT GGCGCGGTAT TATCCCGTAT T GACGCCGGG    10200

CAAGAGCAAC TCGGTCGCCG CATACACTAT TCTCAGAATG ACTTGGTTGA G TACTCACCA    10260

GTCACAGAAA AGCATCTTAC GGATGGCATG ACAGTAAGAG AATTATGCAG T GCTGCCATA    10320
```

```
ACCATGAGTG ATAACACTGC GGCCAACTTA CTTCTGACAA CGATCGGAGG A CCGAAGGAG    10380

CTAACCGCTT TTTTGCACAA CATGGGGGAT CATGTAACTC GCCTTGATCG T TGGGAACCG    10440

GAGCTGAATG AAGCCATACC AAACGACGAG CGTGACACCA CGATGCCTGT A GCAATGGCA    10500

ACAACGTTGC GCAAACTATT AACTGGCGAA CTACTTACTC TAGCTTCCCG G CAACAATTA    10560

ATAGACTGGA TGGAGGCGGA TAAAGTTGCA GGACCACTTC TGCGCTCGGC C CTTCCGGCT    10620

GGCTGGTTTA TTGCTGATAA ATCTGGAGCC GGTGAGCGTG GGTCTCGCGG T ATCATTGCA    10680

GCACTGGGGC CAGATGGTAA GCCCTCCCGT ATCGTAGTTA TCTACACGAC G GGGAGTCAG    10740

GCAACTATGG ATGAACGAAA TAGACAGATC GCTGAGATAG GTGCCTCACT G ATTAAGCAT    10800

TGGTAACTGT CAGACCAAGT TTACTCATAT ATACTTTAGA TTGATTTAAA A CTTCATTTT    10860

TAATTTAAAA GGATCTAGGT GAAGATCCTT TTTGATAATC TCATGACCAA A ATCCCTTAA    10920

CGTGAGTTTT CGTTCCACTG AGCGTCAGAC CCCGTAGAAA AGATCAAAGG A TCTTCTTGA    10980

GATCCTTTTT TTCTGCGCGT AATCTGCTGC TTGCAAACAA AAAAACCACC G CTACCAGCG    11040

GTGGTTTGTT TGCCGGATCA AGAGCTACCA ACTCTTTTTC CGAAGGTAAC T GGCTTCAGC    11100

AGAGCGCAGA TACCAAATAC TGTCCTTCTA GTGTAGCCGT AGTTAGGCCA C CACTTCAAG    11160

AACTCTGTAG CACCGCCTAC ATACCTCGCT CTGCTAATCC TGTTACCAGT G GCTGCTGCC    11220

AGTGGCGATA AGTCGTGTCT TACCGGGTTG GACTCAAGAC GATAGTTACC G GATAAGGCG    11280

CAGCGGTCGG GCTGAACGGG GGGTTCGTGC ACACAGCCCA GCTTGGAGCG A ACGACCTAC    11340

ACCGAACTGA GATACCTACA GCGTGAGCAT TGAGAAAGCG CCACGCTTCC C GAAGGGAGA    11400

AAGGCGGACA GGTATCCGGT AAGCGGCAGG GTCGGAACAG GAGAGCGCAC G AGGGAGCTT    11460

CCAGGGGGAA ACGCCTGGTA TCTTTATAGT CCTGTCGGGT TTCGCCACCT C TGACTTGAG    11520

CGTCGATTTT TGTGATGCTC GTCAGGGGGG CGGAGCCTAT GGAAAAACGC C AGCAACGCG    11580

GCCTTTTTAC GGTTCCTGGC CTTTTGCTGG CCTTTTGCTC ACATGTTCTT T CCTGCGTTA    11640

TCCCCTGATT CTGTGGATAA CCGTATTACC GCCTTTGAGT GAGCTGATAC C GCTCGCCGC    11700

AGCCGAACGA CCGAGCGCAG CGAGTCAGTG AGCGAGGAAG CGGAAGAGCG C CCAATACGC    11760

AAACCGCCTC TCCCCGCGCG TTGGCCGATT CATTAATGCA GCTGGCACGA C AGGTTTCCC    11820

GACTGGAAAG CGGGCAGTGA GCGCAACGCA ATTAATGTGA GTTAGCTCAC T CATTAGGCA    11880

CCCCAGGCTT TACACTTTAT GCTTCCGGCT CGTATGTTGT GTGGAATTGT G AGCGGATAA    11940

CAATTTCACA CAGGAAACAG CTATGACCAT GATTACGCCA AGCTTCCGCG G              11991

(2) INFORMATION FOR SEQ ID NO:11:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:11:

ACGTACGTAC GGGCCCACCA CTGTTGTAAC TTGTAAGCC                             39

(2) INFORMATION FOR SEQ ID NO:12:

(i) SEQUENCE CHARACTERISTICS:
           (A) LENGTH: 32 base pairs
           (B) TYPE: nucleic acid
           (C) STRANDEDNESS: single
```

(D) TOPOLOGY: linear (ii) MOLECULE TYPE: DNA (xi) SEQUENCE DESCRIPTION: SEQ ID NO:12:

AGGCGGACCT TTGCACTGTG AGTTACCTTC GC                                              32

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CTCTGTCGAC GAGCGCAGCT GCACGGGTC                                                  29

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCGAAGGTAA CTCACAGTGC AAAGGTCCGC CT                                              32

(2) INFORMATION FOR SEQ ID NO:15:

(i) SEQUENCE CHARACTERISTICS:
        (A) LENGTH: 9299 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:15:

GAGCTCCACC GCGGTGGCGG CCGCTCTAGA ACTAGTGGAT CCGTCGACCA T GGCCAGTTG       60

CCGGTGGAGC AGGTAAAAAC ACCGTAGCGT AGCAGCCAGG CGGAAGCAGA C GCACAGCAC      120

AGGTTGGTTA TGATAGTCAG CCGGGCCACA TGTGTGTAGT TGGTACACTG A TACGCTTAC      180

ACTGTCTCTC CTTTCTTTTT TATTTGTCAC CTTTGGTCGA GCTTACATAA T TGTGTGACT      240

AAAAAAAGGT CACTTCATTC AGAAATTTAG GGTTGTGGGA ATTTTGGATT T TATTGTGTC      300

TGTATAGAGT AGCTATAGCT AGCTAGCTAG ATGTGATGTT AATAATTATG A CGATGAGAT      360

TGGCCCGCTT GGCCGCTTGC ATTGTCTCCC TAGCTCAATA ATGTTTTGAG T TGTCTTGC       420

CTTTCTTTCA GCTCTAACAA ATTGGAGTAG GGATGACTGA GATACATATA T AAAAGCGAA      480

AACCGCTGCT CTCTGTTAAT TATTGCACAT CACACATAGG CCAAGCCTTA A GGACAATCA      540

ACTAAGGATG GTAATAACTA AGGCTAGTGA GGTCGAACTA GGGATGTTAA T ATACTCTAG      600

ATTTTAGACT ATAAAATTTA AGGATCGAAT CAGATTAGTA TCGAACTATA T TTATATTCA      660

TTTCTAAACT AAATTAATTA AGCACCCTAA ATTATTGTGA TGAAGAGACA T TTCGATCGT      720

GATCCATTAT TACTCCTTGG TCAAACTAAT CTCGTTTTAT GTCACTATTT C ATCATCTTT      780

TTTGCGAACG GGTTTATAGC CCGTGTTCCA TTATGAGGAC ATGAACGGTT T AAACAAAGT      840

```
TACATATCAT CCCAGCTAGC TACCTAGATT GGAAGCATGG GTTCGGTATA T ATATATAGT    900
TTATATATTT GGTATATATA TATATATATA TATATATATA TATATATCAC A CGTCAGCTT    960
ATATTACGTA AAGTGGGGTT AGTTTTCAAG AAGCGTGGGA CCAGTCACCT C TGCAGTCTG   1020
ACCTTGGCTT CAGCTTCGAC AGCAAACAGT CATCTCTTGG AAGCTAAGGA C AGTCTCCAA   1080
CAGTCAACAA AGCAGCGGTC TGCTTGTAGT TCTCCCTTGC ACGACCAGCT A TATCTAGCA   1140
TCATAACAAC GGTAAGATCA TCTCTAGCAC GACAAACTTA GTTTAATTAA T TATGTCTAA   1200
TCCGTTGTTG TTAGCTTAAA CTTTCTAGCC TCCTATGCTA AGAGAGTTCT C TAGTTCTAC   1260
TCAGGTGGAT TGATATATAA ATTGGGAATC TTCTAGGCGT CACAAGGTAT G GTACACATC   1320
AATCAATGAA CGGACAAAGC AACGGTAAGA TCCGACCCAG TAAAAGTAAT A GCGTTAGGG   1380
CATGTACAAC CTAGACACTG ATGCACAGTA CTCCAAGTAT AAGACACAAC T AAAACACAA   1440
CATAATAATA CAGTGGTTAT ATCTAAAACA TGTGTCTTAC CATATTCATT G TACCAATTA   1500
GAACATTTAA TAAATTAAAG TGACCAATCA GCTAGCCTCC TGTCTCGAAC A TAGAGCTAA   1560
GACATTGTGT CTTCGTCAAG ATACATGTCT TAAGTTTTTT TATATTCACT C CCAAAGACA   1620
CACTCTAAGA CACAACGTAA CACACCCATT GTACATGCTC TTAACCTAAG T TATCATGGA   1680
TGACCACGCG TGGCAATTAA AAAAATAATT TTTGCCTCCT AAAACCTCTT T CTTAATTGG   1740
TTCTTGCTTG CAAATCACCA GCGAACCCAT ATGAAAGGAT GCTCAAAATC T GGCCACCGC   1800
ATCAGGGTTG GTGAATGCAA VGTAAAAAAT AATGCATAAA TCAGCTCTCT G ATCAGTTAT   1860
ATAATCGTGC CTTTTAATTA TTCATGCCAG CTTTATCTGA CTCACGAAAT C ATTGATAAA   1920
TTATTCCTCA GCTGTATTAG AAAGAGCAGT GTTGTTTAAC TTGGAAAGTG A TGTGGAAGC   1980
GTGTGATTGC GGTTGAGCTT GTATAGGAGT AAAATGAGGA ACAGTAGGAA A ATAATTTTT   2040
TCGGATTAAA ACCGGTTGTT TGGACTGCGG CAGATACAAT TCATAGAGAT A AAAACACCG   2100
TAGAAGTATT AGAAGCCGAT AAAGATTAAA CCCAAATGAA CGAACAGGCT A AACAAATCC   2160
GGCGCCTCAA AAGTCAAGAG CAGGTACTGG GCTGTCTTGC ACACGTCGCT T TTTGTCTCC   2220
CCCTGGCCCC TGGGTGAGAG TAGTAGGGAT GCTAAAGTTT GCTTTCTCTT T TTGAGGCAT   2280
GTGATAGGCT CTTGTTAGTT GCTAGGGCTA TGTTTATAAT ATTTGCGCTT T TACCTATGT   2340
ACGTAAGAAC CGGATGGAAT AATGCTATGC AGGAACCAAT TATGTTTGGT C GAAATATAT   2400
AGTGACCTAT CATAATGTTA TCCCTGTTCA TGTACCTAGG TGGCTAATGA T ATACGGCAT   2460
ATGAATACAG TAATCATCCA AGCACGTAAA AACTCGCTAG ACGTTTATGC C TGCTAGCCT   2520
GCTGGGTGTG TAGACTGGAG TACTGGACAA ACATCGCAAT ACAGAGGTAC A GTATTTGTC   2580
TAGACAATGA TATACATAGA TAAAAACCAC TGTTGTAACT TGTAAGCCAC T AGCTCACGT   2640
TCTCCATGAG CTCTTCTCTC TGCTGTTTCT TCCTCTGCTA ACTGCGTTAT G ATATGACGT   2700
CGTATAAATA ATCTCACAAT ACTTCCTTAT TTTCAGCATG GCCTCTTTTA T GTTTATTTA   2760
ACAGTAGCAA CCAACGCCGC TCGATGTTTC CTTCAAGAAA CGGCCACTCA C TATGTGGTG   2820
TGCAGAAGAA CAAATGTAAG CAGCTCCTAC AGGTACCAGT AGTCATGTCA G TGTGGAAGC   2880
TTTCCAACCA ACGCCTCCTT CGAGGAACCT GGTCGTGCTG ACATGAATGT A GGCCATGCA   2940
AGCACAAGCA CCTAACGCGA ATCATCACGA CGCGCCGTGT ACTGGGCGTT G GTACATCAC   3000
ACCCCGCGTT TGACCTGATC GGAAGCATGC GTGTGTGTTG GCTGCAGGAC C GGCTATAGG   3060
TTTCCTGCAT TGGACAGCAG AAGCCAGTCA TGTTAGGCAC TCACGCGCTC C TGCCGTTTG   3120
ATGAATCATC CGGTCTTTCG TATTGATCAC TAGTTCACTA CGCTGATATA G CAAATTTTA   3180
AGATGTGAAA CCACGAGACG AGCGATAAAT CTTAGACGTT ACCTATCCAT A TGAAGCTTG   3240
```

```
TGCGAAAAAA AGGCGTGCCG CTGTAGCATC ATTCGTATAC ACTTTTGTCC C CAAAGACAG    3300
GGATACGAAT CCATGCTCGA CAGAACCCTC CCTTCCCTGC AGATAACGAC A CTTAAGTAT    3360
AACAAAAGTA GTTGGATTAT TTCAGAAGCA AAATCTCACT TTTCGCTGGC C TTTTTGTAC    3420
TTTGGTTACT TGAGTTCAGA CAGTGTATGC TATATTGTCA TGTGCTGCGT A AGGTTTAAA    3480
TATGGTTCGA CAAATATATC AGTATATCAC TACTTTGTTA TGGGTGGGGC C TAGCACAAA    3540
CTTGATACAG CTAGGATAAA GTTAGAACGA TGACTGATCT ACTGTAAAGC G ACACCTGTC    3600
CTGTTATGGT AGTTTAAGTC CATTCCTGGA CGACTCCAGA TCCAGGATAT G ATGCTGTTA    3660
CATAATGCGA TTGTTCACAA TAAAATTGCA TGATGTTCTT CTACTCTTTA G GCAGTTTTG    3720
TTCAACAGGC AAGTTGCATA ATGCATGTGC ATATATGAGC AGCATAATCA T CAATTAATC    3780
ATAGGTTCGT CATTTTAGTT TCACTCCTTC ACATTATTCC AGCCCTTGAA G AAAAATGTA    3840
GCAGTGCTTG CTGTTTAATA AGTGGCAGAG CTGTTTTCAC TCCACCTACG C TTGTCTAGG    3900
ACCAAAATTT TAATCTGTCA CTTTGAGCTA AAACTGAAGC ACCAAACCGC T ACAAAAGAA    3960
CGTAGGAGCT GAATTGTAAC TTGATGGGAT TACTATAGCA GTTGCTACAG T TCTAGCTAG    4020
CTACCTTATT CTATACGCAT CACCCTAACA ACCCGGCTGA CTGCTGCATC T GACCCCACC    4080
GTCCCCTGCT CCAAACCAAC TCTCCTTTCC TTGCATGCAC TACACCCACT T CCTGCAGCT    4140
ATATATACCA CCATATGCCC ATCTTATGAA ACCATCCACA AGAGGAGAAG A AACAATCAA    4200
CCAGCAACAC TCTTCTCTTA TAACATAGTA CAGCGAAGGT AACTCACATG G CAACTTCCA    4260
TGGTCCGTCC TGTAGAAACC CCAACCCGTG AAATCAAAAA ACTCGACGGC C TGTGGGCAT    4320
TCAGTCTGGA TCGCGAAAAC TGTGGAATTG ATCAGCGTTG GTGGGAAAGC G CGTTACAAG    4380
AAAGCCGGGC AATTGCTGTG CCAGGCAGTT TTAACGATCA GTTCGCCGAT G CAGATATTC    4440
GTAATTATGC GGGCAACGTC TGGTATCAGC GCGAAGTCTT TATACCGAAA G GTTGGGCAG    4500
GCCAGCGTAT CGTGCTGCGT TTCGATGCGG TCACTCATTA CGGCAAAGTG T GGGTCAATA    4560
ATCAGGAAGT GATGGAGCAT CAGGGCGGCT ATACGCCATT TGAAGCCGAT G TCACGCCGT    4620
ATGTTATTGC CGGGAAAAGT GTACGTATCA CCGTTTGTGT GAACAACGAA C TGAACTGGC    4680
AGACTATCCC GCCGGGAATG GTGATTACCG ACGAAAACGG CAAGAAAAAG C AGTCTTACT    4740
TCCATGATTT CTTTAACTAT GCCGGAATCC ATCGCAGCGT AATGCTCTAC A CCACGCCGA    4800
ACACCTGGGT GGACGATATC ACCGTGGTGA CGCATGTCGC GCAAGACTGT A ACCACGCGT    4860
CTGTTGACTG GCAGGTGGTG GCCAATGGTG ATGTCAGCGT TGAACTGCGT G ATGCGGATC    4920
AACAGGTGGT TGCAACTGGA CAAGGCACTA GCGGGACTTT GCAAGTGGTG A ATCCGCACC    4980
TCTGGCAACC GGGTGAAGGT TATCTCTATG AACTGTGCGT CACAGCCAAA A GCCAGACAG    5040
AGTGTGATAT CTACCCGCTT CGCGTCGGCA TCCGGTCAGT GGCAGTGAAG G GCGAACAGT    5100
TCCTGATTAA CCACAAACCG TTCTACTTTA CTGGCTTTGG TCGTCATGAA G ATGCGGACT    5160
TACGTGGCAA AGGATTCGAT AACGTGCTGA TGGTGCACGA CCACGCATTA A TGGACTGGA    5220
TTGGGGCCAA CTCCTACCGT ACCTCGCATT ACCCTTACGC TGAAGAGATG C TCGACTGGG    5280
CAGATGAACA TGGCATCGTG GTGATTGATG AAACTGCTGC TGTCGGCTTT A ACCTCTCTT    5340
TAGGCATTGG TTTCGAAGCG GGCAACAAGC CGAAAGAACT GTACAGCGAA G AGGCAGTCA    5400
ACGGGGAAAC TCAGCAAGCG CACTTACAGG CGATTAAAGA GCTGATAGCG C GTGACAAAA    5460
ACCACCCAAG CGTGGTGATG TGGAGTATTG CCAACGAACC GGATACCCGT C CGCAAGTGC    5520
ACGGGAATAT TTCGCCACTG GCGGAAGCAA CGCGTAAACT CGACCCGACG C GTCCGATCA    5580
```

-continued

```
CCTGCGTCAA TGTAATGTTC TGCGACGCTC ACACCGATAC CATCAGCGAT C TCTTTGATG      5640

TGCTGTGCCT GAACCGTTAT TACGGATGGT ATGTCCAAAG CGGCGATTTG G AAACGGCAG      5700

AGAAGGTACT GGAAAAAGAA CTTCTGGCCT GGCAGGAGAA ACTGCATCAG C CGATTATCA      5760

TCACCGAATA CGGCGTGGAT ACGTTAGCCG GGCTGCACTC AATGTACACC G ACATGTGGA      5820

GTGAAGAGTA TCAGTGTGCA TGGCTGGATA TGTATCACCG CGTCTTTGAT C GCGTCAGCG      5880

CCGTCGTCGG TGAACAGGTA TGGAATTTCG CCGATTTTGC GACCTCGCAA G GCATATTGC      5940

GCGTTGGCGG TAACAAGAAA GGGATCTTCA CTCGCGACCG CAAACCGAAG T CGGCGGCTT      6000

TTCTGCTGCA AAAACGCTGG ACTGGCATGA ACTTCGGTGA AAAACCGCAG C AGGGAGGCA      6060

AACAATGAAT CAACAACTCT CCTGGCGCAC CATCGTCGGC TACAGCCTCG G TGGGGAATT      6120

GGAGCTCGAA TTTCCCCGAT CGTTCAAACA TTTGGCAATA AGTTTCTTA A GATTGAATC      6180

CTGTTGCCGG TCTTGCGATG ATTATCATAT AATTTCTGTT GAATTACGTT A AGCATGTAA      6240

TAATTAACAT GTAATGCATG ACGTTATTTA TGAGATGGGT TTTTATGATT A GAGTCCCGC      6300

AATTATACAT TTAATACGCG ATAGAAAACA AAATATAGCG CGCAAACTAG G ATAAATTAT      6360

CGCGCGCGGT GTCATCTATG TTACTAGATC GATCGGGAAT TAAGCTTATC G ATACCGTCG      6420

ACCTCGAGGG GGGGCCCGGT ACCCAATTCG CCCTATAGTG AGTCGTATTA C AATTCACTG      6480

GCCGTCGTTT TACAACGTCG TGACTGGGAA AACCCTGGCG TTACCCAACT T AATCGCCTT      6540

GCAGCACATC CCCCTTTCGC CAGCTGGCGT AATAGCGAAG AGGCCCGCAC C GATCGCCCT      6600

TCCCAACAGT TGCGCAGCCT GAATGGCGAA TGGCGCGAAA TTGTAAACGT T AATATTTTG      6660

TTAAAATTCG CGTTAAATTT TTGTTAAATC AGCTCATTTT TTAACCAATA G GCCGAAATC      6720

GGCAAAATCC CTTATAAATC AAAAGAATAG ACCGAGATAG GGTTGAGTGT T GTTCCAGTT      6780

TGGAACAAGA GTCCACTATT AAAGAACGTG GACTCCAACG TCAAAGGGCG A AAAACCGTC      6840

TATCAGGGCG ATGGCCCACT ACGTGAACCA TCACCCTAAT CAAGTTTTTT G GGGTCGAGG      6900

TGCCGTAAAG CACTAAATCG GAACCCTAAA GGGAGCCCCC GATTTAGAGC T TGACGGGGA      6960

AAGCCGGCGA ACGTGGCGAG AAAGGAAGGG AAGAAAGCGA AAGGAGCGGG C GCTAGGGCG      7020

CTGGCAAGTG TAGCGGTCAC GCTGCGCGTA ACCACCACAC CCGCCGCGCT T AATGCGCCG      7080

CTACAGGGCG CGTCCCAGGT GGCACTTTTC GGGGAAATGT GCGCGGAACC C CTATTTGTT      7140

TATTTTTCTA AATACATTCA AATATGTATC CGCTCATGAG ACAATAACCC T GATAAATGC      7200

TTCAATAATA TTGAAAAAGG AAGAGTATGA GTATTCAACA TTTCCGTGTC G CCCTTATTC      7260

CCTTTTTTGC GGCATTTTGC CTTCCTGTTT TTGCTCACCC AGAAACGCTG G TGAAAGTAA      7320

AAGATGCTGA AGATCAGTTG GGTGCACGAG TGGGTTACAT CGAACTGGAT C TCAACAGCG      7380

GTAAGATCCT TGAGAGTTTT CGCCCCGAAG AACGTTTTCC AATGATGAGC A CTTTTAAAG      7440

TTCTGCTATG TGGCGCGGTA TTATCCCGTA TTGACGCCGG GCAAGAGCAA C TCGGTCGCC      7500

GCATACACTA TTCTCAGAAT GACTTGGTTG AGTACTCACC AGTCACAGAA A AGCATCTTA      7560

CGGATGGCAT GACAGTAAGA GAATTATGCA GTGCTGCCAT AACCATGAGT G ATAACACTG      7620

CGGCCAACTT ACTTCTGACA ACGATCGGAG GACCGAAGGA GCTAACCGCT T TTTTGCACA      7680

ACATGGGGGA TCATGTAACT CGCCTTGATC GTTGGGAACC GGAGCTGAAT G AAGCCATAC      7740

CAAACGACGA GCGTGACACC ACGATGCCTG TAGCAATGGC AACAACGTTG C GCAAACTAT      7800

TAACTGGCGA ACTACTTACT CTAGCTTCCC GGCAACAATT AATAGACTGG A TGGAGGCGG      7860

ATAAAGTTGC AGGACCACTT CTGCGCTCGG CCCTTCCGGC TGGCTGGTTT A TTGCTGATA      7920

AATCTGGAGC CGGTGAGCGT GGGTCTCGCG GTATCATTGC AGCACTGGGG C CAGATGGTA      7980
```

```
AGCCCTCCCG TATCGTAGTT ATCTACACGA CGGGGAGTCA GGCAACTATG G ATGAACGAA      8040

ATAGACAGAT CGCTGAGATA GGTGCCTCAC TGATTAAGCA TTGGTAACTG T CAGACCAAG      8100

TTTACTCATA TATACTTTAG ATTGATTTAA AACTTCATTT TTAATTTAAA A GGATCTAGG      8160

TGAAGATCCT TTTTGATAAT CTCATGACCA AAATCCCTTA ACGTGAGTTT T CGTTCCACT      8220

GAGCGTCAGA CCCCGTAGAA AAGATCAAAG GATCTTCTTG AGATCCTTTT T TTCTGCGCG      8280

TAATCTGCTG CTTGCAAACA AAAAAACCAC CGCTACCAGC GGTGGTTTGT T TGCCGGATC      8340

AAGAGCTACC AACTCTTTTT CCGAAGGTAA CTGGCTTCAG CAGAGCGCAG A TACCAAATA      8400

CTGTCCTTCT AGTGTAGCCG TAGTTAGGCC ACCACTTCAA GAACTCTGTA G CACCGCCTA      8460

CATACCTCGC TCTGCTAATC CTGTTACCAG TGGCTGCTGC CAGTGGCGAT A AGTCGTGTC      8520

TTACCGGGTT GGACTCAAGA CGATAGTTAC CGGATAAGGC GCAGCGGTCG G GCTGAACGG      8580

GGGGTTCGTG CACACAGCCC AGCTTGGAGC GAACGACCTA CACCGAACTG A GATACCTAC      8640

AGCGTGAGCT ATGAGAAAGC GCCACGCTTC CCGAAGGGAG AAAGGCGGAC A GGTATCCGG      8700

TAAGCGGCAG GGTCGGAACA GGAGAGCGCA CGAGGGAGCT TCCAGGGGGA A ACGCCTGGT      8760

ATCTTTATAG TCCTGTCGGG TTTCGCCACC TCTGACTTGA GCGTCGATTT T TGTGATGCT      8820

CGTCAGGGGG GCGGAGCCTA TGGAAAAACG CCAGCAACGC GGCCTTTTTA C GGTTCCTGG      8880

CCTTTTGCTG GCCTTTTGCT CACATGTTCT TTCCTGCGTT ATCCCCTGAT T CTGTGGATA      8940

ACCGTATTAC CGCCTTTGAG TGAGCTGATA CCGCTCGCCG CAGCCGAACG A CCGAGCGCA      9000

GCGAGTCAGT GAGCGAGGAA GCGGAAGAGC GCCCAATACG CAAACCGCCT C TCCCCGCGC      9060

GTTGGCCGAT TCATTAATGC AGCTGGCACG ACAGGTTTCC CGACTGGAAA G CGGGCAGTG      9120

AGCGCAACGC AATTAATGTG AGTTAGCTCA CTCATTAGGC ACCCCAGGCT T TACACTTTA      9180

TGCTTCCGGC TCGTATGTTG TGTGGAATTG TGAGCGGATA ACAATTTCAC A CAGGAAACA      9240

GCTATGACCA TGATTACGCC AAGCTCGGAA TTAACCCTCA CTAAAGGGAA C AAAAGCTG      9299

(2) INFORMATION FOR SEQ ID NO:16:

(i) SEQUENCE CHARACTERISTICS:
            (A) LENGTH: 9408 base pairs
            (B) TYPE: nucleic acid
            (C) STRANDEDNESS: double
            (D) TOPOLOGY: circular (ii) MOLECULE TYPE: DNA (xi) SEQUENCE DESCRIPTION: SEQ ID NO:16:

GAGCTCCACC GCGGTGGCGG CCGCTCTAGA ACTAGTGGAT CCTCTAGAGT C GACCATGGC        60

CAGTTGCCGG TGGAGCAGGT AAAAACACCG TAGCGTAGCA GCCAGGCGGA A GCAGACGCA       120

CAGCACAGGT TGGTTATGAT AGTCAGCCGG GCCACATGTG TGTAGTTGGT A CACTGATAC       180

GCTTACACTG TCTCTCCTTT CTTTTTTATT TGTCACCTTT GGTCGAGCTT A CATAATTGT       240

GTGACTAAAA AAAGGTCACT TCATTCAGAA ATTTAGGGTT GTGGGAATTT T GGATTTTAT       300

TGTGTCTGTA TAGAGTAGCT ATAGCTAGCT AGCTAGATGT GATGTTAATA A TTATGACGA       360

TGAGATTGGC CCGCTTGGCC GCTTGCATTG TCTCCCTAGC TCAATAATGT T TTGAGTTTG       420

TCTTGCCTTT CTTTCAGCTC TAACAAATTG GAGTAGGGAT GACTGAGATA C ATATATAAA       480

AGCGAAAACC GCTGCTCTCT GTTAATTATT GCACATCACA CATAGGCCAA G CCTTAAGGA       540

CAATCAACTA AGGATGGTAA TAACTAAGGC TAGTGAGGTC GAACTAGGGA T GTTAATATA       600

CTCTAGATTT TAGACTATAA AATTTAAGGA TCGAATCAGA TTAGTATCGA A CTATATTTA       660
```

```
TATTCATTTC TAAACTAAAT TAATTAAGCA CCCTAAATTA TTGTGATGAA G AGACATTTC    720
GATCGTGATC CATTATTACT CCTTGGTCAA ACTAATCTCG TTTTATGTCA C TATTTCATC    780
ATCTTTTTTG CGAACGGGTT TATAGCCCGT GTTCCATTAT GAGGACATGA A CGGTTTAAA    840
CAAAGTTACA TATCATCCCA GCTAGCTACC TAGATTGGAA GCATGGGTTC G GTATATATA    900
TATAGTTTAT ATATTTGGTA TATATATATA TATATATATA TATATATATA T ATCACACGT    960
CAGCTTATAT TACGTAAAGT GGGGTTAGTT TTCAAGAAGC GTGGGACCAG T CACCTCTGC   1020
AGTCTGACCT TGGCTTCAGC TTCGACAGCA AACAGTCATC TCTTGGAAGC T AAGGACAGT   1080
CTCCAACAGT CAACAAAGCA GCGGTCTGCT TGTAGTTCTC CCTTGCACGA C CAGCTATAT   1140
CTAGCATCAT AACAACGGTA AGATCATCTC TAGCACGACA AACTTAGTTT A ATTAATTAT   1200
GTCTAATCCG TTGTTGTTAG CTTAAACTTT CTAGCCTCCT ATGCTAAGAG A GTTCTCTAG   1260
TTCTACTCAG GTGGATTGAT ATATAAATTG GGAATCTTCT AGGCGTCACA A GGTATGGTA   1320
CACATCAATC AATGAACGGA CAAAGCAACG GTAAGATCCG ACCCAGTAAA A GTAATAGCG   1380
TTAGGGCATG TACAACCTAG ACACTGATGC ACAGTACTCC AAGTATAAGA C ACAACTAAA   1440
ACACAACATA ATAATACAGT GGTTATATCT AAAACATGTG TCTTACCATA T TCATTGTAC   1500
CAATTAGAAC ATTTAATAAA TTAAAGTGAC CAATCAGCTA GCCTCCTGTC T CGAACATAG   1560
AGCTAAGACA TTGTGTCTTC GTCAAGATAC ATGTCTTAAG TTTTTTTATA T TCACTCCCA   1620
AAGACACACT CTAAGACACA ACGTAACACA CCCATTGTAC ATGCTCTTAA C CTAAGTTAT   1680
CATGGATGAC CACGCGTGGC AATTAAAAAA ATAATTTTTG CCTCCTAAAA C CTCTTTCTT   1740
AATTGGTTCT TGCTTGCAAA TCACCAGCGA ACCCATATGA AAGGATGCTC A AAATCTGGC   1800
CACCGCATCA GGGTTGGTGA ATGCAAVGTA AAAAATAATG CATAAATCAG C TCTCTGATC   1860
AGTTATATAA TCGTGCCTTT TAATTATTCA TGCCAGCTTT ATCTGACTCA C GAAATCATT   1920
GATAAATTAT TCCTCAGCTG TATTAGAAAG AGCAGTGTTG TTTAACTTGG A AAGTGATGT   1980
GGAAGCGTGT GATTGCGGTT GAGCTTGTAT AGGAGTAAAA TGAGGAACAG T AGGAAAATA   2040
ATTTTTTCGG ATTAAAACCG GTTGTTTGGA CTGCGGCAGA TACAATTCAT A GAGATAAAA   2100
ACACCGTAGA AGTATTAGAA GCCGATAAAG ATTAAACCCA AATGAACGAA C AGGCTAAAC   2160
AAATCCGGCG CCTCAAAAGT CAAGAGCAGG TACTGGGCTG TCTTGCACAC G TCGCTTTTT   2220
GTCTCCCCCT GGCCCCTGGG TGAGAGTAGT AGGGATGCTA AAGTTTGCTT T CTCTTTTTG   2280
AGGCATGTGA TAGGCTCTTG TTAGTTGCTA GGGCTATGTT TATAATATTT G CGCTTTTAC   2340
CTATGTACGT AAGAACCGGA TGGAATAATG CTATGCAGGA ACCAATTATG T TTGGTCGAA   2400
ATATATAGTG ACCTATCATA ATGTTATCCC TGTTCATGTA CCTAGGTGGC T AATGATATA   2460
CGGCATATGA ATACAGTAAT CATCCAAGCA CGTAAAAACT CGCTAGACGT T TATGCCTGC   2520
TAGCCTGCTG GGTGTGTAGA CTGGAGTACT GGACAAACAT CGCAATACAG A GGTACAGTA   2580
TTTGTCTAGA CAATGATATA CATAGATAAA AACCACTGTT GTAACTTGTA A GCCACTAGC   2640
TCACGTTCTC CATGAGCTCT TCTCTCTGCT GTTTCTTCCT CTGCTAACTG C GTTATGATA   2700
TGACGTCGTA TAAATAATCT CACAATACTT CCTTATTTTC AGCATGGCCT C TTTTATGTT   2760
TATTTAACAG TAGCAACCAA CGCCGCTCGA TGTTTCCTTC AAGAAACGGC C ACTCACTAT   2820
GTGGTGTGCA GAAGAACAAA TGTAAGCAGC TCCTACAGGT ACCAGTAGTC A TGTCAGTGT   2880
GGAAGCTTTC CAACCAACGC CTCCTTCGAG GAACCTGGTC GTGCTGACAT G AATGTAGGC   2940
CATGCAAGCA CAAGCACCTA ACGCGAATCA TCACGACGCG CCGTGTACTG G GCGTTGGTA   3000
```

-continued

```
CATCACACCC CGCGTTTGAC CTGATCGGAA GCATGCGTGT GTGTTGGCTG C AGGACCGGC      3060
TATAGGTTTC CTGCATTGGA CAGCAGAAGC CAGTCATGTT AGGCACTCAC G CGCTCCTGC      3120
CGTTTGATGA ATCATCCGGT CTTTCGTATT GATCACTAGT TCACTACGCT G ATATAGCAA      3180
ATTTTAAGAT GTGAAACCAC GAGACGAGCG ATAAATCTTA GACGTTACCT A TCCATATGA      3240
AGCTTGTGCG AAAAAAAGGC GTGCCGCTGT AGCATCATTC GTATACACTT T TGTCCCCAA      3300
AGACAGGGAT ACGAATCCAT GCTCGACAGA ACCCTCCCTT CCCTGCAGAT A ACGACACTT      3360
AAGTATAACA AAAGTAGTTG GATTATTTCA GAAGCAAAAT CTCACTTTTC G CTGGCCTTT      3420
TTGTACTTTG GTTACTTGAG TTCAGACAGT GTATGCTATA TTGTCATGTG C TGCGTAAGG      3480
TTTAAATATG GTTCGACAAA TATATCAGTA TATCACTACT TTGTTATGGG T GGGGCCTAG      3540
CACAAACTTG ATACAGCTAG GATAAAGTTA GAACGATGAC TGATCTACTG T AAAGCGACA      3600
CCTGTCCTGT TATGGTAGTT TAAGTCCATT CCTGGACGAC TCCAGATCCA G GATATGATG      3660
CTGTTACATA ATGCGATTGT TCACAATAAA ATTGCATGAT GTTCTTCTAC T CTTTAGGCA      3720
GTTTTGTTCA ACAGGCAAGT TGCATAATGC ATGTGCATAT ATGAGCAGCA T AATCATCAA      3780
TTAATCATAG GTTCGTCATT TTAGTTTCAC TCCTTCACAT TATTCCAGCC C TTGAAGAAA      3840
AATGTAGCAG TGCTTGCTGT TTAATAAGTG GCAGAGCTGT TTTCACTCCA C CTACGCTTG      3900
TCTAGGACCA AAATTTTAAT CTGTCACTTT GAGCTAAAAC TGAAGCACCA A ACCGCTACA      3960
AAAGAACGTA GGAGCTGAAT TGTAACTTGA TGGGATTACT ATAGCAGTTG C TACAGTTCT      4020
AGCTAGCTAC CTTATTCTAT ACGCATCACC CTAACAACCC GGCTGACTGC T GCATCTGAC      4080
CCCACCGTCC CCTGCTCCAA ACCAACTCTC CTTTCCTTGC ATGCACTACA C CCACTTCCT      4140
GCAGCTATAT ATACCACCAT ATGCCCATCT TATGAAACCA TCCACAAGAG G AGAAGAAAC      4200
AATCAACCAG CAACACTCTT CTCTTATAAC ATAGTACAGC GAAGGTAACT C ACATGGCAA      4260
CTTCCATGGT CCGTCCTGTA GAAACCCCAA CCCGTGAAAT CAAAAAACTC G ACGGCCTGT      4320
GGGCATTCAG TCTGGATCGC GAAAACTGTG GAATTGATCA GCGTTGGTGG G AAAGCGCGT      4380
TACAAGAAAG CCGGGCAATT GCTGTGCCAG GCAGTTTTAA CGATCAGTTC G CCGATGCAG      4440
ATATTCGTAA TTATGCGGGC AACGTCTGGT ATCAGCGCGA AGTCTTTATA C CGAAAGGTT      4500
GGGCAGGCCA GCGTATCGTG CTGCGTTTCG ATGCGGTCAC TCATTACGGC A AAGTGTGGG      4560
TCAATAATCA GGAAGTGATG GAGCATCAGG GCGGCTATAC GCCATTTGAA G CCGATGTCA      4620
CGCCGTATGT TATTGCCGGG AAAAGTGTAC GTATCACCGT TTGTGTGAAC A ACGAACTGA      4680
ACTGGCAGAC TATCCCGCCG GGAATGGTGA TTACCGACGA AAACGGCAAG A AAAAGCAGT      4740
CTTACTTCCA TGATTTCTTT AACTATGCCG GAATCCATCG CAGCGTAATG C TCTACACCA      4800
CGCCGAACAC CTGGGTGGAC GATATCACCG TGGTGACGCA TGTCGCGCAA G ACTGTAACC      4860
ACGCGTCTGT TGACTGGCAG GTGGTGGCCA ATGGTGATGT CAGCGTTGAA C TGCGTGATG      4920
CGGATCAACA GGTGGTTGCA ACTGGACAAG GCACTAGCGG GACTTTGCAA G TGGTGAATC      4980
CGCACCTCTG GCAACCGGGT GAAGGTTATC TCTATGAACT GTGCGTCACA G CCAAAAGCC      5040
AGACAGAGTG TGATATCTAC CCGCTTCGCG TCGGCATCCG GTCAGTGGCA G TGAAGGGCG      5100
AACAGTTCCT GATTAACCAC AAACCGTTCT ACTTTACTGG CTTTGGTCGT C ATGAAGATG      5160
CGGACTTACG TGGCAAAGGA TTCGATAACG TGCTGATGGT GCACGACCAC G CATTAATGG      5220
ACTGGATTGG GGCCAACTCC TACCGTACCT CGCATTACCC TTACGCTGAA G AGATGCTCG      5280
ACTGGGCAGA TGAACATGGC ATCGTGGTGA TTGATGAAAC TGCTGCTGTC G GCTTTAACC      5340
TCTCTTTAGG CATTGGTTTC GAAGCGGGCA ACAAGCCGAA AGAACTGTAC A GCGAAGAGG      5400
```

```
CAGTCAACGG GGAAACTCAG CAAGCGCACT TACAGGCGAT TAAAGAGCTG A TAGCGCGTG      5460

ACAAAAACCA CCCAAGCGTG GTGATGTGGA GTATTGCCAA CGAACCGGAT A CCCGTCCGC      5520

AAGTGCACGG GAATATTTCG CCACTGGCGG AAGCAACGCG TAAACTCGAC C CGACGCGTC      5580

CGATCACCTG CGTCAATGTA ATGTTCTGCG ACGCTCACAC CGATACCATC A GCGATCTCT      5640

TTGATGTGCT GTGCCTGAAC CGTTATTACG GATGGTATGT CCAAAGCGGC G ATTTGGAAA      5700

CGGCAGAGAA GGTACTGGAA AAAGAACTTC TGGCCTGGCA GGAGAAACTG C ATCAGCCGA      5760

TTATCATCAC CGAATACGGC GTGGATACGT TAGCCGGGCT GCACTCAATG T ACACCGACA      5820

TGTGGAGTGA AGAGTATCAG TGTGCATGGC TGGATATGTA TCACCGCGTC T TTGATCGCG      5880

TCAGCGCCGT CGTCGGTGAA CAGGTATGGA ATTTCGCCGA TTTTGCGACC T CGCAAGGCA      5940

TATTGCGCGT TGGCGGTAAC AAGAAAGGGA TCTTCACTCG CGACCGCAAA C CGAAGTCGG      6000

CGGCTTTTCT GCTGCAAAAA CGCTGGACTG GCATGAACTT CGGTGAAAAA C CGCAGCAGG      6060

GAGGCAAACA ATGAATCAAC AACTCTCCTG GCGCACCATC GTCGGCTACA G CCTCGGGAA      6120

TTGCTACCGA GCTTCTCGAG GGCACTGAAG TCGCTTGATG TGCTGAATTG T TTGTGATGT      6180

TGGTGGCGTA TTTTGTTTAA ATAAGTAAGC ATGGCTGTGA TTTTATCATA T GATCGATCT      6240

TTGGGGTTTT ATTTAACACA TTGTAAAATG TGTATCTATT AATAACTCAA T GTATAAGAT      6300

GTGTTCATTC TTCGGTTGCC ATAGATCTGC TTATTTGACC TGTGATGTTT T GACTCCAAA      6360

AACCAAAATC ACAACTCAAT AAACTCATGG AATATGTCCA CCTGTTTCTT G AAGAGTTCA      6420

TCTACCATTC CAGTTGGCAT TTATCAGTGT TGCAGCGGCG CTGTGCTTTG T AACATAACA      6480

ATTGTTCACG GCATATATCC AAATCTAGAG AAGCTTATCG ATACCGTCGA C CTCGAGGGG      6540

GGGCCCGGTA CCCAATTCGC CCTATAGTGA GTCGTATTAC AATTCACTGG C CGTCGTTTT      6600

ACAACGTCGT GACTGGGAAA ACCCTGGCGT TACCCAACTT AATCGCCTTG C AGCACATCC      6660

CCCTTTCGCC AGCTGGCGTA ATAGCGAAGA GGCCCGCACC GATCGCCCTT C CCAACAGTT      6720

GCGCAGCCTG AATGGCGAAT GGCGCGAAAT TGTAAACGTT AATATTTTGT T AAAATTCGC      6780

GTTAAATTTT TGTTAAATCA GCTCATTTTT TAACCAATAG GCCGAAATCG G CAAAATCCC      6840

TTATAAATCA AAAGAATAGA CCGAGATAGG GTTGAGTGTT GTTCCAGTTT G GAACAAGAG      6900

TCCACTATTA AGAACGTGG ACTCCAACGT CAAAGGGCGA AAAACCGTCT A TCAGGGCGA      6960

TGGCCCACTA CGTGAACCAT CACCCTAATC AAGTTTTTTG GGGTCGAGGT G CCGTAAAGC      7020

ACTAAATCGG AACCCTAAAG GGAGCCCCCG ATTTAGAGCT TGACGGGGAA A GCCGGCGAA      7080

CGTGGCGAGA AAGGAAGGGA AGAAAGCGAA AGGAGCGGGC GCTAGGGCGC T GGCAAGTGT      7140

AGCGGTCACG CTGCGCGTAA CCACCACACC CGCCGCGCTT AATGCGCCGC T ACAGGGCGC      7200

GTCCCAGGTG GCACTTTTCG GGGAAATGTG CGCGGAACCC CTATTTGTTT A TTTTTCTAA      7260

ATACATTCAA ATATGTATCC GCTCATGAGA CAATAACCCT GATAAATGCT T CAATAATAT      7320

TGAAAAAGGA AGAGTATGAG TATTCAACAT TTCCGTGTCG CCCTTATTCC C TTTTTTGCG      7380

GCATTTTGCC TTCCTGTTTT TGCTCACCCA GAAACGCTGG TGAAAGTAAA A GATGCTGAA      7440

GATCAGTTGG GTGCACGAGT GGGTTACATC GAACTGGATC TCAACAGCGG T AAGATCCTT      7500

GAGAGTTTTC GCCCCGAAGA ACGTTTTCCA ATGATGAGCA CTTTTAAAGT T CTGCTATGT      7560

GGCGCGGTAT TATCCCGTAT TGACGCCGGG CAAGAGCAAC TCGGTCGCCG C ATACACTAT      7620

TCTCAGAATG ACTTGGTTGA GTACTCACCA GTCACAGAAA AGCATCTTAC G GATGGCATG      7680

ACAGTAAGAG AATTATGCAG TGCTGCCATA ACCATGAGTG ATAACACTGC G GCCAACTTA      7740
```

```
CTTCTGACAA CGATCGGAGG ACCGAAGGAG CTAACCGCTT TTTTGCACAA C ATGGGGAT      7800

CATGTAACTC GCCTTGATCG TTGGGAACCG GAGCTGAATG AAGCCATACC A AACGACGAG     7860

CGTGACACCA CGATGCCTGT AGCAATGGCA ACAACGTTGC GCAAACTATT A ACTGGCGAA     7920

CTACTTACTC TAGCTTCCCG GCAACAATTA ATAGACTGGA TGGAGGCGGA T AAAGTTGCA     7980

GGACCACTTC TGCGCTCGGC CCTTCCGGCT GGCTGGTTTA TTGCTGATAA A TCTGGAGCC    8040

GGTGAGCGTG GGTCTCGCGG TATCATTGCA GCACTGGGGC CAGATGGTAA G CCCTCCCGT    8100

ATCGTAGTTA TCTACACGAC GGGGAGTCAG GCAACTATGG ATGAACGAAA T AGACAGATC    8160

GCTGAGATAG GTGCCTCACT GATTAAGCAT TGGTAACTGT CAGACCAAGT T TACTCATAT    8220

ATACTTTAGA TTGATTTAAA ACTTCATTTT TAATTTAAAA GGATCTAGGT G AAGATCCTT    8280

TTTGATAATC TCATGACCAA AATCCCTTAA CGTGAGTTTT CGTTCCACTG A GCGTCAGAC    8340

CCCGTAGAAA AGATCAAAGG ATCTTCTTGA GATCCTTTTT TTCTGCGCGT A ATCTGCTGC    8400

TTGCAAACAA AAAAACCACC GCTACCAGCG GTGGTTTGTT TGCCGGATCA A GAGCTACCA    8460

ACTCTTTTTC CGAAGGTAAC TGGCTTCAGC AGAGCGCAGA TACCAAATAC T GTCCTTCTA    8520

GTGTAGCCGT AGTTAGGCCA CCACTTCAAG AACTCTGTAG CACCGCCTAC A TACCTCGCT    8580

CTGCTAATCC TGTTACCAGT GGCTGCTGCC AGTGGCGATA AGTCGTGTCT T ACCGGGTTG    8640

GACTCAAGAC GATAGTTACC GGATAAGGCG CAGCGGTCGG GCTGAACGGG G GGTTCGTGC    8700

ACACAGCCCA GCTTGGAGCG AACGACCTAC ACCGAACTGA GATACCTACA G CGTGAGCTA    8760

TGAGAAAGCG CCACGCTTCC CGAAGGGAGA AAGGCGGACA GGTATCCGGT A AGCGGCAGG    8820

GTCGGAACAG GAGAGCGCAC GAGGGAGCTT CCAGGGGGAA ACGCCTGGTA T CTTTATAGT    8880

CCTGTCGGGT TTCGCCACCT CTGACTTGAG CGTCGATTTT TGTGATGCTC G TCAGGGGG     8940

CGGAGCCTAT GGAAAAACGC CAGCAACGCG GCCTTTTTAC GGTTCCTGGC C TTTTGCTGG    9000

CCTTTTGCTC ACATGTTCTT TCCTGCGTTA TCCCCTGATT CTGTGGATAA C CGTATTACC    9060

GCCTTTGAGT GAGCTGATAC CGCTCGCCGC AGCCGAACGA CCGAGCGCAG C GAGTCAGTG    9120

AGCGAGGAAG CGGAAGAGCG CCCAATACGC AAACCGCCTC TCCCCGCGCG T TGGCCGATT    9180

CATTAATGCA GCTGGCACGA CAGGTTTCCC GACTGGAAAG CGGGCAGTGA G CGCAACGCA    9240

ATTAATGTGA GTTAGCTCAC TCATTAGGCA CCCCAGGCTT TACACTTTAT G CTTCCGGCT    9300

CGTATGTTGT GTGGAATTGT GAGCGGATAA CAATTTCACA CAGGAAACAG C TATGACCAT    9360

GATTACGCCA AGCTCGGAAT TAACCCTCAC TAAAGGGAAC AAAAGCTG                   9408

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TTATCTCGAG GGCACTGAAG TCGCTTGATG TGCTGAATT                              39

(2) INFORMATION FOR SEQ ID NO:18:

(i) SEQUENCE CHARACTERISTICS:
        (A) LENGTH: 42 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:18:

| GGGGAAGCTT CTCTAGATTT GGATATATGC CGTGAACAAT TG | 42 |
|---|---|

(2) INFORMATION FOR SEQ ID NO:19:

(i) SEQUENCE CHARACTERISTICS:
        (A) LENGTH: 9335 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:19:

| AGCTTGCATG CCTGCAGGCC GGCCTTAATT AAGCGGCCGC CAGTGTGATG G ATATCTGCA | 60 |
|---|---|
| GAATTCGGCT TGGGGGATCC TCTAGACAAT GATATACATA GATAAAAACC A CTGTTGTAA | 120 |
| CTTGTAAGCC ACTAGCTCAC GTTCTCCATG AGCTCTTCTC TCTGCTGTTT C TTCCTCTGC | 180 |
| TAACTGCGTT ATGATATGAC GTCGTATAAA TAATCTCACA ATACTTCCTT A TTTTCAGCA | 240 |
| TGGCCTCTTT TATGTTTATT TAACAGTAGC AACCAACGCC GCTCGATGTT T CCTTCAAGA | 300 |
| AACGGCCACT CACTATGTGG TGTGCAGAAG AACAAATGTA AGCAGCTCCT A CAGGTACCA | 360 |
| GTAGTCATGT CAGTGTGGAA GCTTTCCAAC CAACGCCTCC TTCGAGGAAC C TGGTCGTGC | 420 |
| TGACATGAAT GTAGGCCATG CAAGCACAAG CACCTAACGC GAATCATCAC G ACGCGCCGT | 480 |
| GTACTGGGCG TTGGTACATC ACACCCCGCG TTTGACCTGA TCGGAAGCAT G CGTGTGTGT | 540 |
| TGGCTGCAGG ACCGGCTATA GGTTTCCTGC ATTGGACAGC AGAAGCCAGT C ATGTTAGGC | 600 |
| ACTCACGCGC TCCTGCCGTT TGATGAATCA TCCGGTCTTT CGTATTGATC A CTAGTTCAC | 660 |
| TACGCTGATA TAGCAAATTT TAAGATGTGA AACCACGAGA CGAGCGATAA A TCTTAGACG | 720 |
| TTACCTATCC ATATGAAGCT TGTGCGAAAA AAAGGCGTGC CGCTGTAGCA T CATTCGTAT | 780 |
| ACACTTTTGT CCCCAAAGAC AGGGATACGA ATCCATGCTC GACAGAACCC T CCCTTCCCT | 840 |
| GCAGATAACG ACACTTAAGT ATAACAAAAG TAGTTGGATT ATTTCAGAAG C AAAATCTCA | 900 |
| CTTTTCGCTG GCCTTTTTGT ACTTTGGTTA CTTGAGTTCA GACAGTGTAT G CTATATTGT | 960 |
| CATGTGCTGC GTAAGGTTTA AATATGGTTC GACAAATATA TCAGTATATC A CTACTTTGT | 1020 |
| TATGGGTGGG GCCTAGCACA AACTTGATAC AGCTAGGATA AAGTTAGAAC G ATGACTGAT | 1080 |
| CTACTGTAAA GCGACACCTG TCCTGTTATG GTAGTTTAAG TCCATTCCTG G ACGACTCCA | 1140 |
| GATCCAGGAT ATGATGCTGT TACATAATGC GATTGTTCAC AATAAAATTG C ATGATGTTC | 1200 |
| TTCTACTCTT TAGGCAGTTT TGTTCAACAG GCAAGTTGCA TAATGCATGT G CATATATGA | 1260 |
| GCAGCATAAT CATCAATTAA TCATAGGTTC GTCATTTTAG TTTCACTCCT T CACATTATT | 1320 |
| CCAGCCCTTG AAGAAAATG TAGCAGTGCT TGCTGTTTAA TAAGTGGCAG A GCTGTTTTC | 1380 |
| ACTCCACCTA CGCTTGTCTA GGACCAAAAT TTTAATCTGT CACTTTGAGC T AAAACTGAA | 1440 |
| GCACCAAACC GCTACAAAAG AACGTAGGAG CTGAATTGTA ACTTGATGGG A TTACTATAG | 1500 |
| CAGTTGCTAC AGTTCTAGCT AGCTACCTTA TTCTATACGC ATCACCCTAA C AACCCGGCT | 1560 |
| GACTGCTGCA TCTGACCCCA CCGTCCCCTG CTCCAAACCA ACTCTCCTTT C CTTGCATGC | 1620 |
| ACTACACCCA CTTCCTGCAG CTATATATAC CACCATATGC CCATCTTATG A AACCATCCA | 1680 |
| CAAGAGGAGA AGAAACAATC AACCAGCAAC ACTCTTCTCT TATAACATAG T ACAGCGAAG | 1740 |
| GAGATCCTGA CTGCTTTGTC AAGGTTCAAT TCTGCTTCCT CTGTTATGTT C TTTATATTA | 1800 |

```
CATGCTCTGA CAAAGCTATA AAGCTTGATA CTGCAGTATA ATATAACAAG T TAGCTACAC    1860

AAGTTTTGTA CTTCAAGTCT TTTAACTATA TGTTGGTGCA ATAAGATTAT G AGTAATCCA    1920

TATGAAGGTG TTGCAAGAGA ACATGAAAGG CAAAGATAAA CGGATGAACC C ATTACTAGC    1980

TTTGGCTGTA TCAGACCAAT AACTTGAAAT GCACTTGTGC TAGCATGCCT A AGTATTAGA    2040

AAAGGTAGCA TGGGAGAATC TATATTATTT TGGCTAACTT CTTTAGTTAC T ATTGATTGA    2100

TGAGAAAGCC TACCATTGCC CATGCCAGCC CTAATGTCCC GGTGACATGA T TGAGCCAGT    2160

ACTATGATTA ATTTACTCTA TTGTTCTCCT TTTTTGAGTG CTGTATAAGA T GTCCTTTTT    2220

TTGAGCCACT CGAGAAGATG TTTACTTAAC TCTAGTGCGC AATGATTGGA G CTCTCAGTG    2280

CAACGCATGT GCTCTGTAAT CTACTGTCAC CACTACTCTG TAGTGTGTGC T TAAACTCTA    2340

AACTATTCCA CGTGGCTAGT AATTACCAAT CATTTACAAC ACTGTTACAT G TGTAGGGCT    2400

GCGATCCATG GTCCGTCCTG TAGAAACCCC AACCCGTGAA ATCAAAAAAC T CGACGGCCT    2460

GTGGGCATTC AGTCTGGATC GCGAAAACTG TGGAATTGAT CAGCGTTGGT G GGAAAGCGC    2520

GTTACAAGAA AGCCGGGCAA TTGCTGTGCC AGGCAGTTTT AACGATCAGT T CGCCGATGC    2580

AGATATTCGT AATTATGCGG GCAACGTCTG GTATCAGCGC GAAGTCTTTA T ACCGAAAGG    2640

TTGGGCAGGC CAGCGTATCG TGCTGCGTTT CGATGCGGTC ACTCATTACG G CAAAGTGTG    2700

GGTCAATAAT CAGGAAGTGA TGGAGCATCA GGGCGGCTAT ACGCCATTTG A AGCCGATGT    2760

CACGCCGTAT GTTATTGCCG GGAAAAGTGT ACGTATCACC GTTTGTGTGA A CAACGAACT    2820

GAACTGGCAG ACTATCCCGC CGGGAATGGT GATTACCGAC GAAAACGGCA A GAAAAAGCA    2880

GTCTTACTTC CATGATTTCT TTAACTATGC CGGAATCCAT CGCAGCGTAA T GCTCTACAC    2940

CACGCCGAAC ACCTGGGTGG ACGATATCAC CGTGGTGACG CATGTCGCGC A AGACTGTAA    3000

CCACGCGTCT GTTGACTGGC AGGTGGTGGC CAATGGTGAT GTCAGCGTTG A ACTGCGTGA    3060

TGCGGATCAA CAGGTGGTTG CAACTGGACA AGGCACTAGC GGGACTTTGC A AGTGGTGAA    3120

TCCGCACCTC TGGCAACCGG GTGAAGGTTA TCTCTATGAA CTGTGCGTCA C AGCCAAAAG    3180

CCAGACAGAG TGTGATATCT ACCCGCTTCG CGTCGGCATC CGGTCAGTGG C AGTGAAGGG    3240

CGAACAGTTC CTGATTAACC ACAAACCGTT CTACTTTACT GGCTTTGGTC G TCATGAAGA    3300

TGCGGACTTA CGTGGCAAAG GATTCGATAA CGTGCTGATG GTGCACGACC A CGCATTAAT    3360

GGACTGGATT GGGGCCAACT CCTACCGTAC CTCGCATTAC CCTTACGCTG A AGAGATGCT    3420

CGACTGGGCA GATGAACATG GCATCGTGGT GATTGATGAA ACTGCTGCTG T CGGCTTTAA    3480

CCTCTCTTTA GGCATTGGTT TCGAAGCGGG CAACAAGCCG AAAGAACTGT A CAGCGAAGA    3540

GGCAGTCAAC GGGGAAACTC AGCAAGCGCA CTTACAGGCG ATTAAAGAGC T GATAGCGCG    3600

TGACAAAAAC CACCCAAGCG TGGTGATGTG GAGTATTGCC AACGAACCGG A TACCCGTCC    3660

GCAAGTGCAC GGGAATATTT CGCCACTGGC GGAAGCAACG CGTAAACTCG A CCCGACGCG    3720

TCCGATCACC TGCGTCAATG TAATGTTCTG CGACGCTCAC ACCGATACCA T CAGCGATCT    3780

CTTTGATGTG CTGTGCCTGA ACCGTTATTA CGGATGGTAT GTCCAAAGCG G CGATTTGGA    3840

AACGGCAGAG AAGGTACTGG AAAAAGAACT TCTGGCCTGG CAGGAGAAAC T GCATCAGCC    3900

GATTATCATC ACCGAATACG GCGTGGATAC GTTAGCCGGG CTGCACTCAA T GTACACCGA    3960

CATGTGGAGT GAAGAGTATC AGTGTGCATG GCTGGATATG TATCACCGCG T CTTTGATCG    4020

CGTCAGCGCC GTCGTCGGTG AACAGGTATG GAATTTCGCC GATTTTGCGA C CTCGCAAGG    4080

CATATTGCGC GTTGGCGGTA ACAAGAAAGG GATCTTCACT CGCGACCGCA A ACCGAAGTC    4140
```

```
GGCGGCTTTT CTGCTGCAAA AACGCTGGAC TGGCATGAAC TTCGGTGAAA A ACCGCAGCA    4200

GGGAGGCAAA CAATGAATCA ACAACTCTCC TGGCGCACCA TCGTCGGCTA C AGCCTCGGG    4260

AATTGCTACC GAGCTTCTCG AGGGCACTGA AGTCGCTTGA TGTGCTGAAT T GTTTGTGAT    4320

GTTGGTGGCG TATTTTGTTT AAATAAGTAA GCATGGCTGT GATTTTATCA T ATGATCGAT    4380

CTTTGGGGTT TTATTTAACA CATTGTAAAA TGTGTATCTA TTAATAACTC A ATGTATAAG    4440

ATGTGTTCAT TCTTCGGTTG CCATAGATCT GCTTATTTGA CCTGTGATGT T TTGACTCCA    4500

AAAACCAAAA TCACAACTCA ATAAACTCAT GGAATATGTC CACCTGTTTC T TGAAGAGTT    4560

CATCTACCAT TCCAGTTGGC ATTTATCAGT GTTGCAGCGG CGCTGTGCTT T GTAACATAA    4620

CAATTGTTCA CGGCATATAT CCAAATCTAG AGAAGCTTAT CGATACCGTC G ACCTCGAGG    4680

GGGGGCCCGG TACCCAATTC GCCCTATAGT GAGTCGTATT ACAATTCACT G GCCGTCGTT    4740

TTACAACGTC GTGACTGGGA AAACCCTGGC GTTACCCAAC TTAATCGCCT T GCAGCACAT    4800

CCCCCTTTCG CCAGAAACGC CGGGCATTT AAATGGCGCG CCGCGATCGC T TGCAGATCT    4860

GCATGGGTGG AGACTTTTCA ACAAAGGGTA ATATCCGGAA ACCTCCTCGG A TTCCATTGC    4920

CCAGCTATCT GTCACTTTAT TGTGAAGATA GTGGAAAAGG AAGGTGGCTC C TACAAATGC    4980

CATCATTGCG ATAAAGGAAA GGCCATCGTT GAAGATGCCT CTGCCGACAG T GGTCCCAAA    5040

GATGGACCCC CACCCACGAG GAGCATCGTG GAAAAGAAG ACGTTCCAAC C ACGTCTTCA    5100

AAGCAAGTGG ATTGATGTGA TCATCGATGG AGACTTTTCA ACAAAGGGTA A TATCCGGAA    5160

ACCTCCTCGG ATTCCATTGC CCAGCTATCT GTCACTTTAT TGTGAAGATA G TGGAAAAGG    5220

AAGGTGGCTC CTACAAATGC CATCATTGCG ATAAAGGAAA GGCCATCGTT G AAGATGCCT    5280

CTGCCGACAG TGGTCCCAAA GATGGACCCC CACCCACGAG GAGCATCGTG G AAAAGAAG    5340

ACGTTCCAAC CACGTCTTCA AAGCAAGTGG ATTGATGTGA TATCTCCACT G ACGTAAGGG    5400

ATGACGCACA ATCCCACTAT CCTTCGCAAG ACCCTTCCTC TATATAAGGA A GTTCATTTC    5460

ATTTGGAGAG AACACGGGGG ACTCTAGAGG ATCCAGCTGA AGGCTCGACA A GGCAGTCCA    5520

CGGAGGAGCT GATATTTGGT GGACAAGCTG TGGATAGGAG CAACCCTATC C CTAATATAC    5580

CAGCACCACC AAGTCAGGGC AATCCCCAGA TCAAGTGCAA AGGTCCGCCT T GTTTCTCCT    5640

CTGTCTCTTG ATCTGACTAA TCTTGGTTTA TGATTCGTTG AGTAATTTTG G GGAAAGCTC    5700

CTTTGCTGCT CCACACATGT CCATTCGAAT TTTACCGTGT TTAGCAAGGG C GAAAAGTTT    5760

GCATCTTGAT GATTTAGCTT GACTATGCGA TTGCTTTCCT GGACCCGTGC A GCTGCGGAC    5820

GGATCTGGGG CCATTTGTTC CAGGCACGGG ATAAGCATTC AGCCATGGCC C AGAACGAC    5880

GCCCGGCCGA CATCCGCCGT GCCACCGAGG CGGACATGCC GGCGGTCTGC A CCATCGTCA    5940

ACCACTACAT CGAGACAAGC ACGGTCAACT TCCGTACCGA GCCGCAGGAA C CGCAGGAGT    6000

GGACGGACGA CCTCGTCCGT CTGCGGGAGC GCTATCCCTG GCTCGTCGCC G AGGTGGACG    6060

GCGAGGTCGC CGGCATCGCC TACGCGGGCC CCTGGAAGGC ACGAACGCC T ACGACTGGA    6120

CGGCCGAGTC GACCGTGTAC GTCTCCCCCC GCCACCAGCG GACGGACTG G GCTCCACGC    6180

TCTACACCCA CCTGCTGAAG TCCCTGGAGG CACAGGGCTT CAAGAGCGTG G TCGCTGTCA    6240

TCGGGCTGCC CAACGACCCG AGCGTGCGCA TGCACGAGGC GCTCGGATAT G CCCCCGCG    6300

GCATGCTGCG GGCGGCCGGC TTCAAGCACG GGAACTGGCA TGACGTGGGT T TCTGGCAGC    6360

TGGACTTCAG CCTGCCGGTA CCGCCCCGTC CGGTCCTGCC CGTCACCGAA A TCTGATGAG    6420

ATCTGAGCTC GAATTTCCCC GATCGTTCAA ACATTTGGCA ATAAAGTTTC T TAAGATTGA    6480

ATCCTGTTGC CGGTCTTGCG ATGATTATCA TATAATTTCT GTTGAATTAC G TTAAGCATG    6540
```

-continued

| | |
|---|---|
| TAATAATTAA CATGTAATGC ATGACGTTAT TTATGAGATG GGTTTTTATG A TTAGAGTCC | 6600 |
| CGCAATTATA CATTTAATAC GCGATAGAAA ACAAAATATA GCGCGCAAAC T AGGATAAAT | 6660 |
| TATCGCGCGC GGTGTCATCT ATGTTACTAG ATCGATCGGG AATTCACTGG C CGTCGTTTT | 6720 |
| ACAACGTCGT GACTGGGAAA ACCCTGGCGT TACCCAACTT AATCGCCTTG C AGCACATCC | 6780 |
| CCCTTTCGCC AGCTGGCGTA ATAGCGAAGA GGCCCGCACC GATCGCCCTT C CCAACAGTT | 6840 |
| GCGCAGCCTG AATGGCGAAT GGCGCCTGAT GCGGTATTTT CTCCTTACGC A TCTGTGCGG | 6900 |
| TATTTCACAC CGCATATGGT GCACTCTCAG TACAATCTGC TCTGATGCCG C ATAGTTAAG | 6960 |
| CCAGCCCCGA CACCCGCCAA CACCCGCTGA CGCGCCCTGA CGGGCTTGTC T GCTCCCGGC | 7020 |
| ATCCGCTTAC AGACAAGCTG TGACCGTCTC CGGGAGCTGC ATGTGTCAGA G GTTTTCACC | 7080 |
| GTCATCACCG AAACGCGCGA GACGAAAGGG CCTCGTGATA CGCCTATTTT T ATAGGTTAA | 7140 |
| TGTCATGATA ATAATGGTTT CTTAGACGTC AGGTGGCACT TTTCGGGGAA A TGTGCGCGG | 7200 |
| AACCCCTATT TGTTTATTTT TCTAAATACA TTCAAATATG TATCCGCTCA T GAGACAATA | 7260 |
| ACCCTGATAA ATGCTTCAAT AATATTGAAA AAGGAAGAGT ATGAGTATTC A ACATTTCCG | 7320 |
| TGTCGCCCTT ATTCCCTTTT TTGCGGCATT TTGCCTTCCT GTTTTTGCTC A CCCAGAAAC | 7380 |
| GCTGGTGAAA GTAAAAGATG CTGAAGATCA GTTGGGTGCA CGAGTGGGTT A CATCGAACT | 7440 |
| GGATCTCAAC AGCGGTAAGA TCCTTGAGAG TTTTCGCCCC GAAGAACGTT T TCCAATGAT | 7500 |
| GAGCACTTTT AAAGTTCTGC TATGTGGCGC GGTATTATCC CGTATTGACG C CGGGCAAGA | 7560 |
| GCAACTCGGT CGCCGCATAC ACTATTCTCA GAATGACTTG GTTGAGTACT C ACCAGTCAC | 7620 |
| AGAAAAGCAT CTTACGGATG GCATGACAGT AAGAGAATTA TGCAGTGCTG C CATAACCAT | 7680 |
| GAGTGATAAC ACTGCGGCCA ACTTACTTCT GACAACGATC GGAGGACCGA A GGAGCTAAC | 7740 |
| CGCTTTTTTG CACAACATGG GGATCATGT AACTCGCCTT GATCGTTGGG A ACCGGAGCT | 7800 |
| GAATGAAGCC ATACCAAACG ACGAGCGTGA CACCACGATG CCTGTAGCAA T GGCAACAAC | 7860 |
| GTTGCGCAAA CTATTAACTG GCGAACTACT TACTCTAGCT TCCCGGCAAC A ATTAATAGA | 7920 |
| CTGGATGGAG GCGGATAAAG TTGCAGGACC ACTTCTGCGC TCGGCCCTTC C GGCTGGCTG | 7980 |
| GTTTATTGCT GATAAATCTG GAGCCGGTGA GCGTGGGTCT CGCGGTATCA T TGCAGCACT | 8040 |
| GGGGCCAGAT GGTAAGCCCT CCCGTATCGT AGTTATCTAC ACGACGGGGA G TCAGGCAAC | 8100 |
| TATGGATGAA CGAAATAGAC AGATCGCTGA GATAGGTGCC TCACTGATTA A GCATTGGTA | 8160 |
| ACTGTCAGAC CAAGTTTACT CATATATACT TTAGATTGAT TTAAAACTTC A TTTTTAATT | 8220 |
| TAAAAGGATC TAGGTGAAGA TCCTTTTTGA TAATCTCATG ACCAAAATCC C TTAACGTGA | 8280 |
| GTTTTCGTTC CACTGAGCGT CAGACCCCGT AGAAAAGATC AAAGGATCTT C TTGAGATCC | 8340 |
| TTTTTTTCTG CGCGTAATCT GCTGCTTGCA AACAAAAAAA CCACCGCTAC C AGCGGTGGT | 8400 |
| TTGTTTGCCG GATCAAGAGC TACCAACTCT TTTTCCGAAG GTAACTGGCT T CAGCAGAGC | 8460 |
| GCAGATACCA AATACTGTCC TTCTAGTGTA GCCGTAGTTA GGCCACCACT T CAAGAACTC | 8520 |
| TGTAGCACCG CCTACATACC TCGCTCTGCT AATCCTGTTA CCAGTGGCTG C TGCCAGTGG | 8580 |
| CGATAAGTCG TGTCTTACCG GGTTGGACTC AAGACGATAG TTACCGGATA A GGCGCAGCG | 8640 |
| GTCGGGCTGA ACGGGGGGTT CGTGCACACA GCCCAGCTTG GAGCGAACGA C CTACACCGA | 8700 |
| ACTGAGATAC CTACAGCGTG AGCATTGAGA AAGCGCCACG CTTCCCGAAG G GAGAAAGGC | 8760 |
| GGACAGGTAT CCGGTAAGCG GCAGGGTCGG AACAGGAGAG CGCACGAGGG A GCTTCCAGG | 8820 |
| GGGAAACGCC TGGTATCTTT ATAGTCCTGT CGGGTTTCGC CACCTCTGAC T TGAGCGTCG | 8880 |

-continued

```
ATTTTTGTGA TGCTCGTCAG GGGGGCGGAG CCTATGGAAA AACGCCAGCA A CGCGGCCTT    8940

TTTACGGTTC CTGGCCTTTT GCTGGCCTTT TGCTCACATG TTCTTTCCTG C GTTATCCCC    9000

TGATTCTGTG GATAACCGTA TTACCGCCTT TGAGTGAGCT GATACCGCTC G CCGCAGCCG    9060

AACGACCGAG CGCAGCGAGT CAGTGAGCGA GGAAGCGGAA GAGCGCCCAA T ACGCAAACC    9120

GCCTCTCCCC GCGCGTTGGC CGATTCATTA ATGCAGCTGG CACGACAGGT T TCCCGACTG    9180

GAAAGCGGGC AGTGAGCGCA ACGCAATTAA TGTGAGTTAG CTCACTCATT A GGCACCCCA    9240

GGCTTTACAC TTTATGCTTC CGGCTCGTAT GTTGTGTGGA ATTGTGAGCG G ATAACAATT    9300

TCACACAGGA AACAGCTATG ACCATGATTA CGCCA                                 9335
```

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
GGGGGATCCT CTAGACAATG ATATACATAG ATAAAAACC                             39
```

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GGGAGATCTC CTTCGCTGTA CTATGTTATA AGAGAAGAG                             39
```

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
GGGGGATCCT GACTGCTTTG TCAAGGTTCA ATTCTGCTT                             39
```

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
GGGCCATGGA TCGCAGCCCT ACACATGTAA CAGTGTTGT                             39
```

(2) INFORMATION FOR SEQ ID NO:24:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

AAAGAGCTCT GAGGGCACTG AAGTCGCTTG ATGTGC                                     36

(2) INFORMATION FOR SEQ ID NO:25:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

GGGGAATTCT TGGATATATG CCGTGAACAA TTGTTATGTT AC                              42

(2) INFORMATION FOR SEQ ID NO:26:

(i) SEQUENCE CHARACTERISTICS:
            (A) LENGTH: 5897 base pairs
            (B) TYPE: nucleic acid
            (C) STRANDEDNESS: double
            (D) TOPOLOGY: circular (ii) MOLECULE TYPE: DNA (xi) SEQUENCE DESCRIPTION: SEQ ID NO:26:

AGCTTGCATG CCTGCAGATC TGCATGGGTG GAGACTTTTC AACAAAGGGT A ATATCCGGA          60

AACCTCCTCG GATTCCATTG CCCAGCTATC TGTCACTTTA TTGTGAAGAT A GTGGAAAAG         120

GAAGGTGGCT CCTACAAATG CCATCATTGC GATAAAGGAA AGGCCATCGT T GAAGATGCC         180

TCTGCCGACA GTGGTCCCAA AGATGGACCC CCACCCACGA GGAGCATCGT G GAAAAAGAA         240

GACGTTCCAA CCACGTCTTC AAAGCAAGTG GATTGATGTG ATCATCGATG G AGACTTTTC         300

AACAAAGGGT AATATCCGGA AACCTCCTCG GATTCCATTG CCCAGCTATC T GTCACTTTA         360

TTGTGAAGAT AGTGGAAAAG GAAGGTGGCT CCTACAAATG CCATCATTGC G ATAAAGGAA         420

AGGCCATCGT TGAAGATGCC TCTGCCGACA GTGGTCCCAA AGATGGACCC C CACCCACGA         480

GGAGCATCGT GGAAAAAGAA GACGTTCCAA CCACGTCTTC AAAGCAAGTG G ATTGATGTG         540

ATATCTCCAC TGACGTAAGG GATGACGCAC AATCCCACTA TCCTTCGCAA G ACCCTTCCT         600

CTATATAAGG AAGTTCATTT CATTTGGAGA GAACACGGGG GACTCTAGAG G ATCCAGCTG         660

AAGGCTCGAC AAGGCAGTCC ACGGAGGAGC TGATATTTGG TGGACAAGCT G TGGATAGGA         720

GCAACCCTAT CCCTAATATA CCAGCACCAC CAAGTCAGGG CAATCCCCAG A TCAAGTGCA         780

AAGGTCCGCC TTGTTTCTCC TCTGTCTCTT GATCTGACTA ATCTTGGTTT A TGATTCGTT         840

GAGTAATTTT GGGGAAAGCT CCTTTGCTGC TCCACACATG TCCATTCGAA T TTTACCGTG         900

TTTAGCAAGG GCGAAAAGTT TGCATCTTGA TGATTTAGCT TGACTATGCG A TTGCTTTCC         960

TGGACCCGTG CAGCTGCGGA CGGATCTGGG GCCATTTGTT CCAGGCACGG G ATAAGCATT        1020

CAGCCATGGT CCGTCCTGTA GAAACCCCAA CCCGTGAAAT CAAAAAACTC G ACGGCCTGT        1080

GGGCATTCAG TCTGGATCGC GAAAACTGTG GAATTGATCA GCGTTGGTGG G AAAGCGCGT        1140

TACAAGAAAG CCGGGCAATT GCTGTGCCAG GCAGTTTTAA CGATCAGTTC G CCGATGCAG        1200

```
ATATTCGTAA TTATGCGGGC AACGTCTGGT ATCAGCGCGA AGTCTTTATA C CGAAAGGTT      1260

GGGCAGGCCA GCGTATCGTG CTGCGTTTCG ATGCGGTCAC TCATTACGGC A AAGTGTGG      1320

TCAATAATCA GGAAGTGATG GAGCATCAGG GCGGCTATAC GCCATTTGAA G CCGATGTCA     1380

CGCCGTATGT TATTGCCGGG AAAAGTGTAC GTATCACCGT TTGTGTGAAC A ACGAACTGA    1440

ACTGGCAGAC TATCCCGCCG GGAATGGTGA TTACCGACGA AAACGGCAAG A AAAAGCAGT    1500

CTTACTTCCA TGATTTCTTT AACTATGCCG GAATCCATCG CAGCGTAATG C TCTACACCA   1560

CGCCGAACAC CTGGGTGGAC GATATCACCG TGGTGACGCA TGTCGCGCAA G ACTGTAACC   1620

ACGCGTCTGT TGACTGGCAG GTGGTGGCCA ATGGTGATGT CAGCGTTGAA C TGCGTGATG   1680

CGGATCAACA GGTGGTTGCA ACTGGACAAG GCACTAGCGG GACTTTGCAA G TGGTGAATC   1740

CGCACCTCTG GCAACCGGGT GAAGGTTATC TCTATGAACT GTGCGTCACA G CCAAAAGCC   1800

AGACAGAGTG TGATATCTAC CCGCTTCGCG TCGGCATCCG GTCAGTGGCA G TGAAGGGCG   1860

AACAGTTCCT GATTAACCAC AAACCGTTCT ACTTTACTGG CTTTGGTCGT C ATGAAGATG   1920

CGGACTTACG TGGCAAAGGA TTCGATAACG TGCTGATGGT GCACGACCAC G CATTAATGG   1980

ACTGGATTGG GGCCAACTCC TACCGTACCT CGCATTACCC TTACGCTGAA G AGATGCTCG   2040

ACTGGGCAGA TGAACATGGC ATCGTGGTGA TTGATGAAAC TGCTGCTGTC G GCTTTAACC   2100

TCTCTTTAGG CATTGGTTTC GAAGCGGGCA ACAAGCCGAA AGAACTGTAC A GCGAAGAGG   2160

CAGTCAACGG GGAAACTCAG CAAGCGCACT TACAGGCGAT TAAAGAGCTG A TAGCGCGTG   2220

ACAAAAACCA CCCAAGCGTG GTGATGTGGA GTATTGCCAA CGAACCGGAT A CCCGTCCGC   2280

AAGTGCACGG GAATATTTCG CCACTGGCGG AAGCAACGCG TAAACTCGAC C CGACGCGTC   2340

CGATCACCTG CGTCAATGTA ATGTTCTGCG ACGCTCACAC CGATACCATC A GCGATCTCT   2400

TTGATGTGCT GTGCCTGAAC CGTTATTACG GATGGTATGT CCAAAGCGGC G ATTTGGAAA   2460

CGGCAGAGAA GGTACTGGAA AAAGAACTTC TGGCCTGGCA GGAGAAACTG C ATCAGCCGA   2520

TTATCATCAC CGAATACGGC GTGGATACGT TAGCCGGGCT GCACTCAATG T ACACCGACA   2580

TGTGGAGTGA AGAGTATCAG TGTGCATGGC TGGATATGTA TCACCGCGTC T TTGATCGCG   2640

TCAGCGCCGT CGTCGGTGAA CAGGTATGGA ATTTCGCCGA TTTTGCGACC T CGCAAGGCA   2700

TATTGCGCGT TGGCGGTAAC AAGAAAGGGA TCTTCACTCG CGACCGCAAA C CGAAGTCGG   2760

CGGCTTTTCT GCTGCAAAAA CGCTGGACTG GCATGAACTT CGGTGAAAAA C CGCAGCAGG   2820

GAGGCAAACA ATGAATCAAC AACTCTCCTG GCGCACCATC GTCGGCTACA G CCTCGGTGG   2880

GGAATTGGAG AGCTCTGAGG GCACTGAAGT CGCTTGATGT GCTGAATTGT T TGTGATGTT   2940

GGTGGCGTAT TTTGTTTAAA TAAGTAAGCA TGGCTGTGAT TTTATCATAT G ATCGATCTT   3000

TGGGGTTTTA TTTAACACAT TGTAAAATGT GTATCTATTA ATAACTCAAT G TATAAGATG   3060

TGTTCATTCT TCGGTTGCCA TAGATCTGCT TATTTGACCT GTGATGTTTT G ACTCCAAAA   3120

ACCAAAATCA CAACTCAATA AACTCATGGA ATATGTCCAC CTGTTTCTTG A AGAGTTCAT   3180

CTACCATTCC AGTTGGCATT TATCAGTGTT GCAGCGGCGC TGTGCTTTGT A ACATAACAA   3240

TTGTTCACGG CATATATCCA AGAATTCACT GGCCGTCGTT TTACAACGTC G TGACTGGGA   3300

AAACCCTGGC GTTACCCAAC TTAATCGCCT TGCAGCACAT CCCCCTTTCG C CAGCTGGCG   3360

TAATAGCGAA GAGGCCCGCA CCGATCGCCC TTCCCAACAG TTGCGCAGCC T GAATGGCGA   3420

ATGGCGCCTG ATGCGGTATT TTCTCCTTAC GCATCTGTGC GGTATTTCAC A CCGCATATG   3480

GTGCACTCTC AGTACAATCT GCTCTGATGC CGCATAGTTA AGCCAGCCCC G ACACCCGCC   3540
```

-continued

```
AACACCCGCT GACGCGCCCT GACGGGCTTG TCTGCTCCCG GCATCCGCTT A CAGACAAGC    3600
TGTGACCGTC TCCGGGAGCT GCATGTGTCA GAGGTTTTCA CCGTCATCAC C GAAACGCGC    3660
GAGACGAAAG GGCCTCGTGA TACGCCTATT TTTATAGGTT AATGTCATGA T AATAATGGT    3720
TTCTTAGACG TCAGGTGGCA CTTTTCGGGG AAATGTGCGC GGAACCCCTA T TTGTTTATT    3780
TTTCTAAATA CATTCAAATA TGTATCCGCT CATGAGACAA TAACCCTGAT A AATGCTTCA    3840
ATAATATTGA AAAAGGAAGA GTATGAGTAT TCAACATTTC CGTGTCGCCC T TATTCCCTT    3900
TTTTGCGGCA TTTTGCCTTC CTGTTTTTGC TCACCCAGAA ACGCTGGTGA A AGTAAAAGA    3960
TGCTGAAGAT CAGTTGGGTG CACGAGTGGG TTACATCGAA CTGGATCTCA A CAGCGGTAA    4020
GATCCTTGAG AGTTTTCGCC CCGAAGAACG TTTTCCAATG ATGAGCACTT T TAAAGTTCT    4080
GCTATGTGGC GCGGTATTAT CCCGTATTGA CGCCGGGCAA GAGCAACTCG G TCGCCGCAT    4140
ACACTATTCT CAGAATGACT TGGTTGAGTA CTCACCAGTC ACAGAAAAGC A TCTTACGGA    4200
TGGCATGACA GTAAGAGAAT TATGCAGTGC TGCCATAACC ATGAGTGATA A CACTGCGGC    4260
CAACTTACTT CTGACAACGA TCGGAGGACC GAAGGAGCTA ACCGCTTTTT T GCACAACAT    4320
GGGGGATCAT GTAACTCGCC TTGATCGTTG GGAACCGGAG CTGAATGAAG C CATACCAAA    4380
CGACGAGCGT GACACCACGA TGCCTGTAGC AATGGCAACA ACGTTGCGCA A ACTATTAAC    4440
TGGCGAACTA CTTACTCTAG CTTCCCGGCA ACAATTAATA GACTGGATGG A GGCGGATAA    4500
AGTTGCAGGA CCACTTCTGC GCTCGGCCCT TCCGGCTGGC TGGTTTATTG C TGATAAATC    4560
TGGAGCCGGT GAGCGTGGGT CTCGCGGTAT CATTGCAGCA CTGGGGCCAG A TGGTAAGCC    4620
CTCCCGTATC GTAGTTATCT ACACGACGGG GAGTCAGGCA ACTATGGATG A ACGAAATAG    4680
ACAGATCGCT GAGATAGGTG CCTCACTGAT TAAGCATTGG TAACTGTCAG A CCAAGTTTA    4740
CTCATATATA CTTTAGATTG ATTTAAAACT TCATTTTTAA TTTAAAAGGA T CTAGGTGAA    4800
GATCCTTTTT GATAATCTCA TGACCAAAAT CCCTTAACGT GAGTTTTCGT T CCACTGAGC    4860
GTCAGACCCC GTAGAAAAGA TCAAAGGATC TTCTTGAGAT CCTTTTTTTC T GCGCGTAAT    4920
CTGCTGCTTG CAAACAAAAA AACCACCGCT ACCAGCGGTG GTTTGTTTGC C GGATCAAGA    4980
GCTACCAACT CTTTTTCCGA AGGTAACTGG CTTCAGCAGA GCGCAGATAC C AAATACTGT    5040
CCTTCTAGTG TAGCCGTAGT TAGGCCACCA CTTCAAGAAC TCTGTAGCAC C GCCTACATA    5100
CCTCGCTCTG CTAATCCTGT TACCAGTGGC TGCTGCCAGT GGCGATAAGT C GTGTCTTAC    5160
CGGGTTGGAC TCAAGACGAT AGTTACCGGA TAAGGCGCAG CGGTCGGGCT G AACGGGGGG    5220
TTCGTGCACA CAGCCCAGCT TGGAGCGAAC GACCTACACC GAACTGAGAT A CCTACAGCG    5280
TGAGCATTGA GAAAGCGCCA CGCTTCCCGA AGGGAGAAAG GCGGACAGGT A TCCGGTAAG    5340
CGGCAGGGTC GGAACAGGAG AGCGCACGAG GGAGCTTCCA GGGGGAAACG C CTGGTATCT    5400
TTATAGTCCT GTCGGGTTTC GCCACCTCTG ACTTGAGCGT CGATTTTGT G ATGCTCGTC    5460
AGGGGGGCGG AGCCTATGGA AAAACGCCAG CAACGCGGCC TTTTTACGGT T CCTGGCCTT    5520
TTGCTGGCCT TTTGCTCACA TGTTCTTTCC TGCGTTATCC CCTGATTCTG T GGATAACCG    5580
TATTACCGCC TTTGAGTGAG CTGATACCGC TCGCCGCAGC CGAACGACCG A GCGCAGCGA    5640
GTCAGTGAGC GAGGAAGCGG AAGAGCGCCC AATACGCAAA CCGCCTCTCC C CGCGCGTTG    5700
GCCGATTCAT TAATGCAGCT GGCACGACAG GTTTCCCGAC TGGAAAGCGG G CAGTGAGCG    5760
CAACGCAATT AATGTGAGTT AGCTCACTCA TTAGGCACCC CAGGCTTTAC A CTTTATGCT    5820
TCCGGCTCGT ATGTTGTGTG GAATTGTGAG CGGATAACAA TTTCACACAG G AAACAGCTA    5880
TGACCATGAT TACGCCA                                                    5897
```

(2) INFORMATION FOR SEQ ID NO:27:

(i) SEQUENCE CHARACTERISTICS:
        (A) LENGTH: 6898 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:27:

```
AGCTTGCATG CCTGCAGTGC AGCGTGACCC GGTCGTGCCC CTCTCTAGAG A TAATGAGCA     60
TTGCATGTCT AAGTTATAAA AAATTACCAC ATATTTTTTT TGTCACACTT G TTTGAAGTG    120
CAGTTTATCT ATCTTTATAC ATATATTTAA ACTTTAATCT ACGAATAATA T AATCTATAG    180
TACTACAATA ATATCAGTGT TTTAGAGAAT CATATAAATG AACAGTTAGA C ATGGTCTAA    240
AGGACAATTG AGTATTTTGA CAACAGGACT CTACAGTTTT ATCTTTTTAG T GTGCATGTG    300
TTCTCCTTTT TTTTTGCAAA TAGCTTCACC TATATAATAC TTCATCCATT T TATTAGTAC    360
ATCCATTTAG GGTTTAGGGT TAATGGTTTT TATAGACTAA TTTTTTTAGT A CATCTATTT    420
TATTCTATTT TAGCCTCTAA ATTAAGAAAA CTAAAACTCT ATTTTAGTTT T TTTATTTAA    480
TAATTTAGAT ATAAAATAGA ATAAAATAAA GTGACTAAAA ATTAAACAAA T ACCCTTTAA    540
GAAATTAAAA AAACTAAGGA AACATTTTTC TTGTTTCGAG TAGATAATGC C AGCCTGTTA    600
AACGCCGTCG ACGAGTCTAA CGGACACCAA CCAGCGAACC AGCAGCGTCG C GTCGGGCCA    660
AGCGAAGCAG ACGGCACGGC ATCTCTGTCG CTGCCTCTGG ACCCCTCTCG A GAGTTCCGC    720
TCCACCGTTG GACTTGCTCC GCTGTCGGCA TCCAGAAATT GCGTGGCGGA G CGGCAGACG    780
TGAGCCGGCA CGGCAGGCGG CCTCCTCCTC CTCTCACGGC ACGGCAGCTA C GGGGGATTC    840
CTTTCCCACC GCTCCTTCGC TTTCCCTTCC TCGCCCGCCG TAATAAATAG A CACCCCCTC    900
CACACCCTCT TTCCCCAACC TCGTGTTGTT CGGAGCGCAC ACACACACAA C CAGATCTCC    960
CCCAAATCCA CCCGTCGGCA CCTCCGCTTC AAGGTACGCC GCTCGTCCTC C CCCCCCCCC   1020
CCTCTCTACC TTCTCTAGAT CGGCGTTCCG GTCCATGCAT GGTTAGGGCC C GGTAGTTCT   1080
ACTTCTGTTC ATGTTTGTGT TAGATCCGTG TTTGTGTTAG ATCCGTGCTG C TAGCGTTCG   1140
TACACGGATG CGACCTGTAC GTCAGACACG TTCTGATTGC TAACTTGCCA G TGTTTCTCT   1200
TTGGGGAATC CTGGGATGGC TCTAGCCGTT CCGCAGACGG GATCGATTTC A TGATTTTTT   1260
TTGTTTCGTT GCATAGGGTT TGGTTTGCCC TTTTCCTTTA TTTCAATATA T GCCGTGCAC   1320
TTGTTTGTCG GGTCATCTTT TCATGCTTTT TTTTGTCTTG GTTGTGATGA T GTGGTCTGG   1380
TTGGGCGGTC GTTCTAGATC GGAGTAGAAT TCTGTTTCAA ACTACCTGGT G GATTTATTA   1440
ATTTTGGATC TGTATGTGTG TGCCATACAT ATTCATAGTT ACGAATTGAA G ATGATGGAT   1500
GGAAATATCG ATCTAGGATA GGTATACATG TTGATGCGGG TTTTACTGAT G CATATACAG   1560
AGATGCTTTT TGTTCGCTTG GTTGTGATGA TGTGGTGTGG TTGGGCGGTC G TTCATTCGT   1620
TCTAGATCGG AGTAGAATAC TGTTTCAAAC TACCTGGTGT ATTTATTAAT T TTGGAACTG   1680
TATGTGTGTG TCATACATCT TCATAGTTAC GAGTTTAAGA TGGATGGAAA T ATCGATCTA   1740
GGATAGGTAT ACATGTTGAT GTGGGTTTTA CTGATGCATA TACATGATGG C ATATGCAGC   1800
ATCTATTCAT ATGCTCTAAC CTTGAGTACC TATCTATTAT AATAAACAAG T ATGTTTTAT   1860
AATTATTTTG ATCTTGATAT ACTTGGATGA TGGCATATGC AGCAGCTATA T GTGGATTTT   1920
TTTAGCCCTG CCTTCATACG CTATTTATTT GCTTGGTACT GTTTCTTTTG T CGATGCTCA   1980
```

```
CCCTGTTGTT TGGTGTTACT TCTGCAGGGT ACCCCCGGGG TCGACCATGG T CCGTCCTGT      2040

AGAAACCCCA ACCCGTGAAA TCAAAAAACT CGACGGCCTG TGGGCATTCA G TCTGGATCG      2100

CGAAAACTGT GGAATTGATC AGCGTTGGTG GGAAAGCGCG TTACAAGAAA G CCGGGCAAT      2160

TGCTGTGCCA GGCAGTTTTA ACGATCAGTT CGCCGATGCA GATATTCGTA A TTATGCGGG      2220

CAACGTCTGG TATCAGCGCG AAGTCTTTAT ACCGAAAGGT TGGGCAGGCC A GCGTATCGT      2280

GCTGCGTTTC GATGCGGTCA CTCATTACGG CAAAGTGTGG GTCAATAATC A GGAAGTGAT      2340

GGAGCATCAG GGCGGCTATA CGCCATTTGA AGCCGATGTC ACGCCGTATG T TATTGCCGG      2400

GAAAAGTGTA CGTATCACCG TTTGTGTGAA CAACGAACTG AACTGGCAGA C TATCCCGCC      2460

GGGAATGGTG ATTACCGACG AAAACGGCAA GAAAAAGCAG TCTTACTTCC A TGATTTCTT      2520

TAACTATGCC GGAATCCATC GCAGCGTAAT GCTCTACACC ACGCCGAACA C CTGGGTGGA      2580

CGATATCACC GTGGTGACGC ATGTCGCGCA AGACTGTAAC CACGCGTCTG T TGACTGGCA      2640

GGTGGTGGCC AATGGTGATG TCAGCGTTGA ACTGCGTGAT GCGGATCAAC A GGTGGTTGC      2700

AACTGGACAA GGCACTAGCG GGACTTTGCA AGTGGTGAAT CCGCACCTCT G GCAACCGGG      2760

TGAAGGTTAT CTCTATGAAC TGTGCGTCAC AGCCAAAAGC CAGACAGAGT G TGATATCTA      2820

CCCGCTTCGC GTCGGCATCC GGTCAGTGGC AGTGAAGGGC GAACAGTTCC T GATTAACCA      2880

CAAACCGTTC TACTTTACTG GCTTTGGTCG TCATGAAGAT GCGGACTTAC G TGGCAAAGG      2940

ATTCGATAAC GTGCTGATGG TGCACGACCA CGCATTAATG GACTGGATTG G GGCCAACTC      3000

CTACCGTACC TCGCATTACC CTTACGCTGA AGAGATGCTC GACTGGGCAG A TGAACATGG      3060

CATCGTGGTG ATTGATGAAA CTGCTGCTGT CGGCTTTAAC CTCTCTTTAG G CATTGGTTT      3120

CGAAGCGGGC AACAAGCCGA AGAACTGTA CAGCGAAGAG GCAGTCAACG G GGAAACTCA      3180

GCAAGCGCAC TTACAGGCGA TTAAAGAGCT GATAGCGCGT GACAAAAACC A CCCAAGCGT      3240

GGTGATGTGG AGTATTGCCA ACGAACCGGA TACCCGTCCG CAAGTGCACG G GAATATTTC      3300

GCCACTGGCG GAAGCAACGC GTAAACTCGA CCCGACGCGT CCGATCACCT G CGTCAATGT      3360

AATGTTCTGC GACGCTCACA CCGATACCAT CAGCGATCTC TTTGATGTGC T GTGCCTGAA      3420

CCGTTATTAC GGATGGTATG TCCAAAGCGG CGATTTGGAA ACGGCAGAGA A GGTACTGGA      3480

AAAAGAACTT CTGGCCTGGC AGGAGAAACT GCATCAGCCG ATTATCATCA C CGAATACGG      3540

CGTGGATACG TTAGCCGGGC TGCACTCAAT GTACACCGAC ATGTGGAGTG A AGAGTATCA      3600

GTGTGCATGG CTGGATATGT ATCACCGCGT CTTTGATCGC GTCAGCGCCG T CGTCGGTGA      3660

ACAGGTATGG AATTTCGCCG ATTTTGCGAC CTCGCAAGGC ATATTGCGCG T TGGCGGTAA      3720

CAAGAAAGGG ATCTTCACTC GCGACCGCAA ACCGAAGTCG GCGGCTTTTC T GCTGCAAAA      3780

ACGCTGGACT GGCATGAACT TCGGTGAAAA ACCGCAGCAG GGAGGCAAAC A ATGAATCAA      3840

CAACTCTCCT GGCGCACCAT CGTCGGCTAC AGCCTCGGTG GGAATTGGA G AGCTCTGAG      3900

GGCACTGAAG TCGCTTGATG TGCTGAATTG TTTGTGATGT TGGTGGCGTA T TTTGTTTAA      3960

ATAAGTAAGC ATGGCTGTGA TTTTATCATA TGATCGATCT TTGGGGTTTT A TTTAACACA      4020

TTGTAAAATG TGTATCTATT AATAACTCAA TGTATAAGAT GTGTTCATTC T TCGGTTGCC      4080

ATAGATCTGC TTATTTGACC TGTGATGTTT TGACTCCAAA AACCAAAATC A CAACTCAAT      4140

AAACTCATGG AATATGTCCA CCTGTTTCTT GAAGAGTTCA TCTACCATTC C AGTTGGCAT      4200

TTATCAGTGT TGCAGCGGCG CTGTGCTTTG TAACATAACA ATTGTTCACG G CATATATCC      4260

AAGAATTCAC TGGCCGTCGT TTTACAACGT CGTGACTGGG AAAACCCTGG C GTTACCCAA      4320
```

-continued

| | | | | |
|---|---|---|---|---|
| CTTAATCGCC | TTGCAGCACA | TCCCCCTTTC | GCCAGCTGGC | GTAATAGCGA A GAGGCCCGC 4380 |
| ACCGATCGCC | CTTCCCAACA | GTTGCGCAGC | CTGAATGGCG | AATGGCGCCT G ATGCGGTAT 4440 |
| TTTCTCCTTA | CGCATCTGTG | CGGTATTTCA | CACCGCATAT | GGTGCACTCT C AGTACAATC 4500 |
| TGCTCTGATG | CCGCATAGTT | AAGCCAGCCC | CGACACCCGC | CAACACCCGC T GACGCGCCC 4560 |
| TGACGGGCTT | GTCTGCTCCC | GGCATCCGCT | TACAGACAAG | CTGTGACCGT C TCCGGGAGC 4620 |
| TGCATGTGTC | AGAGGTTTTC | ACCGTCATCA | CCGAAACGCG | CGAGACGAAA G GGCCTCGTG 4680 |
| ATACGCCTAT | TTTTATAGGT | TAATGTCATG | ATAATAATGG | TTTCTTAGAC G TCAGGTGGC 4740 |
| ACTTTTCGGG | GAAATGTGCG | CGGAACCCCT | ATTTGTTTAT | TTTTCTAAAT A CATTCAAAT 4800 |
| ATGTATCCGC | TCATGAGACA | ATAACCCTGA | TAAATGCTTC | AATAATATTG A AAAAGGAAG 4860 |
| AGTATGAGTA | TTCAACATTT | CCGTGTCGCC | CTTATTCCCT | TTTTTGCGGC A TTTTGCCTT 4920 |
| CCTGTTTTTG | CTCACCCAGA | AACGCTGGTG | AAAGTAAAAG | ATGCTGAAGA T CAGTTGGGT 4980 |
| GCACGAGTGG | GTTACATCGA | ACTGGATCTC | AACAGCGGTA | AGATCCTTGA G AGTTTTCGC 5040 |
| CCCGAAGAAC | GTTTTCCAAT | GATGAGCACT | TTTAAAGTTC | TGCTATGTGG C GCGGTATTA 5100 |
| TCCCGTATTG | ACGCCGGGCA | AGAGCAACTC | GGTCGCCGCA | TACACTATTC T CAGAATGAC 5160 |
| TTGGTTGAGT | ACTCACCAGT | CACAGAAAAG | CATCTTACGG | ATGGCATGAC A GTAAGAGAA 5220 |
| TTATGCAGTG | CTGCCATAAC | CATGAGTGAT | AACACTGCGG | CCAACTTACT T CTGACAACG 5280 |
| ATCGGAGGAC | CGAAGGAGCT | AACCGCTTTT | TTGCACAACA | TGGGGGATCA T GTAACTCGC 5340 |
| CTTGATCGTT | GGGAACCGGA | GCTGAATGAA | GCCATACCAA | ACGACGAGCG T GACACCACG 5400 |
| ATGCCTGTAG | CAATGGCAAC | AACGTTGCGC | AAACTATTAA | CTGGCGAACT A CTTACTCTA 5460 |
| GCTTCCCGGC | AACAATTAAT | AGACTGGATG | GAGGCGGATA | AAGTTGCAGG A CCACTTCTG 5520 |
| CGCTCGGCCC | TTCCGGCTGG | CTGGTTTATT | GCTGATAAAT | CTGGAGCCGG T GAGCGTGGG 5580 |
| TCTCGCGGTA | TCATTGCAGC | ACTGGGGCCA | GATGGTAAGC | CCTCCCGTAT C GTAGTTATC 5640 |
| TACACGACGG | GGAGTCAGGC | AACTATGGAT | GAACGAAATA | GACAGATCGC T GAGATAGGT 5700 |
| GCCTCACTGA | TTAAGCATTG | GTAACTGTCA | GACCAAGTTT | ACTCATATAT A CTTTAGATT 5760 |
| GATTTAAAAC | TTCATTTTTA | ATTTAAAAGG | ATCTAGGTGA | AGATCCTTTT T GATAATCTC 5820 |
| ATGACCAAAA | TCCCTTAACG | TGAGTTTTCG | TTCCACTGAG | CGTCAGACCC C GTAGAAAAG 5880 |
| ATCAAAGGAT | CTTCTTGAGA | TCCTTTTTTT | CTGCGCGTAA | TCTGCTGCTT G CAAACAAAA 5940 |
| AAACCACCGC | TACCAGCGGT | GGTTTGTTTG | CCGGATCAAG | AGCTACCAAC T CTTTTTCCG 6000 |
| AAGGTAACTG | GCTTCAGCAG | AGCGCAGATA | CCAAATACTG | TCCTTCTAGT G TAGCCGTAG 6060 |
| TTAGGCCACC | ACTTCAAGAA | CTCTGTAGCA | CCGCCTACAT | ACCTCGCTCT G CTAATCCTG 6120 |
| TTACCAGTGG | CTGCTGCCAG | TGGCGATAAG | TCGTGTCTTA | CCGGGTTGGA C TCAAGACGA 6180 |
| TAGTTACCGG | ATAAGGCGCA | GCGGTCGGGC | TGAACGGGGG | GTTCGTGCAC A CAGCCCAGC 6240 |
| TTGGAGCGAA | CGACCTACAC | CGAACTGAGA | TACCTACAGC | GTGAGCATTG A GAAAGCGCC 6300 |
| ACGCTTCCCG | AAGGGAGAAA | GGCGGACAGG | TATCCGGTAA | GCGGCAGGGT C GGAACAGGA 6360 |
| GAGCGCACGA | GGGAGCTTCC | AGGGGGAAAC | GCCTGGTATC | TTTATAGTCC T GTCGGGTTT 6420 |
| CGCCACCTCT | GACTTGAGCG | TCGATTTTTG | TGATGCTCGT | CAGGGGGCG G AGCCTATGG 6480 |
| AAAAACGCCA | GCAACGCGGC | CTTTTTACGG | TTCCTGGCCT | TTTGCTGGCC T TTTGCTCAC 6540 |
| ATGTTCTTTC | CTGCGTTATC | CCCTGATTCT | GTGGATAACC | GTATTACCGC C TTTGAGTGA 6600 |
| GCTGATACCG | CTCGCCGCAG | CCGAACGACC | GAGCGCAGCG | AGTCAGTGAG C GAGGAAGCG 6660 |
| GAAGAGCGCC | CAATACGCAA | ACCGCCTCTC | CCCGCGCGTT | GGCCGATTCA T TAATGCAGC 6720 |

```
TGGCACGACA GGTTTCCCGA CTGGAAAGCG GGCAGTGAGC GCAACGCAAT T AATGTGAGT    6780

TAGCTCACTC ATTAGGCACC CCAGGCTTTA CACTTTATGC TTCCGGCTCG T ATGTTGTGT    6840

GGAATTGTGA GCGGATAACA ATTTCACACA GGAAACAGCT ATGACCATGA T TACGCCA     6898
```

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:28:

```
CAGATCTGCA GATCTGCATG GGCGATG                                         27
```

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:29:

```
GGGGACTCTA GAGGATCCCC GGGTGGTCAG TCCCTT                               36
```

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:30:

```
GAATTTCCCC                                                            10
```

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

```
GATCCGGATC CG                                                         12
```

(2) INFORMATION FOR SEQ ID NO:32:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TCGACGGATC CG                                                              12

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

GGGGACTCTA GAGGATCCCG AATTTCCCC                                            29

(2) INFORMATION FOR SEQ ID NO:34:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GATCCAGCTG AAGGCTCGAC AAGGCAGATC CACGGAGGAG CTGATATTTG G TGGACA            57

(2) INFORMATION FOR SEQ ID NO:35:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AGCTTGTCCA CCAAATATCA GCTCCTCCGT GGATCTGCCT TGTCCAGCCT T CAGCTG            57

(2) INFORMATION FOR SEQ ID NO:36:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

AGCTGTGGAT AGGAGCAACC CTATCCCTAA TATACCAGCA CCACCAAGTC A GGGCAATCC         60

CGGG                                                                      64

(2) INFORMATION FOR SEQ ID NO:37:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

TCGACCCGGG ATTGCCCTGA CTTGGTGGTG CTGGTATATT AGGGATAGGG T TGCTCCTAT         60

```
CCAC                                                                 64

(2) INFORMATION FOR SEQ ID NO:38:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CCGGGCCATT TGTTCCAGGC ACGGGATAAG CATTCAGCCA TGGGATATCA A GCTTGGATC   60

CC                                                                   62

(2) INFORMATION FOR SEQ ID NO:39:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

TCGAGGGATC CAAGCTTGAT ATCCCATGGC TGAATGCTTA TCCCGTGCCT G GAACAAATG   60

GC                                                                   62

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:40:

GATATCAAGC TTGGATCCC                                                 19

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

CGGTACCTCG AGTTAAC                                                   17

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:
```

```
CATGGTTAAC TCGAGGTACC GAGCT                                              25

(2) INFORMATION FOR SEQ ID NO:43:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:43:

ATCTGCATGG GTG                                                           13

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:44:

GGGGACTCTA GAGGATCCAG                                                    20

(2) INFORMATION FOR SEQ ID NO:45:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:45:

GTTAACTCGA GGTACCGAGC TCGAATTTCC CC                                      32

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:46:

GAGTTCAGGC TTTTTCATAG CT                                                 22

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:47:

AGATCTCGTG AGATAATGAA AAAG                                               24
```

(2) INFORMATION FOR SEQ ID NO:48:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

```
ACTCGCCGAT AGTGGAAACC GACGCCCCAG CACTCGTCCG AGGGCAAAGG A ATAGTAAGA      60

GCTCGG                                                                 66
```

(2) INFORMATION FOR SEQ ID NO:49:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

```
GATCCCGAGC TCTTACTATT CCTTTGCCCT CGGACGAGTG CTGGGCGTC G GTTTCCACT       60

ATCGGCGAGT                                                             70
```

(2) INFORMATION FOR SEQ ID NO:50:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:50:

```
CTGCAGGCCG GCCTTAATTA AGCGGCCGCG TTTAAACGCC CGGGCATTTA A ATGGCGCGC      60

CGCGATCGCT TGCAGATCTG CATGGGTG                                         88
```

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:51:

```
GACGGATCTG                                                             10
```

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:52:

```
TGAGATCTGA GCTCGAATTT CCCC                                             24
```

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:53:

```
GGTACCCCCG GGGTCGACCA TGG                                         23
```

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:54:

```
GGGAATTGGA GCTCGAATTT CCCC                                        24
```

(2) INFORMATION FOR SEQ ID NO:55:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:55:

```
GGGAAATTAA GCTT                                                   14
```

(2) INFORMATION FOR SEQ ID NO:56:

(i) SEQUENCE CHARACTERISTICS:
        (A) LENGTH: 69 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:56:

```
AGCGGCCGCA TTCCCGGGAA GCTTGCATGC CTGCAGAGAT CCGGTACCCG G GGATCCTCT    60
AGAGTCGAC                                                            69
```

(2) INFORMATION FOR SEQ ID NO:57:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:57:

```
GGTACCCCCG GGGTCGACCA TGGTTAACTC GAGGTACCGA GCTCGAATTT C CCC          54
```

-continued (2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:58:

GGGAATTGGT TTAAACGCGG CCGCTT        26

(2) INFORMATION FOR SEQ ID NO:59:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:59:

CCATGCATGG        10

US 6,384,207 B1

REGULATORY SEQUENCES FOR TRANSGENIC PLANTS

RELATED APPLICATIONS

This application claims the priority of U.S. patent application Ser. No. 60/049,752, filed Jun. 12, 1997.

FIELD OF THE INVENTION

This invention relates to genetic engineering of plants. More particularly, the invention provides DNA sequences and constructs that are useful to control expression of recombinant genes in plants. Specific constructs of the invention use novel regulatory sequences derived from a maize root preferential cationic peroxidase gene.

BACKGROUND OF THE INVENTION

Through the use of recombinant DNA technology and genetic engineering, it has become possible to introduce desired DNA sequences into plant cells to allow for the expression of proteins of interest. However, obtaining desired levels of expression remains a challenge. To express agronomically important genes in crops at desired levels through genetic engineering requires the ability to control the regulatory mechanisms governing expression in plants, and this requires access to suitable regulatory sequences that can be coupled with the genes it is desired to express.

A given project may require use of several different expression elements, for example one set to drive a selectable marker or reporter gene and another to drive the gene of interest. The selectable marker may not require the same expression level or pattern as that required for the gene of interest. Depending upon the particular project, there may be a need for constitutive expression, which directs transcription in most or all tissues at all times, or there may be a need for tissue specific expression. For example, a root specific or root preferential expression in maize would be highly desirable for use in expressing a protein toxic to pests that attack the roots of maize.

Cells use a number of regulatory mechanisms to control which genes are expressed and the level at which they are expressed. Regulation can be transcriptional or post-transcriptional and can include, for example, mechanisms to enhance, limit, or prevent transcription of the DNA, as well as mechanisms that limit the life span of the mRNA after it is produced. The DNA sequences involved in these regulatory processes can be located upstream, downstream or even internally to the structural DNA sequences encoding the protein product of a gene.

Initiation of transcription of a gene is regulated by a sequence, called the promoter, located upstream (5') of the coding sequence. Eukaryotic promoters generally contain a sequence with homology to the consensus 5'-TATAAT-3' (TATA box) about 10–35 base pairs (bp) upstream of the transcription start (CAP) site. Most maize genes have a TATA box 29 to 34 base pairs upstream of the CAP site. In most instances the TATA box is required for accurate transcription initiation. Further upstream, often between –80 and –100, there can be a promoter element with homology to the consensus sequence CCAAT. This sequence is not well conserved in many species including maize. However, genes which have this sequence appear to be efficiently expressed. In plants the CCAAT "box" is sometimes replaced by the AGGA "box". Other sequences conferring tissue specificity, response to environmental signals or maximum efficiency of transcription may be found interspersed with these promoter elements or found further in the 5' direction from the CAP site. Such sequences are often found within 400 bp of the CAP site, but may extend as far as 1000 bp or more.

Promoters can be classified into two general categories. "Constitutive" promoters are expressed in most tissues most of the time. Expression from a constitutive promoter is more or less at a steady state level throughout development. Genes encoding proteins with housekeeping functions are often driven by constitutive promoters. Examples of constitutively expressed genes in maize include actin and ubiquitin. Wilmink et al. (1995). "Regulated" promoters are typically expressed in only certain tissue types (tissue specific promoters) or at certain times during development (temporal promoters). Examples of tissue specific genes in maize include the zeins (Kriz et al., (1987)) which are abundant storage proteins found only in the endosperm of seed. Many genes in maize are regulated by promoters that are both tissue specific and temporal.

It has been demonstrated that promoters can be used to control expression of foreign genes in transgenic plants in a manner similar to the expression pattern of the gene from which the promoter was originally derived. The most thoroughly characterized promoter tested with recombinant genes in plants has been the 35S promoter from the Cauliflower Mosaic Virus (CaMV) and its derivatives. U.S. Pat. No. 5,352,065; Wilmink et al. (1995); Datla et al. (1993). Elegant studies conducted by Benfey et al. (1984) reveal that the CaMV 35S promoter is modular in nature with regards to binding to transcription activators. U.S. Pat. No. 5,097,025; Benfey et al. (1989) and (1990). Two independent domains result in the transcriptional activation that has been described by many as constitutive. The 35S promoter is very efficiently expressed in most dicots and is moderately expressed in monocots. The addition of enhancer elements to this promoter has increased expression levels in maize and other monocots. Constitutive promoters of monocot origin (that are not as well studied) include the polyubiquitin-1 promoter and the rice actin-1 promoter. Wilmink et al. (1995). In addition, a recombinant promoter, Emu, has been constructed and shown to drive expression in monocots in a constitutive manner, Wilmink et al. (1995).

Few tissue specific promoters have been characterized in maize. The promoters from the zein gene and oleosin gene have been found to regulate GUS in a tissue specific manner. Kriz et al. (1987); Lee and Huang (1994). No root specific promoters from maize have been described in the literature. However, promoters of this type have been characterized in other plant species.

Despite both the important role of tissue specific promoters in plant development, and the opportunity that availability of a root preferential promoter would represent for plant biotechnology, relatively little work has yet been done on the regulation of gene expression in roots. Yamamoto reported the expression of *E. coli*: uidA gene, encoding β-glucuronidase (GUS), under control of the promoter of a tobacco (*N. tabacum*) root-specific gene, TobRB7. Yamamoto et al. (1991), Conkling et al. (1990). Root specific expression of the fusion genes was analyzed in transgenic tobacco. Significant expression was found in the root-tip meristem and vascular bundle. EPO Application Number 452 269 (De Framond) teaches that promoters from metallathionein-like genes are able to function as promoters of tissue-preferential transcription of associated DNA sequences in plants, particularly in the roots. Specifically, a promoter from a metallathionein-like gene was operably linked to a GUS reporter gene and tobacco leaf disks were transformed. The promoter was shown to express in roots, leaves and stems. WO 9113992 (Croy, et al.) teaches that rape (*Brassica napus* L.) extensin gene promoters are capable of directing tissue-preferential transcription of associated DNA sequences in plants, particularly in the roots. Specifically, a rape extensin gene promoter was operably linked to a extA (extensin structural gene) and tobacco leaf disks were transformed. It was reported that northern analysis revealed no hybridization of an extensin probe to leaf RNA from either control or transformed tobacco plants and hybridization of the extensin probe to transgenic root RNA of all transformants tested, although the levels of hybridization varied for the transformants tested. While each of these promoters has shown some level of tissue-preferential gene expression in a dicot model system (tobacco), the specificity of these promoters, and expression patterns and levels resulting from activity of the promoters, has yet to be achieved in monocots, particularly maize.

DNA sequences called enhancer sequences have been identified which have been shown to enhance gene expression when placed proximal to the promoter. Such sequences have been identified from viral, bacterial, and plant gene sources. An example of a well characterized enhancer sequence is the ocs sequence from the octopine synthase gene in *Agrobacterium tumefaciens*. This short (40 bp) sequence has been shown to increase gene expression in both dicots and monocots, including maize, by significant levels. Tandem repeats of this enhancer have been shown to increase expression of the GUS gene eight-fold in maize. It remains unclear how these enhancer sequences function. Presumably enhancers bind activator proteins and thereby facilitate the binding of RNA polymerase II to the TATA box. Grunstein (1992). WO95/14098 describes testing of various multiple combinations of the ocs enhancer and the mas (mannopine synthase) enhancer which resulted in several hundred fold increase in gene expression of the GUS gene in transgenic tobacco callus.

The 5' untranslated leader sequence of mRNA, introns, and the 3' untranslated region of mRNA affect expression by their effect on post-transcription events, for example by facilitating translation or stabilizing mRNA.

Expression of heterologous plant genes has also been improved by optimization of the non-translated leader sequence, i.e. the 5' end of the mRNA extending from the 5' CAP site to the AUG translation initiation codon of the mRNA. The leader plays a critical role in translation initiation and in regulation of gene expression. For most eukaryotic mRNAs, translation initiates with the binding of the CAP binding protein to the mRNA CAP. This is then followed by the binding of several other translation factors, as well as the 43S ribosome pre-initiation complex. This complex travels down the mRNA molecule while scanning for an AUG initiation codon in an appropriate sequence context. Once this has been found, and with the addition of the 60S ribosomal subunit, the complete 80S initiation complex initiates protein translation. Pain (1986); Kozak (1986). Optimization of the leader sequence for binding to the ribosome complex has been shown to increase gene expression as a direct result of improved translation initiation efficiency. Significant increases in gene expression have been produced by addition of leader sequences from plant viruses or heat shock genes. Raju et al. (1993); Austin (1994) reported that the length of the 5' non-translated leader was important for gene expression in protoplasts.

In addition to the untranslated leader sequence, the region directly around the AUG start appears to play an important role in translation initiation. Luerhsen and Walbot (1994). Optimization of the 9 bases around the AUG start site to a Kozak consensus sequence was reported to improve transient gene expression 10-fold in BMS protoplasts. McElroy et al. (1994).

Studies characterizing the role of introns in the regulation of gene expression have shown that the first intron of the maize alcohol dehydrogenase gene (Adh-1) has the ability to increase expression under anaerobiosis. Callis et al. (1987). The intron also stimulates expression (to a lesser degree) in the absence of anaerobiosis. This enhancement is thought to be a result of a stabilization of the pre-mRNA in the nucleus. Mascarenhas et al. reported a 12-fold and 20-fold enhancement of CAT expression by use of the Adh-1 intron. Mascarenhas et al. (1990). Several other introns have been identified from maize and other monocots which increase gene expression. Vain et al. (1996).

The 3' end of the mRNA can also have a large effect on expression, and is believed to interact with the 5' CAP. Sullivan (1993). The 3' untranslated region (3'UTR) has been shown to have a significant role in gene expression of several maize genes. Specifically, a 200 base pair 3' sequence has been shown to be responsible for suppression of light induction of the maize small m3 subunit of the ribulose-1,5-biphosphate carboxylase gene (rbc/m3) in mesophyll cells. Viret et al. (1994). Some 3' UTRs have been shown to contain elements that appear to be involved in instability of the transcript. Sullivan et al. (1993). The 3'UTRs of most eukaryotic genes contain consensus sequences for polyadenylation. In plants, especially maize, this sequence is not very well conserved. The 3' untranslated region, including a polyadenylation signal, derived from a nopaline synthase gene (3' nos) is frequently used in plant genetic engineering. Few examples of heterologous 3'UTR testing in maize have been published.

Important aspects of the present invention are based on the discovery that DNA sequences derived from a maize root specific cationic peroxidase gene are exceptionally useful for use in regulating expression of recombinant genes in plants.

The peroxidases (donor:hydrogen-peroxide oxidoreductase, EC 1.11.1.7) are highly catalytic enzymes with many potential substrates in the plant. See Gaspar, et al. (1982). They have been implicated in such diverse functions as secondary cell wall biosynthesis, wound-healing, auxin catabolism, and defense of plants against pathogen attack. See Lagrimini and Rothstein (1987); Morgens et al. (1990); Nakamura et al. (1988); Fujiyama et al. (1988); and Mazza et al. (1980).

Most higher plants possess a number of different peroxidase isozymes whose pattern of expression is tissue specific, developmentally regulated, and influenced by environmental factors. Lagrimini & Rothstein (1987). Based upon their isoelectric point, plant peroxidases are subdivided into three subgroups: anionic, moderately anionic, and cationic.

The function of anionic peroxidase isozymes (pI, 3.5–4.0) is best understood. Isozymes from this group are usually cell wall associated. They display a high activity for polymerization of cinnamyl alcohols in vitro and have been shown to function in lignification and cross-linking of extensin monomers and feruloylated polysaccharides. Lagrimini and Rothstein (1987). In both potato and tomato, expression of anionic peroxidases have been shown to be induced upon both wound induction and abscisic acid treatment. Buffard et al. (1990). This suggests their involvement in both wound healing and in the regulation of tissue suberization.

Moderately anionic peroxidase isozymes (pI, 4.5–6.5) are also cell wall associated and have some activity toward lignin precursors. In tobacco, isozymes of this class have been shown to be highly expressed in wounded stem tissue Fujiyama et al. (1988). These isozymes may also serve a function in suberization and wound healing. Morgens et al. (1990).

The actual function of cationic peroxidase isozymes (pI, 8.1–11) in the plant remains unclear. Some members of this group, however, have been shown to efficiently catalyze the synthesis of $H_2O_2$ from NADH and $H_2O$. Others are localized to the central vacuole. In the absence of $H_2O_2$, some of these isozymes possess indoleacetic acid oxidase activity. Lagrimini and Rothstein (1987).

Electrophoretic studies of maize peroxidases have revealed 13 major isozymes. Brewbaker et al. (1985). All isozymes were judged to be functional as monomers, despite major differences in molecular weight. All maize tissues had more than one active peroxidase locus, and all loci were tissue-specific. The peroxidases have proved unique in that no maize tissue has been found without activity, and no peroxidase has proven expressed in all maize tissues.

SUMMARY OF THE INVENTION

The invention provides isolated DNA molecules derived from the per5 maize root preferential cationic peroxidase gene that can be used in recombinant constructs to control expression of genes in plants. More particularly, the invention provides isolated DNA molecules derived from the per5 promoter sequence and having as at least a part of its sequence bp 4086–4148 of SEQ ID NO 1. Preferred embodiments are isolated DNA molecules that have as part of their sequences bp 4086 to 4200, bp 4086 to 4215, bp 3187 to 4148, bp 3187 to 4200, bp 3187 to 4215, bp 2532–4148, bp 2532 to 4200, bp 2532 to 4215, bp 1–4148, bp, bp 1–4200, or bp 1–4215 of SEQ ID NO 1.

The invention also provides isolated DNA molecules selected from the following per5 intron sequences: bp 4426–5058, bp 4420–5064, bp 5251–5382, bp 5245–5388, bp 5549–5649, and bp 5542–5654 of SEQ ID NO 1.

The invention also provides isolated DNA molecules derived from the per5 transcription termination sequence and having the sequence of bp 6068–6431 of SEQ ID NO 1.

In another of its aspects, the present invention provides a recombinant gene cassette competent for effecting preferential expression of a gene of interest in a selected tissue of transformed maize, said gene cassette comprising:
  a) a promoter from a first maize gene, said first maize gene being one that is naturally expressed preferentially in the selected tissue;
  b) an untranslated leader sequence;
  c) the gene of interest, said gene being one other than said first maize gene;
  d) a 3'UTR; said promoter, untranslated sequence, gene of interest, and 3'UTR being operably linked from 5' to 3'; and
  e) an intron sequence that is incorporated in said untranslated leader sequence or in said gene of interest, said intron sequence being from an intron of a maize gene that is preferentially expressed in said selected tissue.

A related embodiment of the invention is a recombinant gene cassette competent for effecting constitutive expression of a gene of interest in transformed maize comprising:
  a) a promoter from a first maize gene, said first maize gene being one that is naturally expressed preferentially in a specific tissue;
  b) an untranslated leader sequence;
  c) the gene of interest, said gene being one other than said first maize gene;
  d) a 3'UTR; said promoter, untranslated sequence, gene of interest, and 3'UTR being operably linked from 5' to 3'; and
  e) an intron sequence that is incorporated in said untranslated leader or in said gene of interest, said intron sequence being from an intron of a maize gene that is naturally expressed constitutively.

In a particular embodiment the intron is one from the maize Adh1 expressed gene, and the resulting recombinant gene cassette provides constitutive expression in maize.

In another of its aspects, the invention provides DNA constructs comprising, operatively linked in the 5' to 3' direction,
  a) a promoter having as at least part of its sequence bp 4086–4148 bp of SEQ ID NO 1;
  b) an untranslated leader sequence comprising bp 4149–4200 of SEQ ID NO 1,
  c) a gene of interest not naturally associated with said promoter, and
  d) a 3'UTR.

Preferred embodiments of this aspect of the invention are those wherein the promoter comprises bp 3187 to 4148, bp 2532–4148, or bp 1–4148 of SEQ ID NO 1. Particularly preferred are each of the preferred embodiments wherein said 3'UTR has the sequence of bp 6066–6340 or bp 6066–6439 of SEQ ID NO 1.

In another of its aspects, the invention provides DNA constructs comprising, operatively linked in the 5' to 3' direction,
  a) a promoter having as at least part of its sequence bp 4086–4148 bp of SEQ ID NO 1;
  b) an untranslated leader sequence not naturally associated with said promoter,
  c) a gene of interest,
  d) a 3'UTR.

Preferred embodiments of this aspect of the invention are those wherein the promoter comprises bp 3187 to 4148, bp 2532–4148, or bp 1–4148 of SEQ ID NO 1. Particularly preferred are each of the preferred embodiments wherein said 3'UTR has the sequence of bp 6066–6340 or bp 6066–6439 of SEQ ID NO 1.

In another of its aspects, the invention provides a DNA construct comprising, operatively linked in the 5' to 3' direction,
  a) a promoter having as at least a part of its sequence bp 4086–4148 bp of SEQ ID NO 1;
  b) an untranslated leader sequence comprising bp 4149–4200 of SEQ ID NO 1;
  c) an intron selected from the group consisting of an Adh1 gene intron and bp 4426–5058 of SEQ ID NO 1;
  d) a gene of interest; and
  e) a 3'UTR.

Preferred embodiments of this aspect of the invention are again those wherein the promoter comprises bp 3187 to 4148, bp 2532–4148, or bp 1–4148 of SEQ ID NO 1. Particularly preferred are each of the preferred embodiments wherein said 3'UTR has the sequence of bp 6066–6340 or bp 6066–6439 of SEQ ID NO 1.

In another of its aspects, the invention provides a DNA construct comprising, in the 5' to 3' direction,
  a) a promoter having as at least part of its sequence bp 4086–4148 bp of SEQ ID NO 1;

b) an untranslated leader sequence;

c) an intron selected from the group consisting of an Adh1 gene intron and bp 4426–5058 of SEQ ID NO 1;

d) a cloning site;

e) a 3'UTR.

In accordance with another significant aspect of the invention, there is provided a recombinant gene cassette comprised of the following operably linked sequences, from 5' to 3': a promoter; an untranslated leader sequence; a gene of interest; and the per5 3'UTR, bp 6068–6431 of SEQ ID NO 1.

In another of its aspects, the invention provides a plasmid comprising a promoter having as at least part of its sequence bp 4086–4148 of SEQ ID NO 1.

In another of its aspects, the invention provides a transformed plant comprising at least one plant cell that contains a DNA construct of the invention. The plant may be a monocot or dicot. Preferred plants are maize, rice, cotton and tobacco.

In another of its aspects, the invention provides seed or grain that contains a DNA construct of the invention.

DETAILED DESCRIPTION OF THE INVENTION

In one of its aspects, the present invention relates to regulatory sequences derived from the maize root preferential cationic peroxidase protein (per5) that are able to regulate expression of associated DNA sequences in plants. More specifically, the invention provides novel promoter sequences and constructs using them. It also provides novel DNA constructs utilizing the per5 untranslated leader and/or 3'UTR. It also provides novel DNA constructs utilizing the introns from the per5 gene.

The DNA sequence for a 6550 bp fragment of the genomic clone of the maize root-preferential cationic peroxidase gene is given in SEQ ID NO 1. The sequence includes a 5' flanking region (nt 1–4200), of which nucleotides 4149–4200 correspond to the untranslated leader sequence. The coding sequence for the maize root-preferential cationic peroxidase is composed of four exons: exon 1 (nt 4201–4425), exon 2 (nt 5059–5250), exon 3 (nt 5383–5547), and exon 4 (nt 5649–6065). It should be noted that the first 96 nucleotides of exon 1 (nt 4201–4296) code for a 32 amino acid signal peptide, which is excised from the polypeptide after translation to provide the mature protein. Three introns were found: intron 1 (nt 4426–5058), intron 2 (5251–5382), and intron 3 (5548–5648). The 3' flanking region (373 nucleotides in length) extends from nucleotide 6069 (after the UGA codon at nucleotides 6066–6068) to nucleotide 6550, including a polyadenylation signal at nucleotides 6307–6312.

We have discovered that promoters derived from certain tissue preferential maize genes require the presence of an intron in the transcribed portion of the gene in order for them to provide effective expression in maize and that the temporal and tissue specificity observed depends on the intron used. A recombinant gene cassette having a tissue preferential maize promoter, but lacking an intron in the transcribed portion of the gene, does not give appropriate expression in transformed maize. If the transcribed portion of the cassette includes an intron derived from a maize gene of similar tissue specificity to the maize gene from which the promoter was obtained, the gene cassette will restore tissue preferential expression in maize. The intron may be, but need not necessarily be, from the same gene as the promoter. If an intron derived from another maize gene, such as Adh1 intron 1, is used in a gene cassette with a promoter from a tissue preferential maize gene, the cassette will give generally constitutive expression in maize. We have also found that these considerations apply to transgenic maize, but not to transgenic rice. Tissue preferential maize promoters can be used to drive recombinant genes in rice without an intron.

In accordance with the foregoing unexpected and significant fundings, the present invention provides a recombinant gene cassette competent for effecting preferential expression of a gene of interest in a selected tissue of transformed maize, said gene cassette comprising:

a) a promoter from a first maize gene, said first maize gene being one that is naturally expressed preferentially in the selected tissue;

b) an untranslated leader sequence;

c) the gene of interest, said gene being one other than said first maize gene;

d) a 3'UTR;

said promoter, untranslated sequence, gene of interest, and 3'UTR being operably linked from 5' to 3'; and e) an intron sequence that is incorporated in said untranslated leader sequence or in said gene of interest, said intron sequence being from an intron of a maize gene that is preferentially expressed in said selected tissue.

The promoter used in this embodiment can be from any maize gene that is preferentially expressed in the tissue of interest. Such maize genes can be identified by conventional methods, for example, by techniques involving differential screening of mRNA sequences.

A detailed example of identification and isolation of a tissue preferential maize gene is given herein for the root preferential maize cationic peroxidase gene. The method illustrated in this example can be used to isolate additional genes from various maize tissues.

Examples of tissue preferential maize genes that have promoters suitable for use in the invention include: O-methyl transferase and glutamine synthetase 1.

A preferred promoter is the per5 promoter, i.e. the promoter from the root preferential maize cationic peroxidase gene. Particularly preferred is the promoter comprising bp 1 to 4215 of SEQ ID NO 1.

The non-translated leader sequence can be derived from any suitable source and may be specifically modified to increase the translation of the mRNA. The 5' non-translated region may be obtained from the promoter selected to express the gene, the native leader sequence of the gene or coding region to be expressed, viral RNAs, suitable eukaryotic genes, or may be a synthetic sequence.

The gene of interest may be any gene that it is desired to express in plants. Particularly useful genes are those that confer tolerance to herbicides, insects, or viruses, and genes that provide improved nutritional value or processing characteristics of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. Other suitable genes are identified hereinafter. As is readily understood by those skilled in the art, any agronomically important gene conferring a desired trait can be used.

The 3'UTR, or 3' untranslated region, that is employed is one that confers efficient processing of the mRNA, maintains stability of the message and directs the addition of adenosine ribonucleotides to the 3' end of the transcribed mRNA sequence. The 3'UTR may be native with the promoter region, native with the structural gene, or may be derived from another source. Suitable 3'UTRs include but are, not limited to: the per5 3'UTR, and the 3'UTR of the nopaline synthase (nos) gene.

The intron used will depend on the particular tissue in which it is desired to preferentially express the gene of interest. For tissue preferential expression in maize, the intron should be selected from a maize gene that is naturally expressed preferentially in the selected tissue.

The intron must be incorporated into a transcribed region of the cassette. It is preferably incorporated into the untranslated leader 5' of the gene of interest and 3' of the promoter or within the translated region of the gene.

Why certain tissue preferential maize genes require an intron to enable effective expression in maize tissues is not known, but experiments indicate that the critical event is post-transcriptional processing. Accordingly, the present invention requires that the intron be provided in a transcribed portion of the gene cassette.

A related embodiment of the invention is a recombinant gene cassette competent for effecting constitutive expression of a gene of interest in transformed maize comprising:

a) a promoter from a first maize gene, said first maize gene being one that is naturally expressed preferentially in a specific tissue;

b) an untranslated leader sequence;

c) the gene of interest, said gene being one other than said first maize gene;

d) a 3'UTR;

said promoter, untranslated sequence, gene of interest, and 3'UTR being operably linked from 5' to 3'; and e) an intron sequence that is incorporated in said untranslated leader or in said gene of interest, said intron sequence being from an intron of a maize gene that is naturally expressed constitutively.

This embodiment differs from the previous embodiment in that the intron is one from a gene expressed in most tissues, and the expression obtained from the resulting recombinant gene cassette in maize is constitutive. Suitable introns for use in this embodiment of the invention include Adh1 intron 1, Ubiquitin intron 1, and Bronze 2 intron 1. Particularly preferred is the Adh1 intron 1. Although it has previously been reported that the Adh1 intron 1 is able to enhance expression of constitutively expressed genes, it has never been reported or suggested that the Adh1 intron can alter the tissue preferential characteristics of a tissue preferential maize promoter.

The present invention is generally applicable to the expression of structural genes in both monocotyledonous and dicotyledonous plants. This invention is particularly suitable for any member of the monocotyledonous (monocot) plant family including, but not limited to, maize, rice, barley, oats, wheat, sorghum, rye, sugarcane, pineapple, yams, onion, banana, coconut, and dates. A preferred application of the invention is in production of transgenic maize plants.

This invention, utilizing a promoter constructed for monocots, is particularly applicable to the family Graminaceae, in particular to maize, wheat, rice, oat, barley and sorghum.

In accordance with another aspect of the invention, there is provided a recombinant gene cassette comprised of: a promoter; an untranslated leader sequence; a gene of interest; and the per5 3'UTR. Use of the per5 3'UTR provides enhanced expression compared to similar gene cassettes utilizing the nos 3'UTR.

The promoter used with the per5 3'UTR can be any promoter suitable for use in plants. Suitable promoters can be obtained from a variety of sources, such as plants or plant DNA viruses. Preferred promoters are the per5 promoter, the 35T promoter (described hereinafter in Examples 20 and 23), and the ubiquitin promoter. Useful promoters include those isolated from the caulimovirus group, such as the cauliflower mosaic virus 19S and 35S (CaMV19S and CaMV35S) transcript promoters. Other useful promoters include the enhanced CaMV35S promoter (eCaMV35S) as described by Kat et al. (1987) and the small subunit promoter of ribulose 1,5-bisphosphate carboxylase oxygenase (RUBISCO). Examples of other suitable promoters are rice actin gene promoter; cyclophilin promoter; Adh1 gene promoter, Callis et al. (1987); Class I patatin promoter, Bevan et al. (1986); ADP glucose pyrophosphorylase promoter; beta.-conglycinin promoter, Tierney et al. (1987); E8 promoter, Deikman et al. (1988); 2AII promoter, Pear et al. (1989); acid chitinase promoter, Samac et al. (1990). The promoter selected should be capable of causing sufficient expression of the desired protein alone, but especially when used with the per5 3'UTR, to result in the production of an effective amount of the desired protein to cause the plant cells and plants regenerated therefrom to exhibit the properties which are phenotypically caused by the expressed protein.

The untranslated leader used with the per5 3'UTR is not critical. The untranslated leader will typically be one that is naturally associated with the promoter. The untranslated leader may be one that has been modified in accordance with another aspect of the present invention to include an intron. It may also be a heterologous sequence, such as one provided by U.S. Pat. No. 5,362,865. This non-translated leader sequence can be derived from any suitable source and can be specifically modified to increase translation of the mRNA.

The gene of interest may be any gene that it is desired to express in plants, as described above.

The terms "per5 3'UTR" and/or "per5 transcription termination region" are intended to refer to a sequence comprising bp 6068 to 6431 of SEQ ID NO 1.

Construction of gene cassettes utilizing the per5 3'UTR is readily accomplished utilizing well known methods, such as those disclosed in Sambrook et al. (1989); and Ausubel et al. (1987).

As used in the present application, the terms "root-preferential promoter", "root-preferential expression", "tissue-preferential expression" and "preferential expression" are used to indicate that a given DNA sequence derived from the 5' flanking or upstream region of a plant gene of which the structural gene is expressed in the root tissue exclusively, or almost exclusively and not in the majority of other plant parts. This DNA sequence when connected to an open reading frame of a gene for a protein of known or unknown function causes some differential effect; i.e., that the transcription of the associated DNA sequences or the expression of a gene product is greater in some tissue, for example, the roots of a plant, than in some or all other tissues of the plant, for example, the seed. Expression of the product of the associated gene is indicated by any conventional RNA, cDNA, protein assay or biological assay, or that a given DNA sequence will demonstrate.

This invention involves the construction of a recombinant DNA construct combining DNA sequences from the promoter of a maize root-preferential cationic peroxidase gene, a plant expressible structural gene (e.g. the GUS gene (Jefferson, (1987)) and a suitable terminator.

The present invention also includes DNA sequences having substantial sequence homology with the specifically disclosed regulatory sequences, such that they are able to have the disclosed effect on expression.

As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. For example, a sequence which has substantial sequence homology with a DNA sequence disclosed to be a root-preferential promoter will be able to direct the root-preferential expression of an associated DNA sequence. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art.

DNA encoding the maize root-preferential cationic peroxidase promoter may be prepared from chromosomal DNA or DNA of synthetic origin by using well-known techniques. Specifically comprehended as part of this invention are genomic DNA sequences. Genomic DNA may be isolated by standard techniques. Sambrook et al. (1989); Mullis et al. (1987); Horton et al. (1989); Erlich (ed.)(1989). It is also possible to prepare synthetic sequences by oligonucleotide synthesis. See Caruthers (1983) and Beaucage et al. (1981).

It is contemplated that sequences corresponding to the above noted sequences may contain one or more modifications in the sequences from the wild-type but will still render the respective elements comparable with respect to the teachings of this invention. For example, as noted above, fragments may be used. One may incorporate modifications into the isolated sequences including the addition, deletion, or nonconservative substitution of a limited number of various nucleotides or the conservative substitution of many nucleotides. Further, the construction of such DNA molecules can employ sources which have been shown to confer enhancement of expression of heterologous genes placed under their regulatory control. Exemplary techniques for modifying oligonucleotide sequences include using polynucleotide-mediated, site-directed mutagenesis. See Zoller et al. (1984); Higuchi et al. (1988); Ho et al. (1989); Horton et al. (1989); and *PCR Technology: Principles and Applications for DNA Amplification*, (ed.) Erlich (1989).

In one embodiment, an expression cassette of this invention, will comprise, in the 5' to 3' direction, the maize root-preferential cationic peroxidase promoter sequence, in reading frame, one or more nucleic acid sequences of interest followed by a transcript termination sequence. The expression cassette may be used in a variety of ways, including for example, insertion into a plant cell for the expression of the nucleic acid sequence of interest.

The tissue-preferential promoter DNA sequences are preferably linked operably to a coding DNA sequence, for example, a DNA sequence which is transcribed into RNA, or which is ultimately expressed in the production of a protein product.

A promoter DNA sequence is said to be "operably linked" to a coding DNA sequence if the two are situated such that the promoter DNA sequence influences the transcription of the coding DNA sequence. For example, if the coding DNA sequence codes for the production of a protein, the promoter DNA sequence would be operably linked to the coding DNA sequence if the promoter DNA sequence affects the expression of the protein product from the coding DNA sequence. For example, in a DNA sequence comprising a promoter DNA sequence physically attached to a coding DNA sequence in the same chimeric construct, the two sequences are likely to be operably linked.

The DNA sequence associated with the regulatory or promoter DNA sequence may be heterologous or homologous, that is, the inserted genes may be from a plant of a different species than the recipient plant. In either case, the DNA sequences, vectors and plants of the present invention are useful for directing transcription of the associated DNA sequence so that the mRNA transcribed or the protein encoded by the associated DNA sequence is expressed in greater abundance in some plant tissue, such as the root, leaves or stem, than in the seed. Thus, the associated DNA sequence preferably may code for a protein that is desired to be expressed in a plant only in preferred tissue, such as the roots, leaves or stems, and not in the seed.

Promoters are positioned 5' (upstream) to the genes that they control. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated herein with multiple copies of regulatory elements, some variation in this distance can occur.

Any plant-expressible structural gene can be used in these constructions. A structural gene is that portion of a gene comprising a DNA segment encoding a protein, polypeptide, antisense RNA or ribozyme or a portion thereof. The term can refer to copies of a structural gene naturally found within the cell, but artificially introduced, or the structural gene may encode a protein not normally found in the plant cell into which the gene is introduced, in which case it is termed a heterologous gene.

The associated DNA sequence may code, for example, for proteins known to inhibit insects or plant pathogens such as fungi, bacteria and nematodes. These proteins include, but are not limited to, plant non-specific lipid acyl hydrolases, especially patatin; midgut-effective plant cystatins, especially potato papain inhibitor; magainins, Zasloff (1987); cecropins, Hultmark et al. (1982); attacins, Hultmark et al. (1983); melittin; gramicidin S, Katsu et al. (1988); sodium channel proteins and synthetic fragments, Oiki et al. (1988): the alpha toxin of *Staphylococcus aureus*, Tobkes et al. (1985); apolipoproteins and fragments thereof, Knott et al. (1985) and Nakagawa et al. (1985); alamethicin and a variety of synthetic amphipathic peptides, Kaiser et al. (1987); lectins, Lis et al. (1986) and Van Parijs et al. (1991); pathogenesis-related proteins, Linthorst (1991); osmotins and permatins, Vigers et al. (1992) and Woloscuk et al. (1991); chitinases; glucanases, Lewah et al. (1991); thionins, Bohlmann and Apel (1991); protease inhibitors, Ryan (1990); plant anti-microbial peptides, Cammue et al. (1992); and polypeptides from *Bacillus thuringiensis*, which are postulated to generate small pores in the insect gut cell membrane, Knowles et al. (1987) and Hofte and Whitely (1989).

The structural gene sequence will generally be one which originates from a plant of a species different from that of the target organism. However, the present invention also contemplates the root preferential expression of structural genes which originates from a plant of the same species as that of the target plant but which are not natively expressed under control of the native root preferential cationic peroxidase (per5) promoter.

The structural gene may be derived in whole or in part from a bacterial genome or episome, eukaryotic genomic, mitochondrial or plastid DNA, cDNA, viral DNA, or chemically synthesized DNA. It is possible that a structural gene may contain one or more modifications in either the coding or the untranslated regions which could affect the biological activity or the chemical structure of the expression product, the rate of expression, or the manner of expression control. Such modifications include, but are not limited to, mutations, insertions, deletions, rearrangements and substitutions of one or more nucleotides. The structural gene may constitute an uninterrupted coding sequence or it may include one or more introns, bounded by the appropriate plant-functional splice junctions. The structural gene may be a composite of segments derived from a plurality of sources, naturally occurring or synthetic. The structural gene may also encode a fusion protein, so long as the experimental manipulations maintain functionality in the joining of the coding sequences.

The use of a signal sequence to secrete or sequester in a selected organelle allows the protein to be in a metabolically inert location until released in the gut environment of an insect pathogen. Moreover, some proteins are accumulated to higher levels in transgenic plants when they are secreted from the cells, rather than stored in the cytosol. Hiatt, et al. (1989).

At the 3' terminus of the structural gene will be provided a termination sequence which is functional in plants. A wide variety of termination regions are available that may be obtained from genes capable of expression in plant hosts, e.g., bacterial, opine, viral, and plant genes. Suitable 3'UTRs include those that are known to those skilled in the art, such as the nos 3', tmL 3', or acp 3', for example.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include, in addition to the maize root-preferential cationic peroxidase promoter sequence (including a transcriptional start site), a leader sequence and a DNA sequence coding for translation start-signal codon (generally obtained from either the maize root-preferential cationic peroxidase gene or from the gene of interest to be expressed by the promoter or from a leader from a third gene which is known to work well or enhance expression in the selected host cell), a translation terminator codon, and a DNA sequence coding for a 3' non-translated region containing signals controlling messenger RNA processing. Selection of appropriate elements to optimize expression in any particular species is a matter of ordinary skill in the art utilizing the teachings of this disclosure; in some cases hybrid constructions are preferred, combining promoter elements upstream of the tissue preferential promoter TATA and CAAT box to a minimal 35S derived promoter consisting of the 35S TATA and CAAT box. Finally, the vectors should desirably have a marker gene that is capable of providing a phenotypical property which allows for identification of host cells containing the vector, and an intron in the 5' untranslated region, e.g., intron 1 from the maize alcohol dehydrogenase gene that enhances the steady state levels of mRNA of the marker gene.

The activity of the foreign gene inserted into plant cells is dependent upon the influence of endogenous plant DNA adjacent the insert. Generally, the insertion of heterologous genes appears to be random using any transformation technique; however, technology currently exists for producing plants with site specific recombination of DNA into plant cells (see WO/9109957). The particular methods used to transform such plant cells are not critical to this invention, nor are subsequent steps, such as regeneration of such plant cells, as necessary. Any method or combination of methods resulting in the expression of the desired sequence or sequences under the control of the promoter is acceptable.

Conventional technologies for introducing biological material into host cells include electroporation, as disclosed in Shigekawa and Dower (1988), Miller, et al. (1988), and Powell, et al (1988); direct DNA uptake mechanisms, as disclosed in Mandel and Higa (1972) and Dityatkin, et al. (1972), Wigler, et al. (1979) and Uchimiya, et al. (1982); fusion mechanisms, as disclosed in Uchidaz, et al. (1980); infectious agents, as disclosed in Fraley, et al. (1986) and Anderson (1984); microinjection mechanisms, as disclosed in Crossway, et al. (1986); and high velocity projectile mechanisms, as disclosed in EPO 0 405 696.

Plant cells from monocotyledonous or dicotyledonous plants can be transformed according to the present invention. Monocotyledonous species include barley, wheat, maize, oat and sorghum and rice. Dicotyledonous species include tobacco, tomato, sunflower, cotton, sugarbeet, potato, lettuce, melon, soybean and canola (rapeseed).

The appropriate procedure to transform a selected host cell may be chosen in accordance with the host cell used. Based on the experience to date, there appears to be little difference in the expression of genes, once inserted into cells, attributable to the method of transformation itself. Once introduced into the plant tissue, the expression of the structural gene may be assayed in a transient expression system, or it may be determined after selection for stable integration within the plant genome.

Techniques are known for the in vitro culture of plant tissue, and in a number of cases, for regeneration into whole plants. The appropriate procedure to produce mature transgenic plants may be chosen in accordance with the plant species used. Regeneration varies from species to species of plants. Efficient regeneration will depend upon the medium, on the genotype and on the history of the culture. Once whole plants have been obtained, they can be sexually or clonally reproduced in such a manner that at least one copy of the sequence is present in the cells of the progeny of the reproduction. Seed from the regenerated plants can be collected for future use, and plants grown from this seed. Procedures for transferring the introduced gene from the originally transformed plant into commercially useful cultivars are known to those skilled in the art.

EXAMPLE 1

Characterization of A Maize Root-Preferential Cationic Peroxidase

The presence of peroxidase activity can be detected in situ in sodium dodecyl sulfate polyacrylamide gels (SDS-PAGE) by incubation with $H_2O_2$ and a chromogenic substrate such as 3,3'-diaminobenzidine. Tissue specific peroxidase activity was detected by extraction of proteins from root, stem and leaf tissue of maize followed by detection in gels according to Nakamura et al. (see Nakamura et al. (1988)) essentially as follows. One gram of maize tissue was macerated in mortar in 1 mL extraction buffer, composed of 62.5 mM TrisHCl pH 6.8, 5 mM $MgCl_2$, 0.5 M sucrose, and 0.1% ascorbic acid, centrifuged and passed over 0.2 $\mu$M filter to remove plant debris. Total protein was determined using the Bradford protein assay. See Bradford (1976). Ten micrograms of protein of each tissue was electrophoresed on a SDS-poly acrylamide gel. Beta-mercaptoethanol was omitted from the sample buffer to retain enzyme activity. Following electrophoresis the gel was washed two times in 50 mM TrisHCl pH 7.5 for 30 minutes each to remove SDS, and then incubated in the assay solution, which was composed of 50 mM TrisHCl pH 7.5, 0.5 mg/mL diamino benzidine and 0.01% hydrogen peroxide for 10 minutes. Bands corresponding to peroxidase activity were visualized by the formation of a brown precipitate. Non-reduced molecular weight markers (Amersham Corporation) were run in a parallel lane and visualized by standard protein staining in a separate incubation with Coomassie Brilliant Blue. Peroxidase activity in the gel corresponding to a band migrating at approximately 44 kD was only detected in root tissue and was not present in either leaf or stem tissue. Identical patterns of peroxidase staining were produced when several different maize genotypes were examined for root-specific peroxidase isozymes (B37xH84, Pioneer Hybrid 3737, B73).

EXAMPLE 2

Isolation of cDNA Clones Encoding the Maize Root-Preferential Cationic Peroxidase A. RNA Isolation, cDNA Synthesis and Library Construction Maize kernels (Zea mays hybrid B37xH84) were germinated on filter paper under sterile conditions. At 6 days post germination root tissue was harvested and frozen in liquid nitrogen and ground in a mortar and pestle until a fine powder was obtained. The powder was added to 10 mLs of TLE buffer (0.2 M Tris HCl pH 8.2, 0.1 M LiCl, 5 mM EDTA) containing 1% SDS and extracted with 50 mLs of TLE equilibrated phenol and 50 mLs of chloroform. The extraction was incubated on ice for 45 minutes with shaking, and subsequently incubated at 50° C. for 20 minutes. The aqueous phase was transferred to a clean centrifuge tube following centrifugation, and reextracted twice with one half volume of phenol/chloroform (1:1), followed by extractions with chloroform. RNA was precipitated from the aqueous phase by addition of one third volume of 8 M LiCl and incubation at 4° C. for 24 hrs. The precipitate was collected by centrifugation, washed with 2M LiCl and resuspended in 12 mLs of water. RNA was reprecipitated by addition of an equal volume of 4 M LiCl, incubation at 4° C. for 24 hrs and centrifugation. The RNA pellet was resuspended in 2 mL of water and ethanol precipitated by addition of 200 $\mu$l 3 M Na Acetate and 5.5 mL of ethanol and 16 hr incubation at −20° C., followed by centrifugation. The final RNA pellet was resuspended in 1 mL water. The concentration of the RNA was determined using measurement of the absorption at 260 nm. Messenger RNA was purified by binding to and subsequent elution of polyA Quickkit™ columns exactly as described by the supplier (Stratagene Cloning Systems, La Jolla, Calif.). The concentration was determined by A260 measurement. cDNA was synthesized from 5 micrograms of polyA+RNA using the ZAP-cDNA® synthesis kit, cloned into the Uni-ZAP® vector, packaged into phage heads using Stratagene Gigapack Gold® packaging extracts and infected and amplified on E. coli strain PLK-F' exactly according to the protocols provided by the supplier (Stratagene). The titer of the resulting amplified library was determined by plating on PLK-F' cells and was determined at $2.7 \times 10^9$ plaque forming units (pfu)/mL.

B. Isolation of a Peroxidase Hybridization Probe. A hybridization probe corresponding to a central portion of peroxidase cDNA sequences was isolated as follows. Sequence analysis of a number of cloned peroxidases indicated that there are several domains in the predicted and/or determined amino acid sequences that are highly conserved. See Lagrimini and Rothstein (1987). Two degenerate oligonucleotide primers were synthesized against two conserved domains, taking in account a bias for C or G over A or T in the third codon position in maize. Part of the first conserved domain, FHDCFVNGC corresponding to amino acids 41 through 49 of the tobacco peroxidase (see Lagrimini and Rothstein (1987)) was reverse translated into the degenerate oligonucleotide MM1: 5'-TTYCAYGAYTGYTTYGTYAAYGGBTG-3' (SEQ ID NO 3). Part of a second conserved domain, VALSGAHT (corresponding to amino acids 161 through 168 of the tobacco peroxidase (see Lagrimini and Rothstein (1987)) was reverse translated and reverse complemented to give the degenerate oligonucleotide MM3: 5'-SGTRTGSGCSCCGSWSAGVGCSAC-3' (SEQ ID NO 4). In both oligonucleotides, Y indicates the degeneracy C and T; R indicates A and G, S indicates C and G; W indicates A and T; V indicates A, C, and G; and B indicates C ,G, and T;

Using the Polymerase Chain Reaction™ kit (Perkin Elmer Cetus) a 380 bp DNA fragment was amplified using total root cDNA library DNA as template. The size of this fragment corresponded well to the expected size based on the distance of the two domains in peroxidase proteins, 128 amino acids corresponding to 384 nt. Following gel purification the 380 nt fragment was radiolabeled using random primer labeling with an Oligo Labeling™ kit (Pharmacia LKB Biotechnology, Inc, Piscataway, N.J.) as per the supplier's instructions with $_{[D1]}$50 microCuries [$\alpha$-$^{32}$P]dCTP.

C. Screening of the Root cDNA Library. Two hundred thousand phages were plated on E. coli XL1 Blue cells (Stratagene) divided over ten plates. Duplicate plaque lift filters were made of each plate. Filters were prehybridized and hybridized in a total volume of 150 mLs of hybridization solution according to standard procedures (Sambrook et al. 1989). The approximate concentration of labelled probe in the hybridization was $2.20 \times 10^5$ cpm/mL. Following hybridization filters were washed according to standard procedures, air dried, covered and exposed to Kodak XAR5 film. Signals were determined positive if they occurred in the same position on the two duplicate filters of one plate relative to the markings. Putative positive phage were cored out of the plate and stored in 1 mL of SM buffer. Thirty four positive phage were rescreened twice to obtain a pure phage stock using similar hybridization experiments as described above. DNA from all 34 positive phage cDNA clones was prepared by alkaline lysis minipreps following in vivo rescue of phagemids according to the protocol provided by the supplier (Stratagene) and digested with EcoRI and XhoI to release inserts. All plasmids contained one insert in the size range of 1.3–1.4 kb which hybridized with the 380 nt peroxidase probe.

EXAMPLE 3

Analysis of Maize Root-preferential Cationic Peroxidase cDNA Clone per5

A. Analysis of Expression Pattern by Northern Hybridization. RNA was prepared from root, stem, leaf, kernel and tassel tissue as described in Example 2, section A. Thirty micrograms of denatured total RNA of each tissue was electrophoresed on a 1% agarose/Na phosphate gel and transferred to nylon membrane and prehybridized and hybridized with the labeled 380 nt peroxidase probe according to standard procedures. A ~1470 nt transcript was detected in root and stem RNA, but was absent from leaf, kernel and tassel RNA. The level of the detected transcript in roots was at least 5.5 fold higher than in stem tissue.

B. Sequence Analysis of the per5 cDNA Clone. Both strands of dsDNA from the cDNA clone with the longest insert (per5) were sequenced using the Sequenase™ sequencing kit (United States Biochemical, Cleveland, Ohio). Sequencing was started using the T3 and T7 primers and completed by walking along the DNA using sequencing primers designed based on sequence derived in previous runs. The sequence of the per5 cDNA insert is shown in SEQ ID NO 5. The per5 cDNA insert is 1354 nucleotides (nt) in length and has a 5'-untranslated leader of 52 nt and a 275 nt 3' untranslated sequence before the start of polyadenylation. It also contains the animal consensus polyadenylation signal sequence AATAAA 34 nucleotides prior to the addition of a 28 nucleotide poly(A) tail. The cDNA has an open reading frame of 999 bp, which spans between nucleotides 53 and 1051. The first ATG codon in the cDNA sequence was chosen as the start of translation. The predicted size of the mature maize peroxidase is 301 amino acids with a MW of 32,432 and an estimated pI of 9.09. The N-terminus of the mature protein was assigned by alignment of the maize amino acid sequence with other published sequences and known N-terminal sequences obtained by N-termal amino acid sequencing. It is predicted from the cDNA sequence that the protein is initially synthesized as a preprotein of MW 35,685 with a 32-amino acid signal sequence that is 72% hydrophobic. The presence of this signal sequence, which has also been observed in several other plant peroxidases, suggests that the protein is taken up in the endoplasmic reticulum and modified for sub-cellular targeting or secretion. This is supported by the presence of four potential N-glycosylation sites (Asn-Xaa-Thr/Ser), which are at residues 53, 138, 181 and 279 of the putative mature protein. The presence of four putative N-glycosylation sites suggest a role for post-translational modification (eg. glycosylation) and explains the discrepancy in the observed (~44 kD) and predicted size of the mature protein (~36 kD). Comparison of the deduced amino acid sequences of the maize per5 cDNA with the published sequences of wheat (see Hertig et al. (1991)), horseradish [C1] (see Fujiyama et al. (1988)), turnip [TP7] (see Mazza and Welinder (1980)), peanut [PNC1] (see Buffard et al. (1990)), tobacco (see Lagrimini et al. (1987)), and cucumber (see Morgens et al. (1990)) confirms that per5 encodes a peroxidase protein. There is >80% to >92% sequence similarity between these seven plant peroxidases in four conserved domains. All seven peroxidases have eight cysteines, conserved in position in the primary sequence. These cysteines in the horseradish and turnip enzymes have been shown to be involved in intramolecular disulfide linkages.

EXAMPLE 4

Isolation of the Maize Root-preferential Cationic Peroxidase Genomic Clone

A. Genomic DNA Blot Hybridization. Genomic DNA was isolated from a maize diploid, homozygous line (B73). The DNA was digested with the restriction enzymes EcoRI, HindIII, and SacI, fractionated on a 1% agarose gel, subjected to transfer to membrane and hybridization to both a $^{32}$P-labeled per5 full-length cDNA and a per5 cDNA gene-specific probe (GSP5). The 136 bp GSP5 probe was amplified by PCR using the per5 cDNA clone as template DNA and primers MM21: 5'-GTCATAGAACTGTGGG-3' (SEQ ID NO 6); and MM22: 5'-ATAACATAGTACAGCG-3' (SEQ ID NO 7). This probe is composed of nt 25–160 of the per5 cDNA clone and includes 27 bp of the 5' untranslated sequence, the entire coding sequence for the putative endoplasmic reticulum signal peptide and 7 bp which code for the amino-terminus of the putative per5 mature domain.

Using the per5 cDNA full length probe two strong hybridization signals were detected in each digest. This suggested that the per5 gene may be present in two copies per haploid genome. However, using GSP5 as a probe only one band per lane was detected which suggested that there is only one copy of the per5 gene per haploid genome and that the other hybridizing band on the genomic DNA blot corresponds to more distantly related sequences. This also demonstrated that probe GSP5 was gene specific and would be suitable for the isolation of the peroxidase genomic clone from a maize genomic library.

B. Isolation of the Root-preferential Cationic Peroxidase Gene from a Maize W22 Library. Approximately $2 \times 10^6$ plaques of a maize W22 genomic library (Clontech Laboratories, Inc., Palo Alto, Calif.) were screened using GSP5 as the probe according to standard protocol for library screening. GSP5 was used as probe because it would recognize only the genomic clones corresponding to the per5 cDNA clone. Ten genomic clones were isolated and plaque purified. The clones were plate amplified to increase their titers, liquid lysates were grown up and phage DNA was isolated from these cultures. Restriction analysis on nine of the ten clones using SalI, which liberates the genomic DNA inserts from the phage arms, showed that eight of the nine clones had the same SalI banding pattern. These eight clones contained ~14.9 Kb inserts which could be cut into two SalI fragments of ~10.4 Kb and ~4.5 Kb, respectively. The ninth clone (perGEN19) contained an ~15.6 Kb insert which upon SalI digestion yields two fragments, ~13.1 Kb and ~2.5 Kb in size. Restriction and DNA hybridization analysis suggest that perGEN19 contains an insert which overlaps with the Sau3A inserts of the other 8 clones. A representative of the eight identical genomic clones (perGEN1) was further analyzed. The ~10.4 Kb fragment was subcloned into the SalI site of the plasmid pBluescript®II SK(−) (Stratagene, Inc.) generating plasmid perGEN1(10.44). Restriction digests (using ApaI, BamHI, EcoRI, HindIII, KpnI, NcoI, SacI, and XbaI) and DNA blot hybridization analyses (using either the full-length per5 cDNA or GSP5 as probes) indicated that the 10.44 Kb SalI fragment on perGEN1 contained the peroxidase sequences. Further restriction digests using single and double digests of HindIII, KpnI, SacI, and XbaI and DNA blot hybridization analyses using gel-purified KpnI perGEN1(10.44) fragments as probes was performed on perGEN1(10.44).

EXAMPLE 5

Sequence of the Maize Root-preferential Cationic Peroxidase Gene

A total of 6550 nt of genomic sequence covering the maize root-preferential cationic peroxidase gene and its 5' and 3' flanking sequences was obtained by sequencing overlapping subfragments of plasmid perGEN1(10.44) which hybridized with the GSP5 probe described in Example 3 as well as the per5 cDNA insert. The sequence is shown in SEQ ID NO 1. The sequencing procedures were standard techniques known to those skilled in the art. The upstream flanking region from the 5'-most NcoI site to the putative start site of translation was determined to be 4200 nt in length. The maize root-preferential cationic peroxidase gene is composed of exons: exon 1 (225 bp), exon 2 (192 bp), exon 3 (166 bp), and exon 4 (416 bp). The GC-content of the exons is 54.7%. The sequence of the compiled exon sequences was 100% identical to that of the coding region for the per5 cDNA. Translation of these exons resulted in a deduced protein sequence that is 100% identical to the deduced protein sequence for the per5 cDNA sequence. Three introns were found: intron 1 (633 bp, % AU=62.7, % U=33.8), intron 2 (132 bp, % AU=63.6, % U=35.6), and intron 3 (101 bp, % AU=65.3, % U=37.6). The downstream flanking region from the UGA codon to the 3' most XbaI site was found to be 373 bp in length. The intron splice sites did not fit the putative monocot 5' and 3' splice site consensus sequences perfectly, but did follow the mammalian "GU/AG rule" for splice sites. The intron sequences also conformed to the definition of maize intron sequences suggested by Walbot. See Walbot et al. (1991).

EXAMPLE 6 pDAB406

This Example describes pDAB406, a vector designed for testing of promoter activity in both transient and stable transformation experiments. The complete sequence for pDAB 406 is given in SEQ ID NO 8. With reference to SEQ ID NO 8, significant features of pDAB406 are given in Table 1.

TABLE 1

Features of pDAB 406

| nt (SEQ ID NO 8) | Features |
|---|---|
| 1–6 | ApaI site |
| 7–24 | multiple cloning site (NheI, KpnI, SmaI) |

TABLE 1-continued

Features of pDAB 406

| nt (SEQ ID NO 8) | Features |
|---|---|
| 25–30 | SalI site |
| 32–1840 | E. coli uidA reporter gene encoding the beta-glucuronidase protein (GUS) from pKA882 and TGA stop codon |
| 1841–1883 | 3' untranslated region from pBI221 |
| 1894–1899 | SsI site |
| 1900–2168 | nopaline synthetase 3' polyA sequence (nos 3'UTR) |
| 2174–2179 | HindIII site |
| 2180–2185 | BglII site |
| 2186–2932 | a modified CaMV 35S promoter |
| 2195–2446 | MCASTRAS nt 7093–7344 |
| 2455–2801 | MCASTRAS nt 7093–7439 |
| 2814–2932 | Synthetic Maize Streak Virus (MSV) untranslated leader containing the maize Adh1 intron 1 |
| 2933–2938 | BglII/BclI junction |
| 2933–3023 | Adh1.S nt 269–359 MZEADH1.S |
| 3024–3141 | Adh1.S nt 704–821 MZEADH1.S |
| 3146–3151 | BamHI/BglII juncfion |
| 3150–3187 | synthetic MSV leader containing the maize Adh1 intron 1 |
| 3188–3193 | NcoI |
| 3190–4842 | internal reference gene composed of the firefly luciferase gene (Lux) |
| 4907–5165 | nopaline synthetase 3' polyA sequence (nos 3'UTR) |
| 5172–5177 | BglII site |
| 5178–5183 | NdeI site |
| 5186–5191 | SstI site |
| 5195–5672 | nt 6972–6495 MCASTRAS (CaMV 35S promoter) |
| 5680–6034 | nt 7089–7443 MCASTRAS (CaMV 35S promoter) |
| 6042–7021 | Tn5 nt 1539–2518; mutated 2X |
| 6054–6848 | a selectable marker gene composed of the bacterial NPTII gene encoding neomycin phosphotransferase which provides resistance to the antibiotics kanamycin, neomycin and G418 |
| 7022–7726 | 3' UTR of ORF26 gene Agrobacterium tumifaciens Ti plasmid (pTi 15955, nt 22438 to 21726) |
| 7727–7732 | NdeI site |
| 7733–7914 | pUC19 nt 1–182, reverse complement |
| 7915–10148 | nt 453 to 2686 pUC19, reverse complement |
| 10149–10160 | multiple cloning site, HindIII, SstI |

The vector can readily be assembled by those skilled in the art using well known methods.

EXAMPLE 7 pDAB411

This Example describes plasmid pDAB411, which is a 11784 bp plasmid that has a pUC19 backbone and contains a gene cassette comprising 1.6 kb of per5 promoter, the per5 untranslated leader, the GUS gene, and the nos 3'UTR. No intron is present in the untranslated leader of pDAB411. The complete sequence for pDAB411 is given in SEQ ID NO 9. With reference to SEQ ID NO 9, significant features of pDAB411 are given in Table 2.

TABLE 2

Significant Features of pDAB 411

| nt (SEQ ID NO 9) | Feature |
|---|---|
| 1–6 | ApaI site |
| 7–1648 | Per5 promoter and untranslated leader sequence (corresponding to nt 2559 to 4200 of SEQ ID NO 1) |
| 1649–1654 | SalI site |
| 1656–3464 | E. coli uidA reporter gene encoding the beta-glucuronidase protein (GUS) |

TABLE 2-continued

Significant Features of pDAB 411

| nt (SEQ ID NO 9) | Feature |
| --- | --- |
| 3465–3507 | 3' untranslated region from pBI221 |
| 3518–3523 | SstI site |
| 3524–3792 | nopaline synthetase 3' polyA sequence (nos 3'UTR) |
| 3793–11784 | corresponds to 2169 to 10160 of pDAB 406 SEQ ID NO 8 |

Preliminary testing of pDAB411 in transgenic maize plants failed to demonstrate appreciable GUS expression. This failure is consistent with our discovery that certain tissue preferential maize promoters require the presence of an intron in the transcribed portion of the gene for significant expression to be observed.

EXAMPLE 8 pDAB419

This Example describes construction of Plasmid pDAB419, which is a 11991 bp plasmid that is identical to pDAB411, except that the untranslated leader preceding the GUS gene includes a 207 bp sequence comprising a deleted version the maize Adh1 intron 1. The complete sequence for pDAB419 is given in SEQ ID NO 10. With reference to SEQ ID NO 10, critical features of pDAB419 are as follows:

TABLE 3

Critical Features of pDAB 419

| nt (SEQ ID NO 10) | Feature |
| --- | --- |
| 1–6 | ApaI site |
| 7–1648 | Per5 promoter and untranslated leader sequence (corresponding to nt 2559 to 4200 of SEQ ID NO 1) |
| 1649–1855 | deleted version of maize Adh1 intron 1 corresponding to nt 2939–3145 of SEQ ID NO 8 |
| 1856–1861 | SalI site |
| 1863–3671 | E. coli uidA reporter gene encoding the beta-glucuronidase protein (GUS) |
| 3672–3714 | 3' untranslated region from pBI221 |
| 3725–3730 | SstI site |
| 3731–3999 | nopaline synthetase 3' polyA sequence (nos 3'UTR) |
| 4000–11991 | corresponds to 2169 to 10160 of pDAB 406 SEQ ID NO 8 |

Plasmid pDAB419 was constructed from pDAB411 using conventional techniques. More specifically, the per5 promoter in plasmid pDAB411 was amplified with primers MM88: 5'-ACGTACGTACGGGCCCACCACTGTTGTAACT TGTAAGCC-3' (SEQ ID NO 11) and OF192: 5' AGGCG-GACCTTTGCACTGTGA GTTACCTTCGC-3' (SEQ ID NO 12). The modified Adh1 intron 1, corresponding to nt 2939 to 3145 of SEQ ID NO 8. was amplified from plasmid pDAB406 using primers OF190: 5'-CTCTGTCGACGAGCGCAGCTGCAC GGGTC-3' (SEQ ID NO 13) and OF191: 5'-GCGAAGGTAACTCACAGTGCAAAGGTCCGCCT-3' (SEQ ID NO 14). Following amplification both fragments were purified through a 1% agarose gel. Splice Overlap Extension PCR was used to join the per5 promoter fragment to the Adh1 intron 1 fragment. Samples (2.5 μL) of each gel-purified fragment were mixed and re-amplified using primers MM88 and OF192 (SEQ ID NOS 11 and 12). The resulting 1.6 kB per5adh fragment was digested with ApaI and SalI, gel-purified, and ligated into pDAB406 which was digested with ApaI and SalI resulting in an 11,991 bp plasmid, pDAB419.

EXAMPLE 9

Transformation of Rice with pDAB419

This example describes transformation of rice with pDAB419, and the histochemical and quantitative patterns of GUS expression in the transformed rice plants.

A. Transgenic Production.

1. Plant Material and Callus Culture. For initiation of embryogenic callus, mature seeds of a Japonica cultivar, Taipei 309 were dehusked and surface-sterilized in 70% ethanol for 2–5 min. followed by a 30–45 min soak in 50% commercial bleach (2.6% sodium hypochlorite) with a few drops of 'Liquinox' soap. The seeds were then rinsed 3 times in sterile distilled water and placed on filter paper before transferring to 'induction' media (NB). The NB medium consisted of N6 macro elements (Chu, 1978), B5 micro elements and vitamins (Gamborg et al., 1968), 300 mg/L casein hydrolysate, 500 mg/L L-proline, 500 mg/L L-glutamine, 30 g/L sucrose, 2 mg/L 2,4-dichloro-phenoxyacetic acid (2,4-D), and 2.5 g/L Gelrite (Schweizerhall, N.J.) with a pH adjusted to 5.8. The mature seed cultured on 'induction' media were incubated in the dark at 28° C. After 3 weeks of culture, the emerging primary callus induced from the scutellar region of mature embryo was transferred to fresh NB medium for further maintenance.

2. Plasmids and DNA Precipitation. pDAB354 containing 35T-hpt (hygromycin phosphotransferase providing resistance to the antibiotic hygromycin; (described in Example 25) was used in cotransformations with pDAB419. About 140 μg of DNA was precipitated onto 60 mg of gold particles. The plasmid DNA was precipitated onto 1.5–3.0 micron (Aldrich Chemical Co., Milwaukee, Wis.) or 1.0 micron (Bio-Rad) gold particles. The precipitation mixture included 60 mg of pre-washed gold particles, 300 μL of water/DNA (140 μg), 74 μL of 2.5 M $CaCl_2$, and 30 μL of 0.1 M spermidine. After adding the components in the above order, the mixture was vortexed immediately, and allowed to settle for 2–3 min. Then, the supernatant was pipetted off and discarded. The DNA-coated gold particles were resuspended in 1 mL of 100% ethanol and diluted to 17.5 μg DNA/7.5 mg gold per mL of ethanol for use in blasting experiments.

3. Helium Blasting into Embryogenic Callus and Selection. Actively growing embryogenic callus cultures, 2–4 mm in size, were subjected to a high osmoticum treatment. This treatment included placing of callus on NB medium with 0.2 M mannitol and 0.2 M sorbitol (Vain et al., 1993) for 4 hrs before helium blasting. Following osmoticum treatment, callus cultures were transferred to 'blasting' medium (NB+ 2% agar) and covered with a stainless steel screen (230 micron). Helium blasting involved accelerating the suspended DNA-coated gold particles towards and into the prepared tissue targets. The device used was an earlier prototype to the one described in U.S. Pat. No. 5,141,131 which is incorporated herein by reference, although both function in a similar manner. The callus cultures were blasted at different helium pressures (1,750–2,250 psi) once or twice per target. After blasting, callus was transferred back to the media with high osmoticum overnight before placing on selection medium, which consisted of NB medium with 30 mg/L hygromycin. After 2 weeks, the cultures were transferred to fresh selection medium with higher concentrations of selection agent, i.e., NB+50 mg/L hygromycin (Li et al., 1993).

4. Regeneration. Compact, white-yellow, embryogenic callus cultures, recovered on NB+50 mg/L hygromycin, were regenerated by transferring to 'pre-regeneration' (PR) medium+50 mg/L hygromycin. The PR medium consisted of NB medium with 2 mg/L 6-benzylaminopurine (BAP), 1 mg/L naphthaleneacetic acid (NAA), and 5 mg/L abscisic acid (ABA). After 2 weeks of culture in the dark, they were transferred to 'regeneration' (RN) medium. The composition of RN medium is NB medium with 3 mg/L BAP, and 0.5 mg/L NAA. The cultures on RN medium were incubated for 2 weeks at 28° C. under high fluorescent light (325-ft-candles). The plantlets with 2 cm shoot were transferred to ½ MS medium (Murashige and Skoog, 1962) with ½ B5 vitamins, 10 g/L sucrose, 0.05 mg/L NAA, 50 mg/L hygromycin and 2.5 g/L Gelrite adjusted to pH 5.8 in magenta boxes. When plantlets were established with well-developed root system, they were transferred to soil (1 metromix: 1 top soil) and raised in a growth chamber or greenhouse (29/24° C. day/night cycle, 50–60% humidity, 12 h photoperiod) until maturity. A total of 23 hygromycin-resistant callus lines were established.

B. GUS Histochemical Assays

GUS histochemical assays were conducted according to Jefferson (1987). Tissues were placed in 24-well microtitre plates (Corning, New York, N.Y.) containing 500 μL of assay buffer per well. The assay buffer consisted of 0.1 M sodium phosphate (pH 8.0), 0.5 mM potassium ferricyanide, 0.5 mM potassium ferrocyanide, 10 mM sodium EDTA, 1.9 mM 5-bromo-4-chloro-3-indolyl-beta-D-glucuronide, and 0.06% triton X-100. The plates were incubated in the dark for 1–2 days at 37° C. before observations under a microscope. Fourteen of the 23 hygromycin resistant rice lines expressed the GUS gene as evidenced by blue staining after 48 hours in the GUS histochemical assay. Nine of the 14 GUS expressing lines were further characterized (Table 4).

TABLE 4

Histochemical GUS Staining of Transgenic Rice Callus

| Line | Rating |
|---|---|
| 354/419-03 | ++++ |
| 354/419-04 | ++++ |
| 354/419-07 | ++++ |
| 354/419-11 | +++ |
| 354/419-12 | ++ |
| 354/419-13 | +++ |
| 354/419-15 | ++ |
| 354/419-18 | +++ |
| 354/419-21 | ++ |

+ = Occasional blue region
++ = Light blue staining throughout
+++ = Dark blue regions
++++ = Intense blue staining throughout C. Southern Analysis Southern analysis was used to identify primary regenerate (Ro) plant lines from rice that contained an intact copy of the transgene and to measure the complexity of the integration event. Several leaves from each rice plant were harvested and up to five plants were sampled individually from each line. Genomic DNA from the rice Ro plants was prepared from lyophilized tissue as described by Saghai-Maroof et al. (1984). Eight micrograms of each DNA was digested with the restriction enzyme XbaI using conditions suggested by the manufacturer (Bethesda Research Laboratory, Gaithersburg, Md.) and separated by agarose gel electrophoresis. The DNA was blotted onto nylon membrane as described by Southern (1975, 1980).

A probe specific for β-glucuronidase (GUS) coding region was excised from the pDAB419 plasmid using the restriction enzymes NcoI and SstI. The resulting 1.9 kb fragment was purified with the Qiaex II DNA purification kit (Qiagen Inc., Chatsworth, Calif.). The probe was prepared using an oligo-labeling kit (Pharmacia LKB, Piscataway, N.J.) with 50 microcuries of $\alpha^{32}$P-dCTP (Amersham Life Science, Arlington Heights, Ill.). The GUS probe hybridized to the genomic DNA on the blots. The blots were washed at 60° C. in 0.25×SSC and 0.2% SDS for 45 minutes, blotted dry and exposed to XAR-5 film overnight with two intensifying screens.

D. GUS Quantification

1. Tissue Preparation. Histochemically GUS positive plantlets, grown in Magenta boxes, were dissected into root and leaf tissues. Duplicate samples of approximately 300 mg root and 100 mg leaf were transferred to a 1.5 ml sterile sample tube (Kontes, Vineland, N.J.) and placed on ice prior to freezing at −80° C. Extraction of proteins consisted of grinding tissue using a stainless steel Kontes Pellet Pestle powered by a 0.35 amp, 40 Watt motor (Model 102, Rae Corp., McHenry, Ill.), at a setting of "40". GUS Lysis buffer from the GUS-Light™ assay kit (Tropix, Bedford, Mass.) was modified with the addition of 20% glycerol to produce the extraction buffer. Before grinding, frozen samples were placed on ice and aliquots of 100 μl extraction buffer were added to the sample tube. Tissue was homogenized in approximately four 25-second intervals during which additional aliquots of extraction buffer were added for a final volume of 300 μl for root and 200 μl for leaf tissues. Samples were maintained on ice until all sample grinding was completed. Samples were then centrifuged twice at 5° C. for 8 minutes at full speed (Eppendorf Centrifuge Model 5415). Supernatant was transferred to sterile microcentrifuge tubes on ice and later used to quantitate proteins and GUS; the pellet was discarded.

2. Total Protein Quantification. Quantification of extractable proteins was determined with the Bio-Rad Protein Assay kit (Bio-Rad Laboratories, Hercules, Calif.). A protein standard made from bovine albumin (Sigma, St. Louis, Mo.) was used to obtain a standard curve from zero to 10 μg/ml. Duplicate samples for each tissue were prepared using 5 μl of protein extract with 5 μl GUS lysis buffer in a sterilized microcentrifuge tube. Water was added to bring the volume up to 800 μl before 200 μl dye reagent was added. Tubes were vortexed, then incubated at room temperature for at least 5 minutes before the liquid was transferred into 1.5 ml cuvetts and place in the spectrophotometer (Shimadzu, Japan). Absorbance measurements were made at 595 nm.

3. GUS Quantification. Analysis of GUS activity required the use of the GUS-Light™ assay kit and an automatic luminescence photometer (Model 1251 Luminometer and Model 1291 Dispenser, Bio-Orbit, Finland). For each sample, a relative level of GUS activity was measured on 1 μl extract. From the initial reading, sample volumes were scaled up between 2 and 10 μl of extract per luminometer vial while remaining within the detection limits of the equipment. Samples were prepared in triplicate to which 180 μl aliquots of GUS-Light™ reaction buffer was added to each luminometer vial at 10-second intervals. After a one hour incubation at room temperature in the dark, the vials were loaded into the sample holder of the luminometer. As each vial entered the measuring chamber, 300 μl of GUS-Light™ Light Emission Accelerator Buffer was added and luminescence was detected over a 5-second integration period. A "blank reaction" was included in the assay, using 10 μl of the GUS extraction buffer. A GUS standard, prepared to read 8,000 relative light units (RLU) from commercially available β-glucuronidase (Sigma, Mo.), was used to confirm the sensitivity of the equipment and reagents used. GUS readings (RLU) were corrected for the "blank" and the GUS standard readings before dividing by μg total protein.

TABLE 5

GUS Expression in Rice Plants Transformed with pDAB 419

| Line | Presence of Intact Construct | Number of Hybridization Products | Relative light units per mg protein | |
|---|---|---|---|---|
| | | | Root | Leaf |
| 354/419-03 | yes | 10 | n.d. | n.d. |
| 354/419-04 | yes | 4 | 795 | 579 |
| 354/419-07 | yes | 1 | 22341 | 23407 |
| 354/419-11 | n.d. | n.d. | 1077 | 215 |
| 354/419-12 | n.d. | n.d. | n.d. | n.d. |
| 354/419-13 | yes | 9 | 736 | 346 |
| 354/419-15 | yes | 2 | 208 | 208 |
| 354/419-18 | yes | 7 | 230 | 62 |
| 354/419-21 | yes | 3 | 186 | 56 | n.d = not determined

Rice plants regenerated from transgenic callus stained positively for GUS in both roots and leaves indicating constitutive expression. It was not expected that constitutive expression of GUS would be observed from the pDAB419 construct because of the lack of expression in the leaves of the native per5 gene in maize.

EXAMPLE 10

Transformation of Maize with pDAB419

A. Establishment of Type II Callus Targets.

Two parents of 'High II' (Armstrong and Phillips, (1991)) were crossed and when the developing embryos reached a size of 1.0–3.0 mm (10–14 days after pollination), the ear was excised and surface sterilized. Briefly, ears were washed with Liquinox soap (Alconox, Inc., NY) and subjected to immersions in 70% ethanol for 2–5 minutes and 20% commercial bleach (0.1% sodium hypochlorite) for 30–45 minutes followed by 3 rinses in sterile, distilled water. Immature embryos were isolated and used to produce Type II callus.

For Type II callus production, immature embryos were placed (scutellum-side up) onto the surface of 'initiation' medium (15Ag10) which included N6 basal salts and vitamins (Chu, 1978), 20 g/L sucrose, 2.9 g/L L-proline, 100 mg/L enzymatic casein hydrolysate (ECH), 37 mg/L Fe-EDTA, 10 mg/L silver nitrate, 1 mg/L 2,4-dichlorophenoxyacetic acid (2,4-D), and 2.5 g/L Gelrite (Schweizerhall, N.J.) with pH adjusted to 5.8. After 2–3 weeks incubation in the dark at 28° C., soft, friable callus with numerous globular and elongated somatic embryo-like structures (Type II) were selected. After 2–3 subcultures on the 'initiation' medium, callus was transferred to 'maintenance' medium (#4). The 'maintenance' medium differed from the 'initiation' medium in that it contained 690 mg/L L-proline and no silver nitrate. Type II callus was used for transformation experiments after about 16–20 weeks.

B. Helium Blasting and Selection.

pDAB367 (Example 27) and pDAB419 were co-precipitated onto the surface of 1.5–3.0 rnicron gold particles (Aldrich Chem. Co., Milwaukee, Wis.). pDAB367 contains a phosphinothricin acetyl transferase gene fusion which encodes resistance to the herbicide Basta.™ This gene is used to select stable transgenic events. The precipitation mixture included 60 mg of pre-washed gold particles, 140 μg of plasmid DNA (70 μg of each) in 300 μL of sterile water, 74 μL of 2.5 M CaCl$_2$, and 30 μL of 0.1 M spermidine. After adding the components in the above order, the mixture was vortexed immediately, and allowed to settle for 2–3 minutes. The supernatant was removed and discarded and the plasmid/gold particles were resuspended in 1 mL of 100% ethanol and diluted to 7.5 mg plasmid/gold particles per mL of ethanol just prior to blasting.

Approximately 400–600 mg of Type II callus was placed onto the surface of #4 medium with 36.4 g/L sorbitol and 36.4 g/L M mannitol for 4 hours. In preparation for blasting, the callus was transferred to #4 medium with 2% agar (JRH Biosciences, Lenexa, Kans.) and covered with a stainless steel screen (104 micron). Helium blasting was completed using the same device described in Example 9. Each callus sample was blasted a total of four times. After blasting the callus was returned to #4 medium with 36.4 g/L sorbitol and 36.4 g/L mannitol for 18–24 hours after which it was transferred to 'selection' medium (#4 medium with 30 mg/L Basta™ and no ECH or L-proline). The callus was transferred to fresh 'selection' medium every four weeks for about three months. After 8–12 weeks, actively growing transgenic colonies were isolated and sub-cultured every two weeks on fresh 'selection' medium to bulk-up callus for regeneration.

C. Histochemical GUS Assay.

Basta™-resistant callus was analyzed for GUS expression by incubating a 50 mg sample in 150 μL of assay buffer for 48 hours at 37° C. The assay buffer consisted of 0.2 M sodium phosphate pH 8.0, 0.5 mM each of potassium ferricyanide and potassium ferrocyanide, 10 mM sodium EDTA, 1.9 mM 5-bromo-4-chloro-3-indolyl-b-D-glucuronide, and 0.06% v/v Triton x-100 (Jefferson et al., 1987). Transgenic callus expressing the GUS gene turned blue. A total of 17 Basta™-resistant callus lines were established for maize, with three maize lines expressing the GUS gene as evidenced by blue staining after 48 hours in the GUS histochemical assay.

TABLE 6

Histochemical GUS Staining of Transgenic Maize Callus

| Line | rating |
|---|---|
| 311/419-01 | + |
| 311/419-02 | +++ |
| 311/419-16 | +++ |

+ = Occasional blue region
++ = Light blue staining throughout
+++ = Dark blue regions
++++ = Intense blue staining throughout There was considerable variability in intensity of staining among the expressing callus ranging from very intense to somewhat spotty (Table 6). Generally, callus staining was more intense in rice than in maize.

D. Plant Regeneration.

GUS-expressing callus was transferred to 'induction' medium and incubated at 28° C., 16/8 light/dark photoperiod in low light (13 mE/m$^2$/sec) for one week followed by one week in high light (40 mE/m$^2$/sec) provided by cool white fluorescent lamps. The 'induction' medium was composed of MS salts and vitamins (Murashige and Skoog (1962)), 30 g/L sucrose, 100 mg/L myo-inositol, 5 mg/L 6-benzylamino purine, 0.025 mg/L 2,4-D, 2.5 g/L Gelrite (Schweizerhall, N.J.) adjusted to pH 5.7. Following this two-week induction period, the callus was transferred to 'regeneration' medium and incubated in high light (40 mE/m$^2$/sec) at 28° C. The 'regeneration' medium was composed of MS salts and vitamins, 30 g/L sucrose, and 2.5 g/L Gelrite (Schweizerhall, N.J.) adjusted to pH 5.7. The callus was sub-cultured to fresh 'regeneration' medium every two weeks until plantlets appeared. Both 'induction' and 'regeneration' medium contained 30 mg/L Basta™. Plantlets were transferred to 10 cm pots containing approximately 0.1 kg of dry Metro-Mix (The Scotts Company, Marysville, Ohio), moistened thoroughly, and covered with clear plastic cups for approximately 4 days. At the 3–5 leaf stage, plants were transplanted to 5-gallon pots and grown to maturity.

E. Southern Analysis

A DNA probe specific for the β-glucuronidase (GUS) coding region was excised from the pDAB418 plasmid using the restriction enzymes NcoI and SstI. The 1.9 kb fragment was purified with the Qiaex II DNA purification kit (Qiagen Inc., Chatsworth, Calif.). The probe was prepared using an oligo-labeling kit (Pharmacia LKB, Piscataway, N.J.) with 50 microcuries of a$^{32}$P-dCTP (Amersham Life Science, Arlington Heights, Ill.). Southern analysis was used to identify maize callus material that contained an intact copy of the transgene and to measure the complexity of the integration event. The callus material was removed from the media, soaked in distilled water for 30 minutes and transferred to a new petri dish, prior to lyophilization. Genomic DNA from the callus was prepared from lyophilized tissue as described by Saghai-Maroof et al. (1984). Eight micrograms of each DNA was digested with the restriction enzyme XbaI using conditions suggested by the manufacturer (Bethesda Research Laboratory, Gaithersburg, Md.) and separated by agarose gel electrophoresis. The DNA was blotted onto nylon membrane as described by Southern (1975, 1980). The GUS probe was hybridized to the genomic DNA on the blots. The blots were washed at 60° C. in 0.25×SSC and 0.2% SDS for 45 minutes, blotted dry and exposed to XAR-5 film overnight with two intensifying screens.

F. Screening of $R_o$ Plants for Uniform Expression.

The 6th leaf was collected from five or six "V6-equivalent" stage plants (because of inability of determining exact leaf number from R0 plants, a plant characteristic of the V6 stage was used). The entire leaf was removed, cut into pieces and stored in a plastic bag at −70° C. until further processing. Leaves were powdered in liquid nitrogen and tissues samples representing approximately 400 μL of tissue were placed in microfuge tubes. The tissue was either stored or extracted immediately. GUS was extracted by mixing the powdered tissue with GUS Lysis Buffer (Jefferson, 1987) as modified by the addition of 1% polyvinylpyrrolidone (hydrated in the buffer for at least one hour), 20% glycerol, 50 mg/mL antipain, 50 mg/niL leupeptin, 0.1 mM chymostatin, 5 mg/nL pepstatin and 0.24 mg/mL Pefabloc™ (Boehringer Mannheim, Indianapolis, Ind.). After incubation on ice for at least 10 min, the samples were centrifuged at 16,000 g for 10 min. The supernatants were recovered and centrifuged a second time as described above. The supernatants were recovered and frozen on dry ice and stored at −70° C. Experiments showed that GUS activity was stable for at least 4 freeze-thaw cycles when stored in the buffer described above. GUS activity was measured using a GUS-Light™ kit (Tropix, Inc, Bedford, Mass.). Five μL samples of undiluted extract or of extract diluted so that the luminescence was within the range measured by the luminometer was added to 195 μl of the GUS-Light™ Reaction Buffer. After 1 hr the luminescence was measured using a BioOrbit 1251 luminometer equipped with a BioOrbit 1291 injector after injection of 300 μL of GUS-Light™ Accelerator. Luminescence was integrated for 5 sec after a 5 sec delay. Protein was measured with the assay developed by Bradford (1976) using human serum albumin as the standard.

G. Organ-Specific Expression Quantitative Analyses.

Plants grown in the greenhouse in 5 gallon pots were harvested to determine organ-specificity of GUS expression. Prior to harvesting tissue from V6-equivalent plants, roots were cut approximately one inch from the side of the pot to remove any dead root tissue. Roots from VT stage (mature) plants were washed and any dead root tissue was removed before freezing at −70° C. Leaves, stems (VT-stage plants only) and roots were harvested and either frozen at −70° C. or powdered in liquid nitrogen immediately. Experiments showed that GUS is stable in frozen tissue. After powdering the tissues, three aliquots of approximately 10 ml of tissue were collected into preweighed tubes, and the tubes with tissue weighed and stored at −70° C. Tissue was extracted in the same buffer as described above except protease inhibitors were only added to aliquots of the extracts instead to the entire extract volume. For extraction, the powdered tissues were thawed into 4 ml buffer/g tissue and homogenized for 5–10 sec at 8,000 rpm using a Ultra-Turrax T 25 (IKA-Works, Inc.) homogenizer with an 18 mm probe. The samples were centrifuged at 4° C. for 5 min at 2015 g. After removing the supernatants, the pellets were extracted again but with 2 ml buffer/g tissue and the supernatant after centrifugation was pooled with the supernatant from the first extraction. The pellet was extracted again with 2 ml/g tissue; the supernatant after centrifugation was processed separately from the pooled supernatants from the first two extractions. GUS activity recovered in the final extract was used to determine extraction efficiency of the first two extractions. GUS and protein assays were done as described above for both sets of supernatants. Roots at each node from V7 plants grown in approximately 15 gallon pots were analyzed separately as described above.

H. Histochemical Analyses Staining of Maize Tissues.

Histochemical analyses of per5adh/GUS/nos gene expression was done essentially as described by Jefferson (1987). Roots were first treated 1 h at 37° C. in 100 mM NaPO$_4$ buffer, pH 7.0, 10 mM EDTA, 0.1% Triton X-100 and 10 mM β-mercaptoethanol. The root sections were washed 3 times with the same buffer but without β-mercaptoethanol and then incubated 1hr in the same buffer at 37° C. GUS histochemical assay buffer Jefferson (1987) was added and the tissues were incubated for various times at 37° C. Roots from V6 and VT plants were removed from each node and treated separately. Roots from each node of V6 plants were measured, cut into 6 equal parts, and 2-one centimeter pieces were removed from the ends of each root section. One root piece from each section was stained until the ends were blue; the other piece from each section was stained overnight. Roots from VT plants were stained similarly, but two roots from each node, if available, were cut into several pieces and stained together. One root from each node was stained until the roots turned blue; the other root from each node was stained overnight. One intact leaf was removed from the bottom, middle and top of the V6 and VT plants and analyzed. The leaves were cut lengthwise. The leaf half containing the midrib was transversely cut at intervals across the midrib and along the outer edge of the leaves. The leaves were vacuum infiltrated with GUS histochemical assay buffer and incubated at 37° C. until stained regions were visible. Chlorophyll was removed by incubation in 70% ethanol at room temperature. Pieces of stems that included a node and adjacent internodal regions were cut from the bottom, middle and top sections of VT plants. Cross sections of the internodal regions and longitudinal sections that included the node and internodal regions above and below the node were stained. One longitudinal and one cross sectional piece of each stem region analyzed was stained until blue was visible; another set of stem pieces was stained overnight. After staining, the stem pieces were placed in 70% alcohol to remove chlorophyll. Pollen was collected from transgenic per5adh/GUS/nos plants for 2 hr from tassels from which all extruded anthers were removed. Pollen was stained overnight. Kernels were analyzed 20 days post-pollination from crosses done in which the transgenic plant was the male parent and from crosses in which the transgenic plant was the female parent. The kernels were dissected longitudinally through the embryo.

Screening of $R_0$ Plants for Uniform Expression.

To define the spatial and temporal expression patterns of a promoter of interest, the expression pattern of a transgene must not be affected by its chromosomal location. Evidence suggests that transgene expression can be "silenced" non-uniformly in different parts of plants, resulting in spatial and temporal expression patterns that do not represent the true promoter activity in transgenic plants. Gene silencing often occurs stochastically, occurring to different extents in individuals within a population (reviewed by Matzke et al. (1993)). All transformation events were screened for uniform expression among five or six $R_0$ plants for each event (Table 7), thus eliminating transformation events that display silencing of the transgene in a population of this size. GUS expression among $R_0$ plants analyzed for each of three transformation events reported here were statistically indistinguishable.

TABLE 7

Expression of GUS with pDAB 419 in Individual $R_0$ Plants in Three Transformation Events

| TRANSFORMATION EVENTS | | | | | |
|---|---|---|---|---|---|
| 308/419-01[a] | | 419-02 | | 419-16 | |
| Relative Light Units/mg Protein | Standard Deviation[b] | Relative Light Units/mg Protein | Standard Deviation[b] | Relative Light Units/mg Protein | Standard Deviation[b] |
| 24973 | 853 | 5261 | 562 | 1011 | 97 |
| 23811 | 641 | 4537 | 381 | 1039 | 14 |
| 29747 | | 5055 | 573 | 1213 | 9 |
| 24081 | 614 | 5743 | 137 | 942 | 12 |
| 25729 | 199 | 4645 | 315 | 1367 | 57 |
| 27025 | | | | 1282 | 46 |

[a]only one sample was analyzed for some of the 308/419-01 plants
[b]standard deviations were determined from independent analyses of two aliquots of tissue from each plant J. Quantitative Analyses of pDAB419 Maize Plants.

Quantitative analyses of GUS activity was done at two stages of corn development: V6 (whorl stage) and VT (tassel emergence). Entire leaf, stem or root samples were powdered and duplicate aliquots were analyzed. GUS activity was determined relative to either extracted protein concentration or to fresh weight of tissue. The high percent recovery of GUS activity indicates extraction procedure for GUS is efficient (Tables 8 and 9). The 308/419-01 and 419-02 plants are $BC_1$ (crossed consecutively with the same inbred twice) and Ro generations, respectively. The per5adh promoter is expressed in root, stem (VT plants) and leaf tissue (Tables 8 and 9). When normalized to extractable protein, roots express higher levels of GUS than leaves in V6 and VT plants; stem accumulates GUS at levels higher than either leaves or roots in VT plants (Tables 8 and 9). GUS expression normalized to fresh weight of tissue and expression normalized to extractable protein levels follow similar trends of organ-specificity of expression in VT plants, although the relative proportions of expression among the organs are different. In V6 plants, the per5adh promoter expresses GUS at similar levels in leaves and roots based on fresh weight of tissue, but the promoter clearly expresses GUS higher in roots than in leaves when expression is normalized to extractable protein.

TABLE 8

Expression of Per5adh/GUS/nos in V6 Transgenic Plant Organs

| Plant Organ | Relative Light Units/mg Protein | Standard Deviation[a] | Relative Light Units/g Tissue (÷ 1000) | Standard Deviation[a] | Average Percent Extraction Efficiency[b] |
|---|---|---|---|---|---|
| 308/419-02 | | | | | |
| leaves | 5,518 | 155 | 39,687 | 4,231 | 86.8 |
| roots | 15,496 | 2,918 | 33,155 | 7,620 | 91.1 |
| 419-02 | | | | | |
| leaves | 3,256 | 111 | 23,367 | 1,704 | 85.8 |
| roots | 8,871 | 35 | 14,316 | 333 | 89.3 |

[a] standard deviations were determined from independent analyses of two aliquots of tissue from each sample
[b] extraction efficiency was percent recovery of GUS activity in the first two extractions relative to the total GUS activity in all three extractions of the tissues

TABLE 9

Expression of Per5adh/GUS/nos in VT Transgenic Plant Organs

| Plant Organ | Relative Light Units/mg Protein | Standard Deviation[a] | Relative Light Units/g Tissue (÷ 1000) | Standard Deviation[a] | Average Percent Extraction Efficiency[b] |
|---|---|---|---|---|---|
| 308/419-02 | | | | | |
| leaves | 2,915 | 177 | 30,426 | 1,567 | 87.3 |
| stem | 15,701 | 837 | 35,601 | 593 | 85.2 |
| roots | 10,197 | 351 | 15,393 | 310 | 82.8 |
| 419-02 | | | | | |
| leaves | 2,319 | 15 | 18,112 | 1,305 | 86.7 |
| stem | 14,721 | 165 | 32,619 | 747 | 84.0 |
| roots | 3,923 | 734 | 6,473 | 814 | 83.1 |

[a] standard deviations were determined from independent analyses of two aliquots of tissue from each sample
[b] extraction efficiency was percent recovery of GUS activity in the first two extractions relative to the total GUS activity in all three extractions of the tissues The per5adh promoter activity was examined in detail in roots. For these experiments, 308/419-01 plants were grown in 15 gallon pots to improve root quality. Roots at all nodes express GUS, but the GUS activity/mg extractable protein increases in nodes 3–5 relative to expression in nodes 1 and 2 (Table 10).

TABLE 10

Expression of GUS with pDAB 419 in Transgenic Plant Root Nodes

| Root Node | Relative Light Units/mg Protein | Standard Deviation[a] |
|---|---|---|
| node 1 | 5,479 | |
| node 2 | 4,268 | 297.5 |
| node 3 | 6,836 | 47.3 |
| node 4 | 8,148 | 92.6 |
| node 5 | 10,887 | 305.9 |

[a] standard deviations were determined from independent analyses of two aliquots of tissue from each sample; only one sample was available for node 1

K. Histochemical Analyses of pDAB419 Maize Plants.

The per5adh promoter expresses GUS to levels that are detectable in all tissues tested using the histochemical staining procedure of Jefferson (1987) with the exception of kernels (but only when the transgenic plant is used as a pollen donor) and pollen. Roots at all nodes of these transgenic plants express GUS. GUS is expressed over the entire length of the roots with the exception that in at least some roots, the expression drops dramatically at the distal end of the root. The loss of stainable activity in the root ends is not due to technological limitations of the protocol in that roots from transformation events expressing transgenes driven by other promoters express highly in these regions. The stem stains for GUS activity non-uniformly, with the pith showing poor or no staining; the nodes and areas adjacent to the outer edge of the stem stain. Most of the areas that stain correspond to regions rich in vascular tissue. The blade, sheath and the midrib of the leaves express GUS. Kernels do not display any stainable activity in overnight incubations in GUS histochemical staining solution when the kernels are from crosses using the per5adh/GUS/nos plants as the pollen donor. However, when the transgenic plant is used as the maternal parent in the cross, GUS is expressed in the pericarp (seed coat) as well as a discrete area of the embryo.

Expression patterns of maize plants transformed with pDAB419 were similar to the expression patterns observed in transgenic rice. The per5 promoter/adh I intron combination appear to promote a pattern of expression which is constitutive. That is, significant expression is observed in both roots and leaves. This is unexpected as the per 5 gene is natively root-preferentially expressed. This result is consistent with the expression pattern that was observed in rice.

EXAMPLE 11

PerGUS16

PerGUS16 is a plasmid containing 4 kb of per5 promoter, the per5 untranslated leader sequence, the coding sequence for the first five amino acids of per5, the GUS gene, and the nos 3'UTR. The complete sequence of PerGUS16 is given in SEQ ID NO 15. With reference to SEQ ID NO 15, significant features of PerGUS16 are given in Table 11.

TABLE 11

Significant Features of PerGUS 16

| nt (SEQ ID NO 15) | Features |
|---|---|
| 1–6 | SstI site |
| 37–42 | BamHI site |
| 43–48 | SalI site |
| 48–53 | NcoI site |
| 48–4247 | Per5 promoter nt 1–4200 of SEQ ID NO 1 and untranslated leader |
| 4248–4263 | Per5 exon nt 4201–4215 of SEQ ID NO 1 |
| 4264–6068 | β glucuronidase gene (GUS) |
| 6069–6111 | untranslated sequence from pBI221 |
| 6122–2127 | SstI site |
| 6122–6396 | nos 3'UTR |
| 6397–6407 | linker |
| 6402–6407 | HindIII site |
| 6408–9299 | Bluescript ® II SK⁻ |

PerGUS16 is different from pDAB411 in that PerGUS16 includes the coding sequence for the first 5 amino acids of the per5 protein. In addition PerGUS16 contains 4 kB of upstream promoter sequence, whereas pDAB411 only contains 2 kB of sequence. Neither PerGUS16 nor pDAB411 includes an intron in the untranslated leader. PerGUS16 was constructed and tested in a transient maize root expression assay as follows.

A. Construction of PerGUS 16. A 4.0 kB NcoI fragment, containing 4 kB of upstream per5 sequence, the per5 untranslated leader sequence and the coding sequence for the first 5 amino acids of per5, from perGEN1(10.4) was purified from a 1.0% agarose gel using Qiagen kit. This 4.0 kB promoter fragment was ligated into an NcoI site at the translation initation start site of the GUS gene in pGUS-nos12. pGUSnos12 is a plasmid based on Bluescript ® II SK⁻ with an inserted BamHI-HindIII fragment containing the coding region for the GUS gene and the nos 3'UTR. The resultant translation fusion is PerGUS16.

B. Expression Assay. Results of testing PerGUS16 in a transient maize root expression assay are given in Table 14.

EXAMPLE 12

PERGUSPER3

PERGUSPER3 is a plasmid containing 4 kb of per5 promoter, the per5 untranslated leader sequence, the coding sequence for the first five amino acids of per5, the GUS gene, and the per5 3'UTR. The complete sequence of PERGUSPER3 is given in SEQ ID NO 16. With reference to SEQ ID NO 16, critical features of PERGUSPER3 are as follows:

TABLE 12

Significant Features of PERGUSPER3

| nt (SEQ ID NO 16) | Features |
|---|---|
| 1–6 | SstI site |
| 1–42 | Bluescript SK polylinker |
| 37–42 | BamHI site |
| 43–48 | XbaI site |
| 43–53 | synthetic linker |
| 54–59 | NcoI site |
| 54–4253 | Per5 promoter nt 1–4200 SEQ ID NO 1 |
| 4254–4269 | Per 5 exon nt 4201–4215 SEQ ID NO 1 |
| 4264–4269 | NcoI site |
| 4266–6074 | β glucuronidase gene (GUS) |
| 6075–6117 | untranslated sequence from pB 1221 |
| 6135–6140 | XhoI site |
| 6140–6510 | Per5 3'UTR nt 6069–6439 SEQ ID NO 1 |
| 6511–6516 | HindIII site |
| 6517–9408 | Bluescript ® II SK⁻ |

PERGUSPER3 is identical to PerGUS16 except for its 3'UTR. PerGUS16 has the nos and PERGUSPER3 has the per5 3'UTR. Neither PERGUSPER3 nor PerGUS16 has an intron in the untranslated leader. PERGUSPER3 was constructed and tested in a transient maize root assay, in stable transformed rice callus, and in stable transformed rice plants as follows.

A. Construction of PERGUSPER3

1. BSGUSper4. The 3'UTR from the per5 gene was amplified on a 396 bp fragment (corresponding to bp 6069 to 6439 of SEQ ID NO 1 plus 26 bases of synthetic linker sequence) from the plasmid perGEN1(10.4) using Amplitaq polymerase with buffers supplied and synthetic primers, TTATCTCGAGGGCACTGAAGTCGCT-TGATGTGCTGAATT (SEQ ID NO 17) and

GGGGAAGCTTCTCTAGATTTGGATATAT-GCCGTGAACAATTG (SEQ ID NO 18).

The 5' primer added an XhoI restriction site, and the 3' primer included a HindIII site, to facilitate cloning. This fragment contains a canonical AAUAAA poly-A addition signal at position 247 (corresponding to bp 6306 of SEQ ID NO 1). The amplification product was ligated into an XhoI/HindIII of plasmid pDAB356/X [Note: The structure of plasmid pDAB356/X is not directly relevant to the end result of this construction series. It was constructed during an unrelated series, and was chosen because it contained restriction recognition sites for XhoI and HindIII at the 3' end of the GUS coding region. Those skilled in the art will realize that other plasmids can be substituted at this step with equivalent results.] and transformed into DH5α. Ampicillin resistant transformants were screened by colony hybridization using the per5 3'UTR amplification product as a probe.

Three of the resulting transformants hybridized to ³²P radiolabelled 3'UTR amplification product. The plasmid from each of these three transformants was extracted for sequence analysis. Sequence analysis using an Applied Biosystems automated sequencer revealed that a clone designated p3'per26 was free of PCR induced errors. A 2.0 kB BamHI/HindIII fragment from p3'per26 containing the GUS-per5 3'UTR was gel purified as described above and ligated into the BamHI/HindIII cloning site of Bluescript ® II SK⁻. One of the resulting plasmids, designated BSGUSper4, was characterized and selected for subcloning.

2. PERGUSPER3. The 4.0 kB NcoI per5 promoter fragment from perGEN1(10.4) described above was ligated into the NcoI site of BSGUSper4 (the translational initiation of the GUS gene). The resultant clone, PERGUSPER3, contains 4 kB of per5 promoter, the per5 untranslated leader sequence, the first 5 amino acids of per5, the GUS gene, and the per5 3'UTR.

B. Expression Assays. Results of testing PERGUSPER3 in a transient maize root assay are given in Table 14. Results of testing PERGUSPER3 in stable transformed rice callus and rice plants is given in Tables 15.

EXAMPLE 13

5' Deletions of PERGUSPER3

A series of 5' deletions of PERGUSPER3 was assembled to test the effect on expression. Construction of these vectors utilized naturally occurring restrictions sites in the 4.0 kB NcoI promoter region.

A. Construction of SPGP1

SPGP1 is identical to PERGUSPER3 except for the absence of 2 kB of 5' upstream sequence (i.e., bp 25 to 2585 of SEQ ID NO 16 are deleted). SPGP1 was derived from PERGUSPER3 by subcloning the XbaI fragment of PER-GUSPER3 into the XbaI site of Bluescript ® II SK⁻.

B. Construction of HSPGP4.

HSPGP4 is identical to SPGP1 except for the absence of 1 kB of 5' upstream sequence (i.e., bp 25 to 3240 of SEQ ID NO 16 are deleted). This vector was derived from SPSP1 by the deletion of the 1 kB HindIII fragment.

C. Construction of PSPGP1

PSPGP1 is identical to SPGP1 except for the absence of 1.9 kB of PstI sequence (i.e., bp 25 to 4139 of SEQ ID NO 16 are deleted). PSPGP1 only had 109 bases of 5' sequence which includes the TATA box.

D. Expression Assay. Results of testing SPGP1, HSPGP4 and PSPGP1 in a transient maize root expression assay are given in Table 14.

EXAMPLE 14

Transient Root Expression Assay

Transient assays have been successfully used for studying gene expression in plants, especially where an efficient stable transformation system is not available (i.e., maize, wheat). In protoplasts, these assays have been used to study the expression of regulatory elements with relatively simple expression patterns. For example, constitutive promoters, including the CaMV 35S, have been extensively studied in maize protoplasts. Luehrsen and Walbot (1991). However, it was believed that a root preferential promoter, such as per5, would be unlikely to function normally in protoplasts, particularly those derived from tissue culture. Therefore, a system to study expression in intact root tissue was desirable. Particle bombardment of root tissue would enable transient expression analysis and reduce the need for production of stable transgenics.

A. Helium Blasting into Roots. Captan™-treated seed of CQ806 and OQ403 were soaked for 45 min., rinsed 3 times in sterile distilled water, and germinated in sterile petri dishes (100×25 mm) containing Whatman #1 filter paper moistened with sterile milli Q water for about 4–7 days. Approximately 1 cm size root tips were excised and arranged (6 per target) in 'blasting' medium (#4 with 2% agar). The 'blasting medium' consisted of N6 basal salts and vitamins (Chu, 1978), Fe-EDTA, 20 g/L sucrose, 690 mg/L L-proline, 100 mg/L enzymatic casein hydrolysate (ECH), 1 mg/L 2,4-dichlorophenoxyacetic acid (2,4-D), and 20 g/L agar. The roots were covered with a 204 micron screen prior to blasting. Each target was blasted once at 1,500–2,000 psi using two times dilution of gold/DNA solution. The gold particles (Biorad 1.0 micron) were coated with DNA (different plasmids as mentioned in the text) as described in Example 10B. Different blasting parameters, i.e., 1) different helium pressures (500, 1,000, 1,500, and 2,000 psi), 2) number of blastings per target (1–4 blastings per target), 3) concentration of gold/DNA (1–4 times dilutions of gold/DNA solution), 4) particle size (Aldrich 1.5–3.0 micron vs. Biorad 1.0 micron gold particles), and 5) high osmoticum treatment (0.2M mannitol and 0.2M sorbitol treatment 4 h prior to and 16–18 h after blasting) were tested. Following blasting, roots were transferred to 15Ag10-2D medium and incubated in the dark at 27° C. The 15Ag10-2D medium differed from #4 medium in that it contained 2.9 g/L L-proline, 10 mg/L silver nitrate, 2 mg/L 2,4-D, and 2.5 g/L Gelite.

B. Histochemical GUS Assay. After 18–24 hrs, the blasted roots were assayed for transient GUS expression according to Jefferson (1987). Roots were placed in 24-well microtitre plates (Corning, New York, N.Y.) containing 500 µL of assay buffer per well (six per well). The assay buffer consisted of 0.1 M sodium phosphate (pH 8.0), 0.5 mM potassium ferricyanide, 0.5 mM potassium ferrocyanide, 10 M sodium EDTA, 1.9 mM 5-bromo-4-chloro-3-indolyl-beta-D-glucuronide, and 0.06% triton X-100. The plates were incubated in the dark for 1–2 days at 37° C. before observations of GUS expression under a microscope.

C. Optimization of DNA Delivery into Roots. Transient expression increased with increased helium pressure with highest levels observed at 1,500–2,000 psi. High osmoticum treatment prior to blasting did not enhance GUS expression. Also, increasing the number of blastings per target did not result in increased expression. One blasting per target yielded highest expression in roots of both OQ403 and CQ806. In addition, two times dilution of gold/DNA solution and use of the Biorad 1.0 micron particles were found to be most suited for obtaining consistently high levels of expression. Based on these results, a set of conditions were established for blasting into roots. With these conditions, 60–100% of the blasted roots expressed GUS with an average number of ca. 50 GUS expression units per target using pDAB418 (Ub1-GUS-nos).

D. Transient Expression of Different per5 Constructs in Roots. Transient GUS expression of different per5 constructs was tested in roots following helium blasting using the conditions described above. The results from ten different experiments are summarized in Table 14.

TABLE 14

Transient expression of different per5 constructs in roots.

| Plasmid | Description | # GEUs* | (N)‡ | Rating |
|---|---|---|---|---|
| PerGUS16 | 4.5 kB per5, first 5 aa of per5 protein-GUS-nos | 3.4 | (24) | ++ |
| PERGUSPER3 | 4.5 kB per5, first 5 aa of per5 protein-GUS-per5 | 10.0 | (24) | ++++ |
| SPGP1 | 2.0 kB per5, first 5 aa of per5 protein-GUS-per5 | 10.7 | (24) | ++++ |

TABLE 14-continued

Transient expression of different per5 constructs in roots.

| Plasmid Description | | # GEUs* | (N)‡ | Rating |
|---|---|---|---|---|
| HSPGP | 1.0 kB per5, first 5 aa of per5 protein-GUS-per5 | 5.8 | (15) | +++ |
| PSPGP | 0.1 kB per5, first 5 aa of per5 protein-GUS-per5 | 10.8 | (16) | ++++ |
| pDAB411 | 2.0 kB per5-GUS-nos | 1.1 | (5) | + |
| pDAB419 | 2.0 kB per5, Adh1 intron1-GUS-nos | 6.7 | (3) | +++ |

*GUS expression units (number of blue spots observed) per target
‡N = # of targets blasted pDAB411, the construct containing 2.0 kB per5, expressed at very low levels. With PerGUS 16 containing 4.0 kB per5 and a fusion including the first five amino acids of the per5 protein, the expression was 3-fold higher than that of pDAB411. Further, PerGUSper3 consisting of per5 with the 3'UTR showed a further 3-fold increase over PerGUS16 demonstrating that 3' end is also important for regulation of expression. Although SPGP1 contained 2.0 kB of per5, no difference was observed between the expression of SPGP1 and PerGUSper3. With additional deletion in the 5' region of per5 in HSPGP (which contains 1.0 kB of per5), expression was decreased over that of SPGP1 and PerGUSper3. However, relatively high levels of expression were observed with PSPGP containing only 0.1 kB region of per5.

Probably all of the promoter elements which were necessary for maximal root specific expression are present in the first 1 kB of 5' sequence. However, elements which may suppress expression in other tissues may not be present in this 1 kB sequence. Similar observations have been made with the 5' upstream sequences of the Sus4 gene from potato which contains a negative element that suppresses expression in stems and leaves. Fu et al. (1995). Transient assays in other tissues would be necessary to obtain this information from the per5 constructs. Expression from PSPGP, which contained only 100 bases 5' sequence, probably acts as a basal promoter and, therefore, would not be expected to contain the elements necessary for root specific expression nor enhancer elements necessary for maximal activity of the promoter. Expression from this construct in stable plants would be expected to be constitutive.

A translational fusion of the per5 gene which included the per5 5' untranslated leader (UTL) and the first 5 amino acids of the per5 gene fused to the uidA was included in PerGUS16, PERGUSPER3, SPGP1, HSPGP, and PSPGP constructs. The ability of these constructs to express GUS, demonstrated that this UTL sequence was capable of promoting translation and therefore can be used to express commercially important transgenes.

The most obvious improvement in expression was observed from the addition of the per5 3'UTR in place of the nos sequence. 3'UTR's are known to contain sequences which affect gene expression by altering message stability (Sullivan and Green (1993)) or influencing translation (Jackson and Standart (1990)). Examples include polyadenylation signals (Rothnie et al. (1994)) and destabilizing elements (Gallie et al. (1989)). However, the per5 and nos 3'UTR's cannot be distinguished by the presence or absence of these sequences. Both UTR's contain a canonical AAUAAA poly-A addition signal. Neither sequence appears to contain any of the published destabilizing elements. An obvious difference between the two UTR's is the length; the longer per5 UTR may confer greater stability of the message.

EXAMPLE 15

Rice Transformation of PERGUSPER3

Transgenic Production and Histochemical GUS Assay

To study the expression of PerGUSPer3 in transgenic rice, a total of 35 independent transgenic lines were produced. Out of these, plants of 9 lines (354/PERGUSPER3-03,20, 21,23,24,27,28,30, and 34) displayed GUS expression in roots. Although GUS expression was variable from line to line, a few lines showed very intense expression in roots. Histochemical GUS analysis of different tissues following vacuum infiltration showed GUS expression in cut portions of leaves, glumes, anthers, pollen and embryo. No expression was seen in endosperm. All of these results suggest that per5 expresses in a constitutive manner in rice.

Rice plants from six PERGUSPER3 Ro lines were characterized by Southern analysis. The rice DNA was also cut with the restriction enzyme XbaI which should result in a 4.2 kb fragment when hybridized to the GUS probe. All of the six lines contain the gene construct. A moderately complex integration event was detected in one of the six lines containing an intact copy of the gene construct. The remaining five lines all had complex integration events with as many as nine hybridization products. A summary of the genetic analysis is located in Table 15.

TABLE 15

Assay of Transformed Rice Plants

| Plant | Presence of the Intact Gene Construct | Number of Hybridization Products | Gus Histochemical Results | Relative Light Units per ug of protein - Root | Relative Light Units per ug of protein - Leaf |
|---|---|---|---|---|---|
| 354/PGP3-20 | Yes | 5 | Positive | 13,129 | 26,220 |
| 354/PGP3-21 | Yes | 9 | Positive | 1,579 | 623 |
| 354/PGP3-22 | n.d. | — | Negative | 5 | 11 |

TABLE 15-continued

Assay of Transformed Rice Plants

| Plant | Presence of the Intact Gene Construct | Number of Hybridization Products | Gus Histochemical Results | Relative Light Units per ug of protein - Root | Relative Light Units per ug of protein - Leaf |
|---|---|---|---|---|---|
| 354/PGP3-23 | Yes | 4 | Positive | 61 | 20 |
| 354/PGP3-24 | Yes | 3 | Positive | 1,484 | 1,398 |
| 354/PGP3-27 | Yes | 6 | Positive | 115 | 12 |
| 354/PGP3-28 | Yes | 5 | Positive | 338 | 222 | n.d. — not determined

Both longitudinal and transverse root sections prepared from transgenic rice seedlings showed cells with GUS expression (blue color) and cells interpreted to lack GUS expression (red color resulting from the counterstain). Longitudinal section of a primary root showed GUS expression present in all cells except for those present in the root cap, meristematic zone, and a portion of the cell elongation zone. This pattern of expression was confirmed for secondary root formation in a transverse section of root tissue. Cross section of a primary root, prepared from within the zones of cell elongation and differentiation, showed most cells expressing GUS. Very intense GUS expression (dark blue) was observed in the exodermis or outer cortex of the root sample. GUS expression was noted as slight to absent in the epidermal layer even though root hairs were observed macroscopically to be blue. Both vascular and cortical tissues showed moderate expression. Based on the consistent staining patterns obtained from free hand tissue sections, cells in the vascular and cortical tissues genuinely expressed the GUS protein rather than appear as artifacts with the diffusion of histochemical stain from the exodermis.

Analysis of variance showed that sample to sample variation within each of the independent events was not significant. However, most of the variation was associated among the different events. Based on the GUS quantitative data, only event 354/PERGUSPER3–20 was shown to be highly significant different (p<0.001) from zero (Table 15) even though five other events were shown to be histochemically GUS positive.

The maize per5 5' region in combination with the 3' untranslated sequences promoted high-level expression of the introduced β-glucuronidase gene in young transgenic rice plants. Functional activity was observed in both roots and leaves. Quantitative data indicated that there was considerable variability of expression between the different events. This variability is most likely a result of a combination of factors including position effects of the integrated transgene, differences in copy number of the insertion products, and rearrangements of the insertion events. All of these variables have the potential to effect expression levels and have been documented in most transgenic studies.

Despite high degree of variability in the expression levels, the expression pattern of PerGUSPer3 in different transformation events was consistent. Slight to very intense expression was evident in the entire primary and secondary roots except in the root tips. Histological analysis showed very intense expression in the outer cortex and moderate expression in cortex and vascular tissues. Such pattern and level of expression observed appears to be very suitable for expression of genes to control root pests (i.e., root weevil). In addition, consistent with expression in roots, high levels of expression was also observed in stem and leaf tissue (quantitative data) thus providing opportunity for controlling other insects (i.e., stem borer). These data demonstrate that the per5 promoter, in the absence of an intron, drives constitutive expression of transgenes in rice.

EXAMPLE 16

Maize Transformation of PERGUSPER3

Establishment of typeII callus targets and helium blasting conditions were that same as described in Example 10. A total of 82 independent transgenic colonies of maize were produced. Of these, 55 lines were subjected to Southern analysis as described in Example 15. Twenty-nine lines were found to be Southern positive and contained an intact hybridization product of the GUS gene. Following GUS histochemical assay, callus of about 72 lines showed no expression. Also, roots and leaves of different Southern-positive lines displayed no GUS expression when callus was regenerated on the 'regeneration' medium. This data supported the observation that sequences other than the 5' promoter region and the 3'UTR were critical for expression in corn.

EXAMPLE 17

Plasmid PIGP/367

Plasmid PIGP/367 contains the per5 promoter, the per5 untranslated leader modified to include the per5 intron 1, the GUS gene, and the per5 3'UTR. The complete sequence for PIGP/367 is given in SEQ ID NO 19. With reference to SEQ ID NO 19, critical features of PIGP/367 are given in Table 16.

TABLE 16

Significant Features of PIGP/367

| nt (SEQ ID NO 19) | Features |
|---|---|
| 1–40 | synthetic polylinker |
| 41–75 | pCR ™ 2.1 polylinker |
| 81–1741 | Per5 promoter nt 2532–4192 SEQ ID NO 1 |
| 1742–1747 | BglII/BamHI junction |
| 1748–1763 | Per 5 exon1 nt 4410–4425 SEQ ID NO 1 |
| 1764–2396 | Per 5 intron nt 4426–5058 SEQ IDNO 1 |
| 2397–2405 | Per 5 exon2 nt 5059–5067 SEQ ID NO 1 |
| 2406–2411 | NcoI site |
| 2408–4215 | β glucuronidase gene (GUS) |
| 4217–4264 | sequence from pB1221 |
| 4280–4652 | Per 5 3' UTR nt 6067–6439 SEQ ID NO 1 |
| 4653–4869 | synthetic linker |
| 4870–5121 | CaMV DNA nt 7093–7344 |
| 5122–5129 | linker |

TABLE 16-continued

Significant Features of PIGP/367

| nt (SEQ ID NO 19) | Features |
| --- | --- |
| 5130–5476 | CaMV DNA nt 7093–7439 |
| 5477–5496 | linker |
| 5497–5606 | synthetic MSV leader(MSV nt 167–186, 188–277) |
| 5608–5613 | BglI/BclI junction |
| 5608–5698 | Adh1.S nt 119–209 |
| 5699–5820 | Adh1.S nt 555–672 plus 4 bases linker sequence |
| 5821–5827 | BamHI/BglII junction |
| 5828–5864 | MSV nt 278–317 |
| 5863–5868 | NcoI site |
| 5865–6419 | phosphinothricin acetyl transferase gene (Basta ™ resistance selectable marker) |
| 6420–6699 | nos 3' UTR |
| 6700–9335 | pUC19 sequences |

Because intron flanking sequences (exon DNA) have been shown to be important in the processing of the intron (Luehrsen and Walbot (1991)), 16 bases of flanking exon DNA were included the fusion within the per5 untranslated leader.

Construction of PIGP/367.

The promoter from the per5 gene was amplified using the forward primer GGGGGATCC TCTAGACAATGATATACATAGATAAAAACC (SEQ ID NO 20) which introduces a BamHI (GGATCC) site 5' of the promoter to facilitate cloning. The reverse primer within the untranslated leader of the per5 gene was GGGAGATCT CCTTCGCTGTACTATGTTATAAGAGAAGAG (SEQ ID NO 21) and introduced a BglII (AGATCT) restriction site 3'. Sequences homologous to the promoter are underlined. The primers were synthesized on a 394 DNA/RNA Synthesizer (Applied Biosystems, Foster City, Calif.). Amplification reactions were completed with the Expand™ Long Template PCR System (Boehringer Mannheim, Indianapolis, Ind.). Plasmid perGen10.44, which contains 10.1 kb of the maize peroxidase gene and untranslated and non-transcribed sequences, was used as the template DNA. Amplifications were cycled with a 56° C. annealing temperature. Amplification products were separated and visualized by 1.0% agarose gel electrophoresis. Resulting amplification products were excised from the agarose and the DNA was purified using Qiaex II (Qiagen, Hilden, Germany). The products were ligated into pCR2.1 using the Original TA Cloning Kit (Invitogen Corporation, San Diego, Calif.). Recombinant plasmids were selected on Luria agar (Gibco, Bethesda, Md.) containing 75 mg/liter ampicillin (Sigma, St Louis, Mo.) and 40 ml/plate of a 40 mg/ml stock of X-gal (Boehringer Mannheim, Indianapolis, Ind.). Plasmid DNAs were purified using Wizard™ plus Miniprep DNA Purification System (Promega, Madison, Wis.). DNA was analyzed and subcloned with restriction endonucleases and T4 DNA ligase from Bethesda Research Laboratories (Bethesda, Md.). The resultant per5 promoter clone was named p121-20.

Intron 1 and 25 bases of flanking exon DNA from the per5 gene was amplified using the forward primer GGGGGATCC TGACTGCTTTGTCAAGGTTCAATTCTGCTT(SEQ ID NO 22) which introduced a BamHI (GGATCC) site 5' the exon/intron DNA, and the reverse primer, GGGCCATGG ATCGCAGCCCTACACATGTAACAGTGTTGT(SEQ ID NO 23), which introduced an NcoI (CCATGG) site 3' to facilitate fusion at the ATG start codon of the GUS gene. Sequences homologous to the per5 sequence are underlined. Amplification and cloning was completed as described above with the resultant intron clone named p122-2. The intron was then excised from p122-2 on the BamHI/NcoI fragment and introduced 5' to the GUS gene/per 5 3' untranslated region in BSGUSper4. Ligations were transformed into DH5α (Laboratory, Bethesda, Md.) and DNA was extracted as described above. Sequence across the junction was verified using Dye Terminator Cycle Sequencing Ready Reaction Kit (Perkin Elmer, Foster City, Calif.) and 373A DNA Sequencer (Applied Biosystems, Foster City, Calif.). Computer analysis of the sequences was facilitated by Sequencher™ 3.0 (Gene Codes Corporation, Ann Arbor, Mich.). The intermediate, p128-1, was then digested with BamHI and ligated to the purified promoter BglII/BamHI fragment from p121-20. To generate a final construct containing the selectable marker gene for Basta™ resistance, the per5 promoter/per5 intron/GUS gene/per5 3'UTR were excised from PIPG147-2 on a PvuII/NotI fragment and introduced into a PmeI/NotI site of pDAB367. pDAB367, which contains the gene for Basta™ resistance, is described in Example 27. The final construct was designated pPIGP/367.

EXAMPLE 18

Transformation of Maize with pPIGP/367

A. Establishment of Type II Callus Targets. The materials and methods used were the same as in Example 10.

B. Helium Blasting and Selection. The materials and methods used were the same as in Example 10. Thirty three Basta™ resistant lines, designated pPIGP-01 thru pPIGP-33, were obtained.

C. Plant Regeneration. The materials and methods used were the same as in Example 8. Plantlets were regenerated from five of the PIGP/367 transgenic lines (PIGP/367-01, PIGP/367-06, PIGP/367-19, PIGP/367-32 and PIGP/367-33).

D. GUS Histochemical Staining. Tissue from plantlets of pPIGP-01 were histochemically evaluated as described in Example 10. The plantlets showed good GUS expression in the roots except for the root cap where no expression was observed. No expression was observed in the leaves of these young plants.

F. Protein Extraction and measurement of GUS. Leaf and root tissue was collected and analysis for GUS expression completed from four of the PIGP/367 transgenic lines (PIGP/367-06, PIGP/367-19, PIGP/367-32 and PIGP/367-33) which showed positive GUS histochemical expression. An untransformed plant at the same stage of development, CS405, served as a negative control. The 6th leaf and cleaned roots (roots were cleaned under cold running tap water and rinsed with distilled water) were collected from 4–5 $R_0$ plants plants within transgenic lines. The samples were either stored at −70° C. or powdered using liquid nitrogen. Fifty mL tubes, chilled on dry ice, were filled to 10 mL mark with powdered samples. Protein from each sample was extracted in duplicate. Four volumes/weight of extraction buffer (Extraction buffer is 1% polyvinylpolypyrrolidone (hydrated in the solution for at least one hour), 20% glycerol, 0.7 $\mu$L/mL β-mercaptoethanol, 50 mM NaPO; pH 7.0, 10 mM EDTA, 0.1% Triton X-100, 0.1% sarcosyl, 10 mM β-mercaptoethanol) was added to each sample. Samples were ground using Ultra-Turrax T 25 (IKA-Works INC, Staufen I. Br., W. Germany) and kept on ice. Samples were spun at 3000 rpm at 4° C. for five minutes. Ten $\mu$L/mL of protease inhibitor (50 $\mu$g/mL antipain, 50 ug/mL leupeptin, 0.1 mM chymostain, 5 $\mu$g/mL pepstatin, 0.24 $\mu$g/mL pefabloc (Boehringer Mannheim, Indianapolis, Ind.)) was added to withdrawn sample supernatant. The samples were then spun at 4° C. for 10 minutes at 13,000 rpm. The supernatants were withdrawn and stored at −70° C. Protein concentration was measured on a UV-Visible Spectrophotometer (Shimadzu, Kyoto, Japan). Five μL of sample was added to 2.5 mL of protein dye reagent (Sigma Diagnostics, St. Louis, Mo.) and 100 μL of sterile water. A range of standards was made from protein standard solution (Sigma Diagnostics, St. Louis, Mo.).

GUS activity was measured using a GUS-Light ™ Kit (Tropix Inc., Bedford, Mass.) in replicate samples of the duplicate extractions. Five μL samples of undiluted extract or of extract diluted so that the luminescence was within the range measured by the luminometer was added to 195 μL of the GUS-™ Diluent Solution. After 1 hr incubation, at 28° C. in the dark, luminescence was measured using a Bio Orbit 1251 luminometer, equipped with a Bio Orbit 1291 injector, after injection of 300 μL of GUS-Light ™ Accelerator. Luminescence was integrated for 5 sec after a 5 sec delay. The standards used were extraction buffer, non-transformed tissue stock and GUS-Light ™ Gus Standard. The results are summarized in Table 17 and showed high levels of expression in the roots, but low to no significant expression in the leaves.

TABLE 17

Expression of GUS with PIGP/367 in Plants from Four Transformation Events

| Line | Leaf (RLU/μg protein) | Root (RLU/μg protein) |
|---|---|---|
| PIGP/367-06 | 734 | 5735 |
| PIGP/367-19 | 49 | 5745 |
| PIGP/367-32 | 8 | 349 |
| PIGP/367-33 | 72 | 1586 |
| CS405 | 1 | 13 |

G. Summary of Expression Results.

In the previous examples herein, no significant expression was observed in any maize tissue (although it was in rice) in the absence of an intron downstream from the per5 promoter. When the Adh1 intron was fused to the promoter (Examples 8, 10), expression in maize was observed. The Adh1 intron I was not capable of restoring the root-preferential expression in maize that is characteristic of the native per5 gene. Root-preferential expression was only achieved when the promoter was placed in combination with the per5 intron. This is the first demonstration of an intron directing tissue specific or tissue-preferential expression in transgenic plants. Xu et al. (1994) have reported preliminary studies on the promoter of another root-preferential gene, the triosephosphate isomerase gene from rice. They found that an intron is required for expression from this promoter in rice protoplasts, but the effects of the intron on gene expression in mature tissues has not been described.

The mechanism for enhancement by an intron is not well understood. The effect appears to be post-transcriptional (rather than promoter-like effects on the initiation of transcription) because the enhancements are only seen when the intron is present in the region of DNA that is transcribed (Callis, 1987). Introns could play a role in stabilizing the pre-mRNA in the nucleus, or in directing subsequent processing (Luehrsen and Walbot, 1991). The root-preferential expression of the per5 promoter-intron combination could be explained by requiring an intron for processing, and a limited tissue distribution of other factor(s) necessary for correct processing.

EXAMPLE 19

Plasmid p188-1

Plasmid p188-1 is a clone of the per5 3'UTR. The per5 3'UTR was amplified on Plasmid Xba4, which contains the 4.1 kb XbaI fragment from nt 2532 to 6438 of SEQ ID NO 1, using the forward primer, AAA GAG CTC TGA GGG CAC TGA AGT CGC TTGATG TGC(SEQ ID NO 24), which introduced a SstI site on the 5' end, and the reverse primer, GGG GAA TTC TTG GAT ATA TGC CGT GAA CAA TTG TTA TGT TAC(SEQ ID NO 25), which introduced an EcoRI site on the 3' end of a 366 bp segment of per5 3'UTR (corresponding to nt 6066 to 6431 of SEQ ID NO 1). Sequences homologous to the promoter are underlined. The primers were synthesized on a 394 DNA/RNA Synthesizer (Applied Biosystems, Foster City, Calif.). Amplification reactions were completed with the Expand™ Long Template PCR System (Boehringer Mannheim, Indianapolis, Ind.). Plasmid Xba amplifications were cycled with a 56° C. annealing temperature. Amplification products were separated and visualized by 1.0% agarose gel electrophoresis. Resulting amplification products were excised from the agarose and the DNA was purified using Qiaex II (Qiagen, Hilden, Germany). The products were ligated into pCR2.1 from the Original TA Cloning Kit (Invitrogen Corporation, San Diego, Calif.).

Recombinant plasmids were selected on Luria agar (Gibco, Bethesda, Md.) containing 75 mg/liter ampicillin (Sigma, St Louis, Mo.) and 40 ml/plate of a 40 mg/ml stock of X-gal (Boehringer Mannheim, Indianapolis, Ind.). Plasmid DNAs were purified using Wizard™ plus Miniprep DNA Purification System (Promega, Madison, Wis.). DNA was analyzed and subcloned with restriction endonucleases and T4 DNA ligase from Bethesda Research Laboratories (Bethesda, Md.). The resultant per5 3'UTR clone was named p188-1.

EXAMPLE 20 pTGP190-1

Plasmid pTGP190-1 is a 5887 bp plasmid comprising a gene cassette in which the following components are operably joined: the 35T promoter, the GUS gene, and the per5 3'UTR. The complete sequence of pTGP190-1 is given in SEQ ID NO 26. With reference to SEQ ID NO 26, important features of pTGP190-1 include:

TABLE 18

Significant Features of pTGP 190-1

| nt (SEQ ID NO 26) | Features |
|---|---|
| 12–17 | PstI site |
| 18–30 | linker |
| 31–282 | CaMV MCASTRAS nt 7093–7344 |
| 283–290 | linker |
| 291–637 | CaMV DNA MCASTRAS 7093–7439 |
| 638–657 | linker |
| 650–655 | BamHI site |
| 651–1024 | 374 bp BamHI/NcoI fragment containing MSV leader and Adh1 intron |
| 658–677 | MSV nt 167–186 |
| 678–767 | MSV nt 188–277 |
| 769–774 | BglII/BclI junction |
| 769–978 | Adh1.S intron with deletion described in Example 24 |
| 979–988 | linker |
| 982–987 | BamHI/BglII junction |
| 989–1028 | MSV nt 278–317 |
| 1024–1029 | NcoI site |
| 1026–2834 | β glucuronidase coding sequence (GUS) |
| 2835–2890 | sequence from pKA882 |
| 2890–2895 | SstI site |

TABLE 18-continued

Significant Features of pTGP 190-1

| nt (SEQ ID NO 26) | Features |
|---|---|
| 2896–3261 | Per 5 3'UTR nt 6066 to 6431 of SEQ ID NO 1 |
| 3262–3267 | EcoRI site |
| 3268–5897 | pUC19 sequences |

Construction of pTGP190-1.

The per5 3'UTR was excised from p188-1 (Example 19) using the SstI/EcoRI sites and purified from an agarose gel as described above. This fragment was ligated to the SstI/EcoRI A fragment of pDAB305. (pDAB305 is described in detail in Example 24.) Plasmid pDAB305 is a 5800 bp plasmid that contains a heterologous promoter which is known as 35T. Construction of the 35T promoter is described in detail in Example 24. Basically this construct contains tandem copies of the Cauliflower Mosaic Virus 35S promoter (35S), a deleted version of the Adh1 intron 1, and the untranslated leader from the Maize Streak Mosaic Virus (MSV) Coat Protein fused to the β-glucuronidase gene, which is then followed by the nos 3'UTR.) The SstI/EcoRI A fragment of pDAB305 deletes the nos 3'UTR. Ligations were transformed into DH5α (Bethesda Research Laboratory, Bethesda, Md.) and DNA was extracted as described above. Sequence across the promoter/GUS junction was verified using Dye Terminator Cycle Sequencing Ready Reaction Kit (Perkin Ehner, Foster City, Calif.) and 373A DNA Sequencer (Applied Biosystems, Foster City, Calif.). Computer analysis of the sequences was facilitated by Sequencher™ 3.0 (Gene Codes Corporation, Ann Arbor, Mich.). Plasmid pTGP190-1 is identical to pDAB305 except for the substitution of the per5 3'UTR for the nos 3'UTR following the GUS gene.

EXAMPLE 21

UGP232-4

Plasmid UGP232-4 is similar to pTGP190-1, but contains the ubiquitin 1 (ubi) promoter and intron I from maize in place of the 35T promoter. The ubi promoter was excised on a HindIII/NcoI fragment from pDAB1538 (described in Example 29) and ligated to the HindIII/NcoI A fragment of pTGP190-1 to derive UGP232-4. The complete sequence for UGP232-4 is given in SEQ ID NO 27. With reference to SEQ ID NO 27, important features of UGP232-4 are given in Table 19.

TABLE 19

Significant Features of UGP232-4

| nt (SEQ ID NO 27) | Features |
|---|---|
| 1–5 | HindIII site |
| 1–14 | pUC19 polylinker |
| 15–993 | ubiquitin promoter from maize |
| 994–2007 | ubiquitin intron |
| 2008–2026 | Synthetic polylinker from previous constructs (KpnI, SmaI and SalI) |
| 2025–2030 | NcoI site |
| 2027–3835 | β glucuronidase coding sequence (GUS) |
| 3836–3890 | sequence from pKA882 |
| 3891–3896 | SstI site |
| 3897–4262 | Per 5 3'UTR nt 6066 to 6431 of SEQ ID NO 1 |

TABLE 19-continued

Significant Features of UGP232-4

| nt (SEQ ID NO 27) | Features |
|---|---|
| 4263–4268 | EcoRI site |
| 4269–6898 | pUC19 sequence | pUGN81-3 was used as the Ubiquitin/GUS/nos control plasmid.

EXAMPLE 22

Quantitative Transient Assays of Maize Callus Bombarded with pTGP191-1 or UGP232-4

A. Preparation of DNA for Transient Testing. Each of the test constructs, in addition to pDAB305 (described in Example 24), was co-precipitated onto gold particles with pDeLux (described in Example 26) according to the following protocol. Equal molar amounts of the GUS constructs were used. A total of 140 μg of DNA, 70 μg of pDeLux plus 70 μg of test DNA and Bluescript ® II SK⁻DNA (when necessary), was diluted in sterile water to a volume of 300 μL. The DNA and water were added to 60 mg of surface-sterilized 1.0 μm spherical gold particles (Bio-Rad Laboratories, Hercules, Calif.). The mixture was vortexed briefly (approximately 15 seconds) before adding 74 μL of 2.5 M calcium chloride and 30 μL of 0.1 M spermidine (free base). After vortexing for 30 seconds, the DNA and gold were allowed to precipitate from solution. The supernatant was removed and 1 mL of ethanol was added. The DNA/gold mixture was diluted 1:8 before use for transformation.

B. Transient Testing in Maize Callus. Regenerable (Type II) maize callus was pretreated on osmotic medium (N6 salts and vitamins (Chu (1978)), 1 mg/L 2,4-dichlorophenoxyacetic acid, 0.2 M sorbitol, 0.2 M mannitol, 7 g/L Gelrite, pH 5.8) for approximately 16 hours. Afterward, it was placed onto 60×20 mm plates of osmotic medium solidified with 2% agar for helium blasting. Cages of 104 μm mesh screen covered each "target" (500–600 mg of callus) to prevent splattering and loss of tissue. Targets were individually blasted with DNA/gold mixture using the helium blasting device described in Example 10. Under a vacuum of 650 mm Hg, at a shooting distance of 10 cm and pressure of 1500 psi, DNA/gold mixture was accelerated toward each target four times, delivering 20 μL per shot. The targets were rotated 180° after each blast. The tissue was also mixed halfway through the blasting procedure to expose unblasted callus. Upon completion of blasting, the targets were again placed onto the original osmotic medium for overnight incubation at 26° C. in the dark.

Four Type II callus cell lines were selected for each experiment. Two targets from each line were used per treatment group. Also, two nontransformed controls (NTC) were included within each experiment, composed of tissue pooled from all four lines. These controls were transferred to osmotic and blasting media according to the protocol above, but were not subjected to helium blasting.

C. GUS Quantitative Analysis. Approximately 20 hours after blasting, 200–400 mg of each target was transferred to a 1.5 mL sample tube (Kontes, Vineland, N.J.). For extraction of proteins, callus was homogenized using a stainless steel Kontes Pellet Pestle powered by a 0.35 amp, 40 Watt motor (Model 102, Rae Corporation, McHenry, Ill.), at a setting of "90". Cell Culture Lysis Reagent from a Luciferase Assay kit (Promega, Madison, Wis.) served as the extraction buffer. Protease inhibitors, phenylmethylsulfonyl fluoride (PMSF) and leupeptin hemisulfate salt, were added to the lysis buffer at the concentrations of 1 mM and 50 µM, respectively. Before grinding, 0.5 µL of lysis buffer per mg tissue was added to the sample tube. The callus was homogenized in four 25-second intervals with a 10-second incubation on ice following each period of grinding. Afterward, 1.0 µL of lysis buffer per mg tissue was added to the sample which was maintained on ice until all sample grinding was completed. The samples were then centrifuged twice at 5° C. for 7 minutes at full speed (Eppendorf Centrifuge Model 5415). After the first spin, the supernatant from each tube was removed and the pellet was discarded. Callus extracts (supernatants) were also collected after the second spin and maintained on ice for GUS and Luciferase (LUC) analyses.

From the LUC Assay kit, LUC Assay Buffer was prepared according to the manufacturer's instructions by reconstituting lyophilized luciferin substrate. This buffer was warmed to room temperature and loaded into the dispensing pump of an automatic luminescence photometer (Model 1251 Luminometer and Model 1291 Dispenser, Bio-Orbit, Finland). Each sample was tested in triplicate by adding 20 µL of extract to three polypropylene luminometer vials (Wallac, Gaithersburg, Md.). Per vial, 100 µL of assay buffer was dispensed, and luminescence was detected over a 45-second integration period. "Blank reactions", including 20 µL of extraction buffer rather than callus extract, were also measured within each experiment to determine the extent of background readings of the luminometer.

For analysis of GUS activity, a GUS-Light™ assay kit (Tropix, Bedford, Mass.) was used. Again, each sample was tested in triplicate, using 20 µL of extract per luminometer vial. GUS-Light™ Reaction Buffer was prepared from the assay kit by diluting liquid Glucuron™ substrate according to the manufacturer's instructions. This buffer was warmed to room temperature and added in 180 µL aliquots to each luminometer vial at 7-second intervals. After a one hour incubation at room temperature, 300 µL of GUS-Light™ Light Emission Accelerator Buffer was added and luminescence was detected over a 5-second integration period. "Blank reactions" were also included in the GUS assay, using 20 µL of extraction buffer rather than callus extract.

GUS and LUC results were reported in relative light units (RLU). Both "blank" and NTC readings were subtracted from sample RLU levels. For comparison of one construct to another, GUS readings were normalized to LUC data by calculating GUS/LUC ratios for each sample tested. The ratios for all samples within a treatment group were then averaged and the means were subjected to a T-test for determination of statistical significance. Within each experiment, results were reported as a percent of pDAB305 expression.

Transient bombardment of Type II callus for each of the constructs was completed as described above. By including pDAB305 as a standard in each experiment and reporting results as a percent of the standard, data from numerous experiments could be meaningfully compared. Table 20. lists results from three experiments testing the nos versus the per5 3'UTRs using two promoters. With either the 35T or Ubi1 promoter, the per5 3'UTR resulted in higher transient GUS expression than the nos 3' end constructs. pUGN223-3 is a plasmid that contains a fusion of the maize ubiquitin promoter and ubiquitin intron 1 to the GUS gene similar to pUGP232-4. However, pUGN223-3 has the nos 5 3'UTR instead of the per 3'UTR. pUGN223-3 was used as a control to directly compare expression relative to the 3'UTRs of per5 and nos in combination with the maize ubiquitin 1 (Ubi1) promoter and intron 1.

TABLE 20

Summary of transient GUS expression for all of the constructs tested.

| Construct | GUS/LUC Ratio (% of pDAB305) |
|---|---|
| pDAB305 (35T/GUS/nos) (control) | *100 |
| pTGP190-1 (35T/GUS/per5) | *114 |
| pUGN223-3 (Ubi/GUS/nos) (control) | †137 |
| pUGP232-4 (Ubi/GUS/per5) | †163 |

*not significantly different (p = 0.05)
†significantly different (p = 0.05)

Transient analysis indicated that the per5 3'UTR functioned as well as nos when the GUS gene was driven by the 35T promoter and 19% better than nos when driven by the maize Ubiquitin 1 promoter. The reason for this increased efficiency is not known, but it could result from changes in the efficiency of processing or increased stability of the message.

EXAMPLE 23

Comparison of GUS Expression in Transformed Rice for Per5 3'UTR and nos 3'UTR Constructs This example measures quantitative GUS expression levels obtained when the 3'UTR is used as a polyadenylation regulatory sequence, UGP232-4, in transgenic rice plants. In this example the GUS gene is driven by the maize ubiquitin1 (Ubi1) promoter. Expression levels are compared with the nos 3'UTR sequence and the same promoter (Ubi1)/GUS fusion, pDAB1518 (described in Example 28).

A. Transgenic Production. As described in Example 9.
  1. Plasmids. The plasmid UGP232-4, containing the GUS gene driven by the maize ubiquitin1 promoter and the Per5 3'UTR was described in Example 21. The plasmid pDAB354, which carries a gene for hygromycin resistance, was described in Example 25.
  2. Rice Transformation. Production of transgenic rice plants was described in Example 9.
B. Expression Analysis. Analysis of GUS expression and Southern analysis techniques were described in Example 9. These results are summarized in Table 21 for 30 independent transgenic events recovered with UGP232-4 and 8 independent events from the control plasmid, pDAB1518 (described in Example 28).

TABLE 21

GUS Expression in Transformed Rice Plants For PER5 and NOS 3' UTR Constructs

| Transgenic Event | GUS Activity (RLU /µg protein) Root | Leaf | Presence of Intact Construct |
|---|---|---|---|
| 354/UGP-45 | 349,310 | 295,012 | YES |
| 354/UGP-36 | 326,896 | 172,316 | YES |
| 354/UGP-39 | 152,961 | 127,619 | YES |
| 354/UGP-40 | 126,027 | 106,275 | YES |
| 354/UGP-02 | 58,359 | 21,720 | YES |
| 354/UGP-03 | 54,509 | 20,758 | YES |
| 354/UGP-04 | 54,501 | 20,838 | YES |
| 354/UGP-10 | 53,222 | 26,514 | YES |
| 354/UGP-37 | 45,288 | 90,428 | YES |
| 354/UGP-34 | 43,226 | 7,180 | NO* |
| 354/UGP-48 | 37,284 | 28,029 | YES |
| 354/UGP-29 | 35,630 | 14,631 | NO* |

TABLE 21-continued

GUS Expression in Transformed Rice Plants For PER5 and NOS 3' UTR Constructs

| Transgenic Event | GUS Activity (RLU /μg protein) | | Presence of Intact Construct |
|---|---|---|---|
| | Root | Leaf | |
| 354/UGP-28 | 32,177 | 16,317 | YES |
| 354/UGP-19 | 29,646 | 13,143 | NO* |
| 354/UGP-31 | 29,520 | 19,774 | YES |
| 354/UGP-50 | 11,320 | 9,752 | YES |
| 354/UGP-44 | 9,301 | 9,556 | NO* |
| 354/UGP-35 | 7,113 | 2,062 | YES |
| 354/UGP-17 | 4,590 | 3,350 | YES |
| 354/UGP-27 | 3,367 | 975 | YES |
| 354/UGP-38 | 1,567 | 258 | YES |
| 354/UGP-22 | 1,202 | 1,229 | YES |
| 354/UGP-12 | 903 | 15 | YES |
| 354/UGP-42 | 670 | 780 | NO* |
| 354/UGP-11 | 378 | 96 | YES |
| 354/UGP-26 | 160 | 80 | YES |
| 354/UGP-25 | 152 | 340 | YES |
| 354/UGP-18 | 77 | 26 | YES |
| 354/UGP-06 | 69 | 95 | YES |
| 354/UGP-24 | 43 | 26 | YES |
| 1518-03 | 278,286 | 108,075 | n.d. |
| 1518-08 | 140,952 | 42,867 | n.d. |
| 1518-09 | 97,769 | 83,209 | n.d. |
| 1518-24 | 84,844 | 45,807 | n.d. |
| 1518-23 | 47,734 | 62,279 | n.d. |
| 1518-07 | 2,406 | 3,146 | n.d. |
| 1518-10 | 2,188 | 1,759 | n.d. |
| 1518-04 | 44 | 52 | n.d. |

*The expected 3.9 kb fragment was not obtained but instead a range of 2 to 4 other hybridization bands were noted.
n.d. = not determined For both constructs there was a great deal of variability of GUS expression observed in both roots and leaves. Although a few events displayed higher GUS expression with the UGP construct, overall the expression levels using the per5 3'UTR were comparable to that of the nos 3'UTR. Southern analysis of plants from the 30 UGP232-4 events verified a corresponding 3.9 kb fragment to the GUS probe for the majority of events. Overall, the per5 3'UTR demonstrates the ability to augment expression as good, or better than the nos 3'UTR. The per5 3'UTR has also been used to express the GUS reporter gene in stably transformed maize (Examples 16). Therefore, this sequence has broad utility as a 3'UTR for expression of transgenic products in monocots, and probably in dicots.

Various combinations of the regulatory sequences from the Per5 gene have proven to have utility in driving the expression of transgenic products in multiple crops. Table 22 summarizes the transient and stable expression patterns observed from each of the constructs tested in maize and the stable expression patterns observed in rice. These data demonstrate the ability of any of the per5 promoter iterations to drive transgene expression. An unexpected funding was that introns significantly affect tissue specificity of transgene expression in stably transformed maize plants, but do not similarly affect expression in rice. In stably transformed maize plants the Adh1 intron supported expression in all tissues, whereas the per5 intron supported a tissue preferential pattern of expression. Finally, the per5 3'UTR was capable of supporting transgenic expression when used in combination with the per5 promoter or other heterologous promoters in maize or rice.

TABLE 22

Summary of GUS expression patterns observed from various per5 elements.

| Promoter | Intron | 3'UTR | Transient (root) | Stable Maize | Stable Rice |
|---|---|---|---|---|---|
| per5 | | nos | positive (low) | negative | n.d. |
| per5 | | per5 | positive | negative | constitutive |
| per5 | adh1 | nos | positive | constitutive | constitutive |
| per5 | per5 | per5 | n.d. | root specific | n.d. |
| 35T | adh1 | per5 | positive | n.d. | n.d. |
| ubi | ubi | nos | positive (high) | n.d. | constitutive |
| ubi | ubi | per5 | positive (high) | n.d. | constitutive | n.d. = not determined

EXAMPLE 24 pDAB305

Plasmid pDAB305 is a 5800 bp plasmid that harbors a promoter containing tandem copy of the Cauliflower Mosaic Virus 35S enhancer (35S), a deleted version of the Adh1 intron 1, and the untranslated leader from the Maize Streak Mosaic Virus Coat Protein fused to the β-glucuronidase gene, which is then followed by the nos 3'UTR.

A. Construction of a Doubly-enhanced CaMV 35S Promoter.

This section describes molecular manipulations which result in a duplication of the expression-enhancer element of a plant promoter. This duplication has been shown (Kay et al (1987)) to result in increased expression in tobacco plants of marker genes whose expression is controlled by such a modified promoter. [Note: The sequences referred to in this discussion are derived from the Cabb S strain of Cauliflower Mosaic Virus (CaMV). They are available as the MCAS-TRAS sequence of GenBank, which is published. (Franck et al., 1980). All of the DNA sequences are given in the conventional 5' to 3' direction. The starting material is plasmid pUC13/35S(-343) as described by Odell et al. (1985). This plasmid comprises, starting at the 3' end of the SmaI site of pUC13 (Messing(1983)) and reading on the strand contiguous to the noncoding strand of the lacZ gene of pUC13, nucleotides 6495 to 6972 of CaMV, followed by the linker sequence CATCGATG (which contains a ClaI recognition site), followed by CaMV nucleotides 7089 to 7443, followed by the linker sequence CAAGCTTG, the latter sequence comprising the recognition sequence for HindIII, which is then followed by the remainder of the pUC13 plasmid DNA.

1. pUC13/35S(-343) DNA was digested with ClaI and NcoI, the 3429 base pair (bp) large fragment was separated from the 66 bp small fragment by agarose gel electrophoresis, and then purified by standard methods.

2. pUC13/35S(-343) DNA was digested with ClaI, and the protruding ends were made flush by treatment with T4 DNA polymerase. The blunt-ended DNA was the ligated to synthetic oligonucleotide linkers having the sequence CCCATGGG, which includes an NcoI recognition site. The ligation reaction was transformed into competent Escherichia coli cells, and a transformant was identified that contained a plasmid (named pOO#1) that had an NcoI site positioned at the former ClaI site. DNA of pOO#1 was digested with NcoI and the compatible ends of the large fragment were religated, resulting in the deletion of 70 bp from pOO#1, to generate intermediate plasmid pOO#1 NcoΔ.

3. pOO#1 NcoΔDNA was digested with EcoRV, and the blunt ends were ligated to ClaI linkers having the sequence CATCGATG. An *E. coli* transformant harboring a plasmid having a new ClaI site at the position of the previous EcoRV site was identified, and the plasmid was named pOO#1 NcoΔ RV>Cla.

4. DNA of pOO#1 NcoΔ RV>Cla DNA was digested with ClaI and NcoI, and the small (268 bp) fragment was purified from an agarose gel. This fragment was then ligated to the 3429 bp ClaI/NcoI fragment of pUC13/35S(−343) prepared above in step 1, and an *E. coli* transformant that harbored a plasmid having ClaI/NcoI fragments 3429 and 268 bp was identified. This plasmid was named pUC13/35S En.

5. pUC13/35S En DNA was digested with NcoI, and the protruding ends were made blunt by treatment with T4 DNA polymerase. The treated DNA was then cut with SmaI, and was ligated to BglII linkers having the sequence CAGATCTG. An *E. coli* transformant that harbored a plasmid in which the 416 bp SmaI/NcoI fragment had been replaced with at least two copies of the BglII linkers was identified, and named p35S En$^2$. [NOTE: The tandomization of these BglII linkers generate, besides BglII recognition sites, also PstI recognition sites, CTGCAG].

The DNA structure of p35s En$^2$ is as follows: Beginning with the nucleotide that follows the third C residue of the SmaI site on the strand contiguous to the noncoding strand of the lacZ gene of pUC13; the linker sequence CAGATCT-GCAGATCTGCATGGGCGATG (SEQ ID NO 28), followed by CaMV nucleotides 7090 to 7344, followed by the ClaI linker sequence CATCGATG, followed by CaMV nucleotides 7089 to 7443, followed by the HindIII linker sequence CAAGCTT, followed by the rest of pUC13 sequence. This structure has the feature that the enhancer sequences of the CaMV 35S promoter, which lie in the region upstream of the EcoRV site in the viral genome (nts 7090 to 7344), have been duplicated. This promoter construct incorporates the native 35S transcription start site, which lies 11 nucleotides upstream of the first A residue of the HindIII site.

B. Plasmids Utilizing the 35S Promoter and the Agrobacterium nos Poly A Sequences.

The starting material for the first construct is plasmid pBI221, purchased from CLONTECH (Palo Alto, Calif.). This plasmid contains a slightly modified copy of the CaMV 35S promoter, as described in Bevan et al. (1985), Baulcombe et al. (1986), Jefferson et al., (1986) and Jefferson (1987). Beginning at the 3' end of the Pst I site of pUC19 (Yanisch-Perron et al. (1985)) and reading on the same strand as that which encodes the lacZ gene of pUC19, the sequence is comprised of the linker nucleotides GTCCCC, followed by CaMV nucleotides 6605 to 7439 (as described in 24A), followed by the linker sequence GGG-GACTCTAGA<u>GGATC</u>CCCGGGTGGTCAGTCCCTT (SEQ ID NO 29), wherein the underlined bases represent the BamHI recognition sequence. These bases are then followed by 1809 bp comprising the coding sequence of the *E. coli* uidA gene, which encodes the β-glucuronidase (GUS) protein, and 55 bp of 3' flanking bases that are derived from the *E. coli* genome (Jefferson, 1986), followed by the SacI linker sequence GAGCTC, which is then followed by the linker sequence GAATTTCCCC (SEQ ID NO 30). These bases are followed by the RNA transcription termination/polyadenylation signal sequences derived from the *Agrobacterium tumefaciens* nopaline synthase (nos) gene, and comprise the 256 bp Sau3A I fragment corresponding to nucleotides 1298 to 1554 of DePicker et al. (1982), followed by two C residues, the EcoRI recognition sequence GAATTC, and the rest of pUC19.

1. pBI221 DNA was digested with EcoRI and BamHI, and the 3507 bp fragment was purified from an agarose gel. pRAJ275 (CLONTECH, Jefferson, 1987) DNA was digested with EcoRI and SalI, and the 1862 bp fragment was purified from an agarose gel. These two fragments were mixed together, and complementary synthetic oligonucleotides having the sequence GATCCGGATCCG (SEQ ID NO 31) and TCGACGGATCCG (SEQ ID NO 32) were added. [These oligonucleotides when annealed have protruding single-stranded ends compatible with the protruding ends generated by BamHI and SalI.] The fragments were ligated together, and an *E. coli* transformant harboring a plasmid having the appropriate DNA structure was identified by restriction enzyme analysis. DNA of this plasmid, named pKA881, was digested with BalI and EcoRI, and the 4148 bp fragment was isolated from an agarose gel. DNA pBI221 was similarly digested, and the 1517 bp EcoRI/BalI fragment was gel purified and ligated to the above pKA881 fragment, to generate plasmid pKA882.

2. pKA882 DNA was digested with SacI, the protruding ends were made blunt by treatment with T4 DNA polymerase, and the fragment was ligated to synthetic BamHI linkers having the sequence CGGATCCG. An *E. coli* transformant that harbored a plasmid having BamHI fragments of 3784 and 1885 bp was identified and named pKA882B.

3. pKA882B DNA was digested with BamHI, and the mixture of fragments was ligated. An *E. coli* transformant that harbored a plasmid that generated a single 3783 bp fragment upon digestion with BamHI was identified and named p35S/nos. This plasmid has the essential DNA structure of pBI221, except that the coding sequences of the GUS gene have been deleted. Therefore, CaMV nucleotides 6605 to 7439 are followed by the linker sequence GGGGAC<u>T</u>CTAGA<u>GGATCC</u>CGAATTTCCCC (SEQ ID NO 33), where the single underlined bases represent an XbaI site, and the double underlined bases represent a BamHI site. The linker sequence is then followed by the nos Polyadenylation sequences and the rest of pBI221.

4. p35S/nos DNA was digested with EcoRV and PstI, and the 3037 bp fragment was purified and ligated to the 534 bp fragment obtained from digestion of p35S En$^2$ DNA with EcoRV and PstI. An *E. coli* transformant was identified that harbored a plasmid that generated fragments of 3031 and 534 bp upon digestion with EcoRV and PstI, and the plasmid was named p35S En$^2$/nos. This plasmid contains the duplicated 35S promoter enhancer region described for p35S En$^2$ in Example 24A Step 5, the promoter sequences being separated from the nos polyadenylation sequences by linker sequences that include unique XbaI and BamHI sites.

C. Construction of a Synthetic Untranslated Leader.

This example describes the molecular manipulations used to construct a DNA fragment that includes sequences which comprise the 5' untranslated leader portion of the major rightward transcript of the Maize Streak Virus (ISV) genome. The MSV genomic sequence was published by Mullineaux et al., (1984), and Howell (1984), and the transcript was described by Fenoll et al. (1988). The entire sequence, comprising 154 bp, was constructed in three stages (A, B, and C) by assembling blocks of synthetic oligonucleotides.

1. The A Block: Complementary oligonucleotides having the sequence GATCCAGCTGAAGGCTCGACAAGGCA-GATCCACGGAGGAGCTGATATTTGGTGG ACA (SEQ ID NO 34) and AGCTTGTCCACCAAATATCAGCTC-CTCCGTGGATCTGCCTTGTCCAGCCTTCAGC TG (SEQ ID NO 35) were synthesized and purified by standard procedures. Annealing of these nucleotides into double-stranded structures leaves 4-base single stranded protruding ends [hereinafter referred to as "sticky ends"] that are compatible with those generated by BamHI on one end of the molecule (GATC), and with HindIII-generated single stranded ends on the other end of the molecule (AGCT). Such annealed molecules were ligated into plasmid Bluescript ® II SK⁻ that had been digested with BamHI and HindIII. The sequence of these oligonucleotides is such that, when ligated onto the respective BamHI and HindIII sticky ends, the sequences of the respective recognition sites are maintained. An $E.$ $coli$ transformant harboring a plasmid containing the oligonucleotide sequence was identified by restriction enzyme analysis, and the plasmid was named pMSV A.

2. The B Block: Complementary oligonucleotides having the sequences AGCTGTGGATAGGAGCAACCCTATC-CCTAATATACC AGCACCACCAAGTCAGGGCAAT CCCGGG(SEQ ID NO 36) and TCGACCCGGGATTGC CCTGACTTGGTGGTGCTGGTATATTAGGG ATAGGGTTGCT CCTATCCAC (SEQ ID NO 37) were synthesized and purified by standard procedures. The underlined bases represent the recognition sequence for restriction enzymes SmaI and XmaI. Annealing of these nucleotides into double-stranded structures leaves 4-base sticky ends that are compatible with those generated by HindIII on one end of the molecule (AGCT), and with SalI-generated sticky ends on the other end of the molecule (TCGA). The sequence of these oligonucleotides is such that, when ligated onto the HindIII sticky ends, the recognition sequence for HindIII is destroyed.

DNA of pMSV A was digested with HindIII and SalI, and was ligated to the above annealed oligonucleotides. An $E.$ $coli$ transformant harboring a plasmid containing the new oligonucleotides was identified by restriction enzyme site mapping, and was named pMSV AB.

3. The C Block: Complementary oligonucleotides having the sequences CCGGGCCATTTGTTCCAGGCACGG-GATAAGCATTCAGCCATGGGATATCAAGCTTGGAT CCC (SEQ ID NO 38) and TCGAGGGATCCAAGCTTGA TATCCCATGGCTGA ATGCTTATCCCGTGCCTGGAAC AAATGGC (SEQ ID NO 39) were synthesized and purified by standard procedures. The oligonucleotides incorporate bases that comprise recognition sites (underlined) for NcoI (CCATGG), EcoRV (GATATC), HindIII (AAGCTT), and BamHI (GGATCC). Annealing of these nucleotides into double-stranded structures leaves 4-base sticky ends that are compatible with those generated by XmaI on one end of the molecule (CCGG), and with XhoI-generated sticky ends on the other end of the molecule (TCGA). Such annealed molecules were ligated into pMSV AB DNA that had been digested with XmaI and XhoI. An $E.$ $coli$ transformant harboring a plasmid containing the oligonucleotide sequence was identified by restriction enzyme analysis, and DNA structure was verified by sequence analysis. The plasmid was named pMSV CPL; it contains the A, B and C blocks of nucleotides in sequential order ABC. Together, these comprise the 5' untranslated leader sequence ("L") of the MSV coat protein ("CP") gene. These correspond to nucleotides 167 to 186, and 188 to 317 of the MSV sequence of Mullineaux et al., (1984), and are flanked on the 5' end of the BamHI linker sequence GGATCCAG, and on the 3' end by the linker sequence GATATCAAGCTTGGATCCC (SEQ ID NO 40). [Note: An A residue corresponding to base 187 of the wild type MSV sequence was inadvertently deleted during cloning.]

4. BglII Site Insertion: pMSV CPL DNA was digested at the SmaI site corresponding to base 277 of the MSV genomic sequence, and the DNA was ligated to BglII linkers having the sequence CAGATCTG. An $E.$ $coli$ transformant harboring a plasmid having a unique BglII site at the position of the former Sma I site was identified and verified by DNA sequence analysis, and the plasmid was named pCPL-Bgl.

D. Construction of a Deleted Version of the Maize Alcohol Dehydrogenase 1 (Adh1) intron 1

The starting material is plasmid pVW119, which was obtained from V. Walbot, Stanford University, Stanford, Calif. This plasmid contains the DNA sequence of the maize Adh1.S gene, including intron 1, from nucleotides 119 to 672 [numbering of Dennis et al. (1984)], and was described in Callis et al. (1987). In pVW119, the sequence following base 672 of Dennis et al. (1984) is GAC<u>GGATCC</u>, where the underlined bases represent a BamHI recognition site. The entire intron 1 sequence, with 14 bases of exon 1, and 9 bases of exon 2, can be obtained from this plasmid on a 556 bp fragment following digestion with BclI and BamHI.

1. Plasmid pSG3525a(Pst) DNA was digested with BamHI and BclI, and the 3430 bp fragment was purified from an agarose gel. [NOTE: The structure of plasmid pSG3525a(Pst) is not directly relevant to the end result of this construction series. It was constructed during an unrelated series, and was chosen because it contained restriction recognition sites for both BclI and BamHI, and lacks HindIII and StuI sites. Those skilled in the art will realize that other plasmids can be substituted at this step with equivalent results.] DNA of plasmid pVW119 was digested with BamHI and BclI, and the gel purified fragment of 546 bp was ligated to the 3430 bp fragment. An $E.$ $coli$ transformant was identified that harbored a plasmid that generated fragments of 3430 and 546 upon digestion with BamHI and BclI. This plasmid was named pSG AdhA1.

2. DNA of pSG AdhA1 was digested with HindIII, [which cuts between bases 209 and 210 of the Dennis et al., (1984) sequence, bottom strand], and with StuI, which cuts between bases 554 and 555. The ends were made flush by T4 DNA polymerase treatment, and then ligated. An $E.$ $coli$ transformant that harbored a plasmid lacking HindIII and StuI sites was identified, and the DNA structure was verified by sequence analysis. The plasmid was named pSG AdhA1Δ. In this construct, 344 bp of DNA have been deleted from the interior of the intron 1. The loss of these bases does not affect splicing of this intron. The functional intron sequences are obtained on a 213 bp fragment following digestion with BclI and BamHI.

3. DNA of plasmid pCPL-Bgl (Example 24C Step 4), was digested with BglII, and the linearized DNA was ligated to the 213 bp BclI/BamHI fragment containing the deleted version of the Adh1.S intron sequences from pSG AdhA1Δ. [Note: The sticky ends generated by digestion of DNA with BglII, BclI, and BamHI are compatible, but ligation of the BamHI or BclI sticky ends onto ones generated by BglII creates a sequence not cleaved by any of these three enzymes.] An $E.$ $coli$ transformant was identified by restriction enzyme site mapping that harbored a plasmid that contained the intron sequences ligated into the BglII site, in the orientation such that the BglII/BclI juncture was nearest the 5' end of the MSV CPL leader sequence, and the BglII/BamHI juncture was nearest the 3' end of the CPL. This orientation was confirmed by DNA sequence analysis. The plasmid was named pCPL A1I1Δ. The MSV leader/intron sequences can be obtained from this plasmid by digestion with BamHI and NcoI, and purification of the 373 bp fragment.

E. Construction of Plant Expression Vectors Based on the Enhanced 35S Promoter, the MSV CPL, and the Deleted Version of the Adh1 Intron 1

1. DNA of plasmid p35S En$^2$/nos was digested with BamHI, and the 3562 bp linear fragment was ligated to a 171 bp fragment prepared from pMSV CPL DNA digested with BamHI. This fragment contains the entire MSV CPL sequence described in Example 7C. An *E. coli* transformant was identified by restriction enzyme site mapping that harbored a plasmid that contained these sequences in an orientation such that the NcoI site was positioned near the nos Poly A sequences. This plasmid was named p35S En$^2$ CPL/nos. It contains the enhanced version of the 35S promoter directly contiguous to the MSV leader sequences, such that the derived transcript will include the MSV sequences in its 5' untranslated portion.

2. DNA of plasmid pKA882 (see Example 24B Step 1) was digested with HindIII and NcoI, and the large 4778 bp fragment was ligated to an 802 bp HindIII/NcoI fragment containing the enhanced 35S promoter sequences and MSV leader sequences from p35S En$^2$ CPL/nos. An *E. coli* transformant harboring a plasmid that contained fragments of 4778 and 802 bp following digestion with HindIII and NcoI was identified, and named pDAB310. In this plasmid, the enhanced version of the 35S promoter is used to control expression of the GUS gene. The 5' untranslated leader portion of the transcript contains the leader sequence of the MSV coat protein gene.

3. DNA of plasmid pDAB310 was digested with NcoI and Sac I. The large 3717 bp fragment was purified from an agarose gel and ligated to complementary synthetic oligonucleotides having the sequences CGGTACCTCGAGT-TAAC (SEQ ID NO 41) and CATGGTTAACTCGAGG-TACCGAGCT (SEQ ID NO 42). These oligonucleotides, when annealed into double stranded structures, generate molecules having sticky ends compatible with those left by SacI, on one end of the molecule, and with NcoI on the other end of the molecule. In addition to restoring the sequences of the recognition sites for these two enzymes, new sites are formed for the enzymes KpnI (GGTACC), XhoI (CTCGAG), and HpaI (GTTAAC). An *E. coli* transformant was identified that harbored a plasmid that contained sites for these enzymes, and the DNA structure was verified by sequence analysis. This plasmid was named pDAB1148.

4. DNA of plasmid pDAB1148 was digested with BamHI and NcoI, the large 3577 bp fragment was purified from an agarose gel and ligated to a 373 bp fragment purified from pCPL A1I1_(Example 24D Step 3) following digestion with BamHI and NcoI. An *E. coli* transformant was identified that harbored a plasmid with BamHI and NcoI, and the plasmid was named pDAB303. This plasmid has the following DNA structure: beginning with the base after the final G residue of the PstI site of pUC19 (base 435), and reading on the strand contiguous to the coding strand of the lacZ gene, the linker sequence ATCTGCATGGGTG (SEQ ID NO 43), nucleotides 7093 to 7344 of CaMV DNA, the linker sequence CATCGATG, nucleotides 7093 to 7439 of CaMV, the linker sequence GGGGACTCTAGAGGATC-CAG (SEQ ID NO 44), nucleotides 167 to 186 of MSV, nucleotides 188 to 277 of MSV, a C residue followed by nucleotides 119 to 209 of Adh1.S, nucleotides 555 to 672 of maize Adh1.S, the linker sequence GACGGATCTG, nucleotides 278 to 317 of MSV, the polylinker sequence GTTAACTCGAGGTACCGAGCTCGAATTTCCCC (SEQ ID NO 45) containing recognition sites for HpaI, XhoI, KpnI, and SacI, nucleotides 1298 to 1554 of nos, and a G residue followed by the rest of the pUC19 sequence (including the EcoRI site). It is noteworthy that the junction between nucleotide 317 of MSV and the long polylinker sequence creates an NcoI recognition site.

5. DNA of plasmid pDAB303 was digested with NcoI and SacI, and the 3939 bp fragment was ligated to the 1866 bp fragment containing the GUS coding region prepared from similarly digested DNA of pKA882. The appropriate plasmid was identified by restriction enzyme site mapping, and was named pDAB305. This plasmid has the enhanced promoter, MSV leader and Adh1 intron arrangement of pDAB303, positioned to control expression of the GUS gene.

EXAMPLE 25

Plasmid pDAB354

All procedures were by standard methods as taken from Maniatis et al., (1982).

Step 1: Plasmid pIC19R (Marsh et al., (1984) was digested to completion with restriction enzyme SacI, the enzyme was inactivated by heat treatment, and the plasmid DNA was ligated on ice overnight with an 80-fold excess of nonphosphorylated oligonucleotide linker having the sequence 5' GAGTTCAGGCTTTTTCATAGCT 3' (SEQ ID NO 46), where AGCT is complementary to the overhanging ends generated by SacI digestion. The linker-tailed DNA was then cut to completion with enzyme HindIII, the enzyme was inactivated, and the DNA precipitated with ethanol.

Step 2: Plasmid pLG62 contains a 3.2 Kb SalI fragment that includes the hygromycin B phosphotransferase (resistance) gene as set forth in Gritz and Davies (1983). One microgram of these fragments was isolated from an agarose gel and digested to completion with restriction enzyme Hph I to generate fragments of 1257 bp. The enzyme was inactivated, and the 3' ends of the DNA fragments were resected by treatment with T4 DNA polymerase at 37° for 30 min in the absence of added deoxynucleotide triphosphates.

Step 3: Following inactivation of the polymerase and ethanol precipitation of the DNA, the fragments prepared in Step 2 were mixed in Nick Translation Salts (Maniatis et al., 1982) with the linker-tailed vector prepared in Step 1, heated 5 min at 65°, and slowly cooled to 37°. The non-annealed ends were made blunt and single-stranded regions filled in by treatment with the Klenow fragment of *Escherichia coli* DNA polymerase by incubation at 37° for 45 min, and then the mixture was ligated overnight at 15°. Following transformation into *E. coli* MC1061 cells and plating on LB agar with 50 μg each of ampicillin and hygromycin B, an isolate was identified that contained a plasmid which generated appropriately-sized fragments when digested with EcoRI, PstI, or HincII. DNA sequence determination of a portion of this plasmid (pHYG1) revealed the sequence 5' AGATCTCGTGAGATA<u>ATG</u>AAAAAG 3', (SEQ ID NO 47) where the underlined ATG represents the start codon of the hygromycin B resistance gene, and AGATCT is the BglII recognition sequence. In pHYG1, downstream of the hygromycin B resistance coding region, are about 100 bases of undetermined sequence that were deleted in the next step.

Step 4: DNA of plasmid pHYGI was digested to completion with restriction enzyme BamHI, and the linear fragment thus produced was partially digested with ScaI. Fragments of 3644 bp were isolated from an agarose gel and ligated to phosphorylated, annealed complementary oligonucleotides having the sequences: 5' ACTCGCCGATAGTGGAAAC- CGACGCCCCAGCACTCGTCCGAGGGCAAAGGAA TAGTAAGAGCTCGG 3' (SEQ ID NO 48), and 5' GATC-CCGAGCTCTTACTATTCCTTTGCC CTCGGACGAGT-GCTGGGGCGTCGGTTTCCACTATCGGCGAGT 3' (SEQ ID NO 49).

When annealed, these oligonucleotides have a protruding 4-base overhang on one end that is complementary to that generated by BamHI. Following transformation of the ligation mixture into *E. coli* DH5α cells and selection on LB media containing 50 μg/ml of ampicillin, a transformant was identified that contained a plasmid which generated expected fragments when digested with BamHI, BglII, EcoRI, or SacI. This plasmid was named pHYG1 3'Δ. The sequence of this plasmid downstream from the stop codon of the hygromycin B resistance coding region (underlined TAG in above sequence; Gritz and Davies, 1983) encodes the recognition sequence for SacI.

Step 5. DNA of plasmid pDAB309 was digested to completion with restriction enzyme BsmI, and the ends were made blunt by treatment with T4 DNA polymerase. Plasmid pDAB309 has the same basic structure as pDAB305 described elsewhere herein, except that a kanamycin resistance (NPTII) coding region is substituted for the GUS coding region present in pDAB305. This DNA was then ligated to phosphorylated, annealed oligonucleotide BglII linkers having the sequence 5' CAGATCTG 3'. A transformed colony of DH5α cells harboring a plasmid that generated appropriately-sized fragments following BglII digestion was identified. This plasmid was named pDAB309 (Bg). DNA of plasmid pDAB309(Bg) was cut to completion with SacI, and the linearized fragments were partially digested with BglII. Fragments of 3938 bp (having ends generated by BglII and SacI) were isolated from an agarose gel.

Step 6. DNA of plasmid pHYG1 3'Δ was digested to completion with BglII and SacI. The 1043 bp fragments were isolated from an agarose gel and ligated to the 3938 bp BglII/SacI fragments of pDAB309(Bg) prepared above. After transformation into *E. coli* DH5α cells and selection on ampicillin, a transformant was identified that harbored a plasmid which generated the appropriately-sized restriction fragments with BglII plus SacI, PstI, or EcoRI. This plasmid was named pDAB354. Expression of the hygromycin B resistance coding region is placed under the control of essentially the same elements as the GUS coding region in pDAB305.

EXAMPLE 26

Plasmid pDeLux

Production of the GUS protein from genes controlled by different promoter versions was often compared relative to an internal control gene that produced firefly luciferase. DeWet et al (1987). A plasmid (pT3/T7-1 LUC) containing the luciferase (LUC) coding region was purchased from CLONTECH (Palo Alto, Calif.), and the coding region was modified at its 5' and 3' ends by standard methods. Briefly, the sequences surrounding the translational start (ATG) codon were modified to include an NcoI site (CCATGG) and an alanine codon (GCalif.) at the second position. At the 3' end, an Ssp I recognition site positioned 42 bp downstream of the Stop codon of the luciferase coding region was made blunt ended with T4 DNA polymerase, and ligated to synthetic oligonucleotide linkers encoding the BglII recognition sequence. These modifications permit the isolation of the intact luciferase coding region on a 1702 bp fragment following digestion by NcoI and BglII. This fragment was used to replace the GUS gene of plasmid pDAB305 (see Example 24E, step 5), such that the luciferase coding region was expressed from the enhanced 35S promoter, resulting in plasmid pDeLux. The 5' untranslated leader of the primary transcript includes the modified MSV leader/Adh intron sequence.

EXAMPLE 27

Plasmid pDAB367

Plasmid pDAB367 has the following DNA structure: beginning with the base after the final C residue of the SphI site of pUC19 (base 441), and reading on the strand contiguous to the LacZ gene coding strand, the linker sequence CTGCAGGCCGGCCTTAATTAAGCGGC-CGCGTTTAAACGCCCGGGCATTTAAATGGC GCGC-CGCGATCGCTTGCAGATCTGCATGGGTG (SEQ ID NO 50), nucleotides 7093 to 7344 of CaMV DNA (Frank et al. (1980)), the linker sequence CATCGATG, nucleotides 167 to 186 of MSV (Mullineaux et al. (1984)), nucleotides 188 to 277 of MSV (Mullineaux et al. (1984)), a C residue followed by nucleotides 119 to 209 of maize Adh 1S containing parts of exon 1 and intron 1 (Denis et al. (1984)), nucleotides 555 to 672 containing parts of Adh 1S intron 1 and exon 2 (Denis et al. (1984)), the linker sequence GACGGATCTG (SEQ ID NO 51), and nucleotides 278 to 317 of MSV. This is followed by a modified BAR coding region from pIJ4104 (White et al. (1990)) having the AGC serine codon in the second position replaced by a GCC alanine codon, and nucleotide 546 of the coding region changed from G to A to eliminate a BglII site. Next the linker sequence TGAGATCTGAGCTCGAATTTCCCC (SEQ ID NO 52), nucleotides 1298 to 1554 of nos (DePicker et al. (1982)), and a G residue followed by the rest of the pUC19 sequence (including the EcoRI site.).

EXAMPLE 28

Plasmid pDAB1518 pDAB1518 has the following DNA structure: the sequence CCGCGG, bases −899 to +1093 of the maize ubiquitin 1 (Ubi1) promoter and Ubi1 intron 1 described by Christensen et al. (1992), a polylinker consisting of the sequence GGTACCCCGGGGTCGACCATGG (SEQ ID NO: 53) (containing restriction sites for KpnI, SmaI, SalI, and NcoI, with the NcoI site containing the translational fusion ATG), bases 306–2153 of the β-glucuronidase gene from pRAJ220 described by Jefferson et al. (1986), the sequence GGGAATTGGAGCTCGAATTTCCCC (SEQ ID NO: 54), bases 1298 to 1554 of nos (Depicker et al. (1982)), and the sequence GGGAAATTAAGCTT (SEQ ID NO: 55), followed by pUC18 (Yanisch-Perron et al., 1985) sequence from base 398 to base 399 (reading on the strand opposite to the strand contiguous to the LacZ gene coding strand).

EXAMPLE 29

Plasmid pDAB1538 pDAB1538 has the following DNA structure: the sequence AGCGGCCGCATTCCCGG GAAGCTTGCAT-GCCTGCAGAGATCCGGTACCCGGGGATC-CTCTAGAGTCGAC (SEQ ID NO: 56), bases −899 to +1093 of the maize ubiquitin 1 (Ubi1) promoter and Ubi1 intron 1 described by Christensen et al. (1992), a polylinker consisting of the sequence GGTACCCCGGGGTCGAC-CATGGTTAACTCGAGGTACCGAGCTC- GAATTTCCCC (SEQ ID NO: 57), bases 1298 to 1554 of nos (Depicker et al. (1982)), and the sequence GGGAAT-TGGTTTAAACGCGGCCGCTT (SEQ ID NO:58), followed by pUC19 (Yanisch-Perron et al., 1985) sequence starting at base 400 and ending at base 448 (reading on the strand opposite to the strand contiguous to the LacZ gene coding strand). The NcoI site in the Ubi1 sequence beginning at base 143 was replaced by the sequence CCATG-CATGG (SEQ ID NO:59).

REFERENCES

Anderson (1984), *Science*, 226:401.
Armstrong et al. (1991), *Maize Genet, Coop, New Lett.* 65:92.
Austin, G. D. (1994), U.S. Pat. No. 5,362,865.
Ausubel et al. (1987) *Current Protocols in Molecular Biology*, John Wiley and Sons, New York, N.Y.
Baulcombe et al., (1986). Nature 321:446–449.
Beaucage et al. (1981), *Tetrahedron Letters*, 22:1859–1962).
Benfey P. N., L. Ren and N.-H. Chua. (1989), EMBO Journal 8:2195–2202.
Benfey, P. N., and Nam-Hai Chua. (1990), Science 250:959–966.
Bevan et al. (1985), EMBO J. 4:1921–1926.
Bevan et al. (1986) *Nucleic Acids Res.* 14 (11), 4675–4638.
Bohlmann and Apel (1991), *Annu. Rev. Plant Physiol Plant Mol. Biol.*, 42:227–240.
Bradford (1976) *Anal. Biochem.* 72: 248–254.
Brewbaker et al. (1985), *Journal of Heredity*, 76:159–167.
Buffard et al. (1990), *Proc. Natl. Acad. Sci.*, 87:8874–8878.
Callis J., M. Fromm, and V. Walbot. (1987), Gene Dev. 1:1183–1200.
Cammue et al. (1992), *J. Biol. Chem*, 267:2228–2233.
Caruthers (1983) in: *Methodology of DNA and RNA*, (ed.) Weissman.
Christensen, et al. (1992) *Plant Mol. Biol.* 18: 675–689.
Chu (1978), *Proc. Symp. Plant Tissue Culture*, Peking Press, p43–56.
Conkling et al. (1990), *Plant Physiol.*, 93(3), 1203–1211.
Crossway, et al. (1986), *Mol. Gen. Genet.* 202:179–185.
Croy, et al., WO 9113992
Datla, R. S. S. et al. (1993), Plant Science 94:139–149.
De Framond, EPO Application Number 452 269
Deikman et al. (1988), *Embo J.* 7 (11) 3315.
Dennis et al. (1984), *Nucl. Acids Res.* 12:3983–4000.
DePicker et al. (1982), *J. Molec. Appl. Genet.* 1: 561–573.
DeWet et al. (1987), *Molec. Cell Biol.* 7:725–737.
Dityatkin, et al. (1972), *Biochimica et Biophysica Acta*, 281:319–323.
EPO 0 405 696.
Erlich (ed.)(1989)). *PCR Technology: Principles and Applications for DNA Amplification.*
Fenoll et al. (1988), EMBO J. 7:1589–1596.
Fraley, et al. (1986), *CRC Crit. Rev. Plant Sci.*, 4:1–46.
Frank et al. (1980) *Cell* 21:285–294.
Fu et al. (1995), *The Plant Cell*, 7:1387–1394.
Fujiyama et al. (1988), *Eur. J. Biochem.*, 173:681–687.
Gallie et al. (1989), *The Plant Cell*, 1:301–311.
Gamborg et al. (1968), *Exp. Cell Res.* 50: 151–158.
Gaspar et al. (1982), *Peroxidases: A Survey of Their Biochemical and Physiological Roles in Higher Plant* (Univ. of Geneva Press, Geneva).
Gritz et al. (1983), *Gene* 25:179–188.
Grunstein, M. (1992), Scientific American, October 68–74.
Hertig et al. (1991), *Plant Mol. Biol.*, 16:171–174.
Hiatt, et al. (1989), *Nature*, 342:76–78.
Higuchi et al. (1988), *Nucl. Acids Res.*, 16:7351.
Higuchi et al. (1988), *Nucl. Acids Res.*, 16:7351–7367.
Ho et al. (1989), *Gene*, 77:51–59.
Hofte and Whitely (1989), *Microbiol. Rev.*, 53:242–255.
Horton et al. (1989), *Gene*, 77:61.
Howell (1984). Nucl. Acids Res. 12:7359–7375.
Hultmark et al. (1982), *EUR. J. Biochem.*, 127:207–217.
Hultmark et al. (1983), *EMBO J.*, 2:571–576.
Jackson and Standart (1990), Cell 62:15–24.
Jefferson (1987) *Plant Molec. Biol. Reporter* 5:387.
Jefferson et al. (1986), *Proc. Natl. Acad. Sci.* 83:8447–8451.
Jefferson et al. (1987), *EMBO J.* 6: 3901.
Kaiser et al. (1987), *Ann. RevBiophys. Biophys. Chem.*, 16:561–581).
Kat et al. (1987), *Science* 236:1299.
Katsu et al. (1988), *Biochim. Biophys. Acta*, 939:57–63.
Kay et al. (1987), *Science* 236 1299–1302.
Knott et al. (1985), *Science*, 230:37.
Knowles et al. (1987), *Biochim. Biophys. Acta* 924:509–518.
Kozak (1986), *Cell* 44:283–292.
Kriz, A. L. et al. (1987), Molecular and General Genetics 207: 90–98.
Lagrimini et al. (1987), *Plant Physiol.*, 84:438–442.
Lagrimini et al. (1987), *Proc. Natl. Acad. Sci.*, 84:7542–7546.
MD.
Lee, K. and A. H. C. Huang. (1994), *Plant Molecular Biology* 26:1981–1987.
Lewah et al. (1991), *J. Biol. Chem.*, 266:1564–1573.
Li et al. (1993), *Plant Cell Rep.* 12: 250–255.
Linthorst (1991), *Critical Rev. Plant Sci.*, 10:123–150.
Lis et al. (1986), *Ann. Rev. Biochem.*, 55:35–68.
Luehrsen, K. R. and V. Walbot. (1994), Plant Cell Reports 13:454–458.
Mandel and Higa (1972), *J. Mol. Biol.*, 53:159.
Maniatis et al., eds. (1982) *Molecular Cloning*, First Edition, Cold Spring Harbor Press.
Marsh et al. (1984), *Gene* 32:481.
Matzke et al. (1993), *Ann. Rev. Plant Physiol. Plant Mol. Biol.* 44: 53–76.
Mazza and Welinder (1980), *Eur. J. Biochem.* 108:481–489.
McElroy, D. and R. S. Brettell. (1994), *Trends Biotechnology* 12:62–68.
Messing et al. (1983) in: *Genetic Engineering of Plants*, (Kosuga et al. eds.), Plenum Press, pp. 211–227).
Miller, et al. (1988), *Proc. Natl. Acad. Sci. USA*, 85:856–860;
Morgens et al. (1990), *Plant Mol. Biol.*, 14:715.
Mullineaux et al. (1984), EMBO J. 3:3063.
Mullis et al. (1987), *Meth. Enz.*, 155:335.
Murashige and Skoog (1962), *Physiol. Plant*, 15: 473.
Nakagawa et al., (1985) *J. Am. Chem. Soc.*, 107:7087;
Nakamura et al. (1988), *Plant Physiol.*, 88:845.
Odell et al. (1985), *Nature* 313: 810–812.
Oiki et al. (1988), *PNAS USA*, 85:2393–2397.
Pain (1986), *Biochem. J.*, 235:625–637.
Pear et al. (1989), *Plant Mol. Biol.* 13: 639.
Powell, et al (1988), *Appl. Environ. Microbiol.*, 54:655–660.
Raju, S. S. D. et al (1993), Plant Science 94: 139–149.
Rothnie et al. (1994), EMBO Journal, 13:2200–2210.
Ryan (1990), *Annu Rev. Phytopathol.*, 28:425.
Saghai-Maroof et al. (1984), *Proc. Natl. Acad. Sci. USA* 81:8014.
Samac et al. (1990), *Plant Physiol.* 93: 907–914
Sambrook et al. (1989), *Molecular Cloning: A Laboratory Manual*, 2nd edition, Cold Spring Harbor Press, Cold Spring Harbor, N.Y.
Shigekawa and Dower (1988), *Biotechniques*, 6:742.

Southern, E. (1975), *J. Mol. Biol.* 98:503.
Southern, E. (1980), *Methods Enzymol.* 69:152.
Sullivan, M. L and P. Green (1993), *Plant Molecular Biology* 23: 1091–1104.
Tierney et al. (1987), Planta 172: 356.
Tobkes et al. (1985), *Biochem.* 24:1915–1920.
Uchidaz, et al. (1980), in: *Introduction of Macromolecules Into Viable Mammalian Cells*, (Baserga et al., eds.) Wistar Symposium Series, Vol. 1, A. R. Liss Inc., NY, pp. 169–185.
Uchirniya, et al. (1982), in: *Proc. 5th Intl. Cong. Plant Tissue and Cell Culture*, (Fujiwara, ed.), Jap. Assoc. for Plant Tissue Culture, Tokyo, 507.
Vain, P. et al. (1996), Plant Cell Reports 15:489–494.
Vain et al. (1993), *Plant Cell Rep.* 12: 84.
Van Parijis et al. (1991), *Planta*, 183:258.
Vigers et al. (1992), *Plant Sci.*, 83:155.
Viret, J.-F. et al. (1994), Proc. Nat Acad. Sci. 91:8577–8581.
Walbot et al. (1991), ISPMB Third International Congress, Tucson, Ariz. Abstract No. 30.
White et al. (1990), *Nucl. Acids. Res.* 18: 1062.
Wigler, et al. (1979), *Cell*, 16:77.
Wilmink et al. (1995), Plant Molecular Biology 28:949–955.
Woloscuk et al. (1991), *The Plant Cell*, 3:619–628.
Xu et al (1994), Plant Physiol. 106:459–467.
Yamamoto et al. (1991), *Plant Cell*, 3(4):371–382.
Yanisch-Perron et al. (1985), *Gene* 33:103–119.
Zasloff (1987), *PNAS USA*, 84:5449–5453.
Zoller et al. (1984), *DNA*, 3:479.

We claim:

1. An isolated DNA molecule selected from the following per5 promoter sequences bp 4086–4148 of SEQ ID NO 1,
bp 4086 to 4200 of SEQ ID NO 1,
bp 4086 to 4215 of SEQ ID NO 1,
bp 3187–4148 of SEQ ID NO 1,
bp 3187–4200 of SEQ ID NO 1,
bp 3187–4215 of SEQ ID NO 1,
bp 2532–4148 of SEQ ID NO 1,
bp 2532–4200 of SEQ ID NO 1,
bp 2532–4215 of SEQ ID NO 1,
bp 1–4148 of SEQ ID NO 1,
bp 1–4200 of SEQ ID NO 1, and
bp 1–4215 of SEQ ID NO 1.

2. A DNA construct comprising a promoter of claim 1.

3. A transformed plant comprising a promoter of claim 1 operatively linked to heterologous coding sequence.

4. Transformed seed or grain from the transformed plant of claim 3.

* * * * *